(12) United States Patent
Blackshear et al.

(10) Patent No.: US 8,008,463 B2
(45) Date of Patent: Aug. 30, 2011

(54) COMPOSITIONS AND METHODS FOR DIAGNOSTICS AND THERAPEUTICS FOR HYDROCEPHALUS

(75) Inventors: Perry J. Blackshear, Chapel Hill, NC (US); Deborah J. Stumpo, Durham, NC (US); Darryl C. Zeldin, Chapel Hill, NC (US); Joan P. Graves, Raleigh, NC (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 954 days.

(21) Appl. No.: 10/511,362

(22) PCT Filed: Apr. 18, 2003

(86) PCT No.: PCT/US03/12348
§ 371 (c)(1),
(2), (4) Date: Oct. 15, 2004

(87) PCT Pub. No.: WO03/088919
PCT Pub. Date: Oct. 30, 2003

(65) Prior Publication Data
US 2005/0181369 A1 Aug. 18, 2005

Related U.S. Application Data

(60) Provisional application No. 60/374,184, filed on Apr. 19, 2002, provisional application No. 60/388,266, filed on Jun. 13, 2002.

(51) Int. Cl.
*C07H 21/04* (2006.01)
*C12H 15/63* (2006.01)
*C12Q 1/68* (2006.01)
*A01K 67/00* (2006.01)
(52) U.S. Cl. ......... 536/23.5; 435/6; 435/320.1; 435/455
(58) Field of Classification Search ........................ None
See application file for complete search history.

(56) References Cited

U.S. PATENT DOCUMENTS

| 6,812,339 B1 | 11/2004 | Venter et al. | |
|---|---|---|---|
| 6,828,097 B1 * | 12/2004 | Knoll et al. | 435/6 |
| 7,560,542 B2 * | 7/2009 | Andersen et al. | 536/23.6 |
| 2003/0180298 A1 * | 9/2003 | Old et al. | 424/144.1 |

FOREIGN PATENT DOCUMENTS

| WO | WO 84/03564 | 9/1984 |
|---|---|---|
| WO | WO02/086071 | 10/2002 |

OTHER PUBLICATIONS

Araki et al. Restricted expression and photic induction of a novel mouse regulatory factor X4 transcript in the suprachiasmatic nucleus. J. Biol. Chem. 279:10237-10242, 2004.*
Griffin et al. t(11;18)(q21;q21) is a recurrent chromosome abnormality in small lymphocytic lymphoma. Genes, Crhomosimes & Cancer 4:153-157, 1992.*
Attwood, T.K. The Babel of Bioinformatics. Science 290:471-473, 2000.*
Kyrpides et al. Whole-genome sequence annotation: "Going wrong with confidence". Mol. Microbiology 32:886-887, 1999.*
Wells et al. The chemokine information source: Identification and characterization of novel chemokines using the WorldWideWeb and Expressed sequence tag databases. J. Leukoc. Biol. 61:545-550, 1997.*
Gerhold et al. It's the genes! EST access to human genome content. BioEssays 18:973-981, 1996.*
GenBank Accession No. BB611382.1, Oct. 26, 2001; pp. 1-3.*
Brümmendorf et al., "Neural cell recognition molecule L1: from cell biology to human hereditary brain malformations," *Current Opinion in Neurobiology* 8:87-97, 1998.
Gajiwala et al., "Structure of the winged-helix protein hRFX1 reveals a new mode of DNA binding," *Nature*, 403:916-921, 2000.
Morotomi-Yano et al., "Human Regulatory Factor X 4 (RFX4) Is a Testis-specific Dimeric DNA-binding Protein That Cooperates with Other Human RFX Members," *J. Biol. Chem.* 277(1):836-842, 2002.
Pérez-Fígares et al., "Subcommissural Organ, Cerebrospinal Fluid Circulation, and Hydrocephalus," *Microscopy Research and Technique* 52:591-607, 2001.
GenBank Accession No. AF332192, Mar. 11, 2001.
GenBank Accession No. BAC28598, Dec. 5, 2002.
GenBank Accession No. NM_032491, Apr. 6, 2003.
GenBank Accession No. NP_002911, Apr. 6, 2003.
GenBank Accession No. NT_009720, May 8, 2002.
GenBank Accession No. XP_125797, Feb. 24, 2003.
Blackshear et al., "Graded phenotypic response to partial and complete deficiency of a brain-specific transcript variant of the winged helix transcription factor RFX4," *Development* 130(19):4539-4552, 2003.
Dotzlaw et al., "Characterization of estrogen receptor variant mRNAs from human breast cancers," *Mol. Endocrinol.* 6:773-785, 1992.
Miao et al., "Isolation of an allele of reeler by insertional mutagenesis," *Proc. Natl. Acad. Sci. USA* 91(23):11050-11054, 1994.
GenBank Accession No. AA285775, Apr. 9, 1997, 2 pages.
GenBank Accession No. AAK17191, Mar. 11, 2001, 2 pages.
GenBank Accession No. AI462920, Mar. 9, 1999, 2 pages.
GenBank Accession No. AI657628, Jun. 7, 2001, 2 pages.
GenBank Accession No. AK034131, Apr. 3, 2004, 4 pages.
GenBank Accession No. AY102009, Aug. 19, 2003, 3 pages.
GenBank Accession No. AY102010, Sep. 26, 2003, 3 pages.
GenBank Accession No. AY102011, Aug. 19, 2003, 3 pages.
GenBank Accession No. BB379807, Oct. 24, 2001, 3 pages.
GenBank Accession No. BB595996, Oct. 26, 2001, 3 pages.
GenBank Accession No. BB873367, Nov. 27, 2001, 2 pages.

(Continued)

*Primary Examiner* — Quang Nguyen
(74) *Attorney, Agent, or Firm* — Klarquist Sparkman, LLP.

(57) ABSTRACT

The present disclosure relates to RFX4_v3 protein and nucleic acids encoding the RFX4_v3 protein. The present disclosure provides non-human transgenic animals with altered RFX4_v3 genes, and provides assays for the detection of RFX4_v3 and RFX4_v3 polymorphisms associated with disease states. The present disclosure additionally provides methods of determining a subjects' risk of developing congenital hydrocephalus, and treating or inhibiting its development.

31 Claims, 15 Drawing Sheets

OTHER PUBLICATIONS

GenBank Accession No. H10145, Jun. 23, 1995, 2 pages.
GenBank Accession No. NM_000775, Dec. 20, 2004, 4 pages.
GenBank Accession No. NM_002920, Oct. 27, 2004, 3 pages.
GenBank Accession No. NP_115880, Oct. 28, 2004, 2 pages.
GenBank Accession No. NT_035235, Apr. 10, 2003, 2 pages.
GenBank Accession No. NT_039498, Feb. 24, 2003, 6 pages.
GenBank Accession No. U71441, Oct. 21, 1996, 3 pages.
NCBI Trace Archive No. gnl/ti/13973384.
NCBI Trace Archive No. gnl/ti/84074979.
NCBI Trace Archive No. gnl/ti/91911671.

* cited by examiner

FIG. 1 Alignment of mouse sequences with the human chromosome 12 genomic clone NT_009720

Expect = 4e-28, Identities = 179/224 (79%), Gaps = 4/224 (1%)

```
Query:   696  ctttgggacagtgagagctgcctttcatagaaaatggccttgtgctcctgcttcagcca  755
              |||||  |||||||||||| |||||||||||||||| ||    ||||||| |||||||
Sbjct: 315187  ctttggtgcagtgagagccgcctttcataggaaaacagt-ttgtgctccctgactgggcca  315129

Query:   756  cctttcacccccctgctcgatt-gcggagcatgtggtgagagg-cagggataaagggctca  813
              |||||||||  ||||||| || |  |||||||| ||||||||||| |||||||||||||
Sbjct: 315128  cctttcacccctttgttcaagtagcagctcattggtaagggtcaggaataaagggctct  315069

Query:   814  ctctgcccttccatgtgcaggaaagttggcccccaggagtggggagttgtgtcccaaaat  873
              |||||||||||||||||||||||||||||  |||||||| |||||||||||||||||||
Sbjct: 315068  ttcttccctctccatgtgtaggaaagtcagccccttggtgtggagagtcatttctcaaaat  315009

Query:   874  aga-cttcctaatacagttccaaagaggccaagagtcagtcaca  916
              |||  ||||||||  ||||||||||||| ||||||||||||||
Sbjct: 315008  agatcttcctaatatggttccaaagagagcaagagtcagtcaca  314965
```

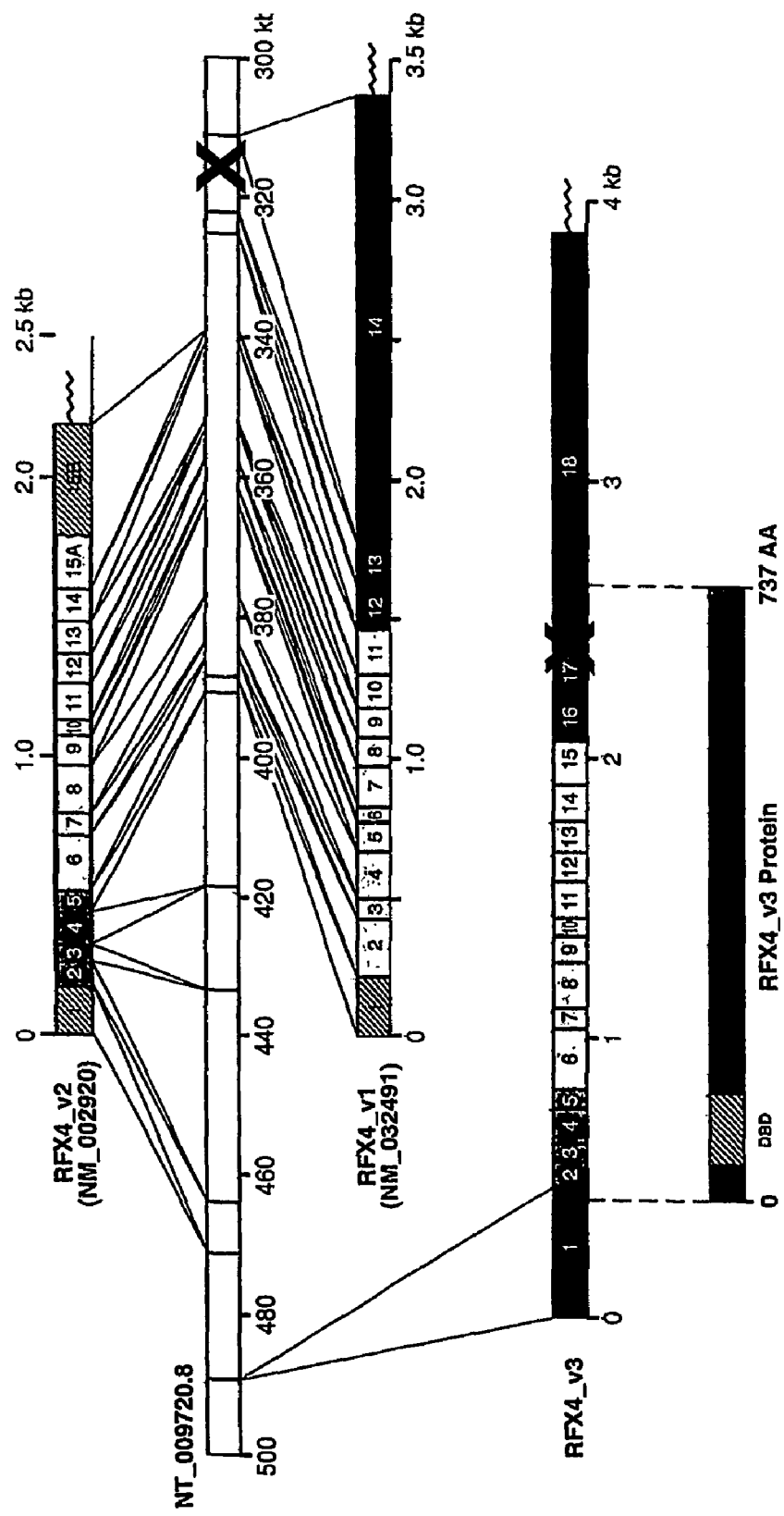
FIG. 2  The Human RFX4 Locus

FIG. 3 Alignment of human and mouse proximal promoters for RFX4_v3

Expect = e-107
Identities = 212/216 (98%)

```
Human  786  gaggggggccacatctaagccaatttttgatttcgcctataatgagtgccgggcgaaggctg  845
            |||||||| ||||| || ||||||||||||||||||||||||||||||||||||| |||||
Mouse   86  gaggggggcagatctaagccaatttttgatttcgtctataatgagtgccgggctaaggctg  145

Human  846  gagaaggcctctggaactttaaataagaaaaacgttgctaatgctatataatagaaggggga  905
            ||||| |||||||||||||||||||||||||||||||||||||||||||||||||||||||
Mouse  146  gagaaggcctctggaactttaaataagaaaaacgttgctaatgctatataatagaaggggga  205

Human  906  agtcggagggctgggattgcgtcgctctgagcccccctttcggaggcggctttcttat  965
            |||||||||||||||||||||||||||||||||||||| |||||||||||||| |||||
Mouse  206  agtcggagggctgggattgcgtcgctctgagcccccctttcggaggcggctttcttat  265

Human  966  tcaaaacaggcccacaatgggcttcac  992
            |||||||||||||||||||||||||||
Mouse  266  tcaaaacaggcccacaatgggcttcac  292
```

FIG. 4 Human, mouse, and zebrafish alignment of RFX4_v3 (amino terminus)

```
human      MHCGLLEEPDMDSTESWIERCLNESENKRYSSHTSLGNVSNDENEEKENNRASKPHSTPA  60
mouse      MHCGLLEEPDMDSTESWIERCLNESENKRYSSHTSLGNVSNDENEEKENNRASKPHSTPA  60
zebrafish  MLCGLLEEPDMDSTESWIERCLNESESKRFSSHSSIGNISNDENEEKENNRASKPHSTPA  60
           * ******************************.*:**.:***************** human      TLQWLEENYEIAEGVCIPRSALYMHYLDFCEKNDTQPVNAASFGKIIRQQFPQLTTRRLG  120
mouse      TLQWLEENYEIAEGVCIPRSALYMHYLDFCEKNDTQPVNAASFGKIIRQQFPQLTTRRLG  120
zebrafish  TLQWLEENYEIAEGVCIPRIALYMHYLDFCEKLDSQPVNAASFGKIIRQQFPQLTTRRLG  120
           ***************** ********* *.************************** human      T--RGQSKYHYYGIAVKESSQYYDVMYSKKGAAWVSETGKKEVSKQTVAYSPRSKLGTLL  178
mouse      TGTRGQSKYHYYGIAVKESSQYYDVMYSKKGAAWVSETGKREVTKQTVAYSPRSKLGTLL  180
zebrafish  T--RGQSKYHYYGIAVKESSQYYDVMYSKKGAAWVNETGK-------------------  158
           *  ********************************.****.
```

FIG. 5  Alignment of human and mouse RFX4_v3

```
human   MHCGLLEEPDMDSTESWIEKCLNESENKPYSSHTSLGNVSNDENEEKENNKASKPHSTPATLQMLEENYEIAEGVCIPRSALYMHYLDFCEKNDTQPVNAASEGKIIRQQFPQLTTRPLG  120
mouse   MHCGLLEEPDMDSTESWIEKCLNESENKPYSSHTSLGNVSNDENEEKENNKASKPHSTPATLQMLEENYEIAEGVCIPRSALYMHYLDFCEKNDTQPVNAASFGKIIRQQFPQLTTRPLG  120
        ********************************************************************************************** **************** human   T--KGQSKYHYYGIAVKESSQYYDVMYSKKGAAWVSETGKREVSKQTVAYSPRSKLGTLLPEEFPNVKDLNLPASLPEEKVSTFIMMYRTHCQKILDTVIRANEDEVQSFLLHFWQGMPPH  238
mouse   TGTPGQSKYHYYGIAVKESSQYYDVMYSKKGAAWVSETGKREVTKQTVAYSPFSKLGTLLPDFPNVKDLNLPASLPEEKVSTFIMMYKTHCQKILDTVIRANEDEVQSFLLHFWQGMPPH  240
         * *********************************  ********** *************  ** *************************** ***** human   MLPVLGSSTVVNIVGVCDSILYKAISGVLMPTVLQALPDSLTQVIRKFAKQLDEWLKVALHDLPENLENIKFELSRKFSQILKQTSLNHLCQASKTVIHSADITFQMLEDWKNVDLNSI  358
mouse   MLPVLGSSTVVNIVGVCDSILYKAISGVLMPTVLQALPDSLTQVIRKFAKQLDEWLKVALHDLPENLENIKFELSRKFSQILKQTSLNHLCQASKTVIHSADITFQMLEDWRNVDLSSI  360
        ************************************************************************************************************* ** human   TKQTLYTMEDSKDEHKKLITQLYQEFDHLLEEQSPIESYIEWLDTMVDKCVVKVAAKPQGSLKKVAQQFLMWSCFGTRVIFDMTLHSAPSFGSFHLIHLMFDDYVLYLLESLHCQERAN  478
mouse   TKQTLYTMEDSKDEHKPLIIQLYQEFDHLLEEQSPIESYIEWLDTMVDPCVVKVAAKPQGSLKKVAQQFLMWSCFGTRVIKDMTLHSAPSFGSFHLIHLMFDDYVLYLLESLHCQEPAN  480
        ************   **************************** ************************** ********************************** human   ELMKAMKGEGSTAEVKEEIILTEAAAPTPSVPSFSFPAKSATSVEVPPPSSPVSNPSFEYTGLSTTGAMQSYTWSLIYTVTTAAGSPAENSQQLPCMKNTHVPSSSVTHKIPVYPHREEH  598
mouse   ELMKAMKGEGSTABAQEEIILTEATPTPSPGPSFSPAKSATSVEVPPSSPVSNPSFEYTGLSTAGAMQSYTWSLIYTVTTAAGSPAENSQQLPCMKSTHMPSSSVTHKIPVYSHHEEH  600
        *********** * * ** ******** *********************************************   ************ * *** human   GYTGSYNYGSYGNQHPHPMQSQYPALPHDTAISGPLHIAPYHKSSAQYPFNSPTSKNEPCLMSSTPFLHPTPVTEPWPEVPSANTCYTPSVHSAKKYGNSSDMYTPLTTKKNSEYEHMQH  718
mouse   GYTGSYNYGSYGNQHPHPLQNQYPALPHDTAISGPLHYSPYHRSSAQYPFNSPTSKMEPCLMSSTPFLHTTPVTPRMPEVPTANACYTSPSVHSTFYGNSSDMYTPLTTRKNSEYEHMQH  720
        ****************** * *************  *:********* :*******   : * *** *************** human   FPGFAYINGEASTGWAK  735
mouse   FPGFAYINGEASTGWAK  737
        *****************
```

```
Human      MHCGLLEEPDMDSTESWIERCLNESENKRYSSHTSLGNVSNDENEEKENNRASKPHSTPA  60
Mouse      MHCGLLEEPDMDSTESWIERCLNESENKRYSSHTSLGNVSNDENEEKENNRASKPHSTPA  60
Zebrafish  MLCGLLEEPDMDSTESWIERCLNESESKRFSSHSSIGNISNDENEEKENNRASKPHSTPA  60
           * ************************.**.***.*.**.********************

TLQWLEENYEIAEGVCIPRSALYMHYLDFCEKNDTQPVNAASFGKIIRQQFPQLTTRRLG 120
           TLQWLEENYEIAEGVCIPRSALYMHYLDFCEKNDTQPVNAASFGKIIRQQFPQLTTRRLG 120
           TLQWLEENYEIAEGVCIPRIALYMHYLDFCEKLDSQPVNAASFGKIIRQQFPQLTTRRLG 120
           ******************* ***********  .*************************

Exons 2-5                                                                          DBD T--RGQSKYHYYGIAVKESSQYYDVMYSKKGAAWVSETGKKEVSKQTVAYSPRSKLGTLL 178
           TGTRGQSKYHYYGIAVKESSQYYDVMYSKKGAAWVSETGKREVTKQTVAYSPRSKLGTLL 180
           T--RGQSKYHYYGIAVKESSQYYDVMYSKKGAAWVNETGKKEVTKQTVAYSPRSKLGTLL 178
           *  *************** ***************.****:**.***************

PEFPNVKDLNLPASLPEHKVSTEIMMYRTHCQRILDTVIRANFDEVQSFLLHFWDGMPPH 238
           PDFPNVKDLNLPASLPEHKVSTFIMMYRTHCQRILDTVIRANFDEVQSFLLHFWDGMPPH 240   B
           PDFPNVKDLNLPASLPEHKVSTEIMMYRTHCQRILDTVIRANFDEVQSFLLHFWDGMPPH 238
           *:************************.*********************************

MLPVLGSSTVVNIVGVCDSILYKAISGVLMPTVLQALPDSLTQVIRKFAKQLDEWLKVAL 298
           MLPVLGSSTVVNIVGVCDSILYKAISGVLMPTVLQALPDSLTQVIRKFAKQLDEWLKVAL 300   C
           MLPVLGSSTVVNIVGVCDSILYKAISGVLMPTVLQALPDSLTQVIRKFAKQLDEWLKVAL 298
           ************************************************************

HDLPENLRNIKFELSRRFSQILRRQTSLNHLCQASRTVIHSADITFQMLEDWRNVDLNSI 358
           HDLPENLRNIKFELSRRFSQILRRQTSLNHLCQASRTVIHSADITFQMLEDWRNVDLSSI 360
           HDLPENLRNIKFELSRRFSQILKRQTSLNHLCQASRTVIHSADITFQMLEDWRNVDLNSI 358
Exons 6-15 **********************.***************************.**.**

TKQTLYTMEDSRDEHRKLTTQLYQEFDHLLEEQSPIESYIEWLDTMVDRCVVKVAAKRQG 418
           TKQTLYTMEDSRDEHRRLTTQLYQEFDHLLEEQSPIESYIEWLDTMVDRCVVKVAAKRQG 420
           TKQTLYTMEDSREDQRRLIIQLYQEFDRLLEDQSPIEAYIEWLDSMVERCVVRVAGKRPG 418
           ***********:.::.** :******.***:***** *******.**:***:** ** *                 DD

SLKKVAQQFLLMWSCEGTRVIRDMTLHSAPSFGSFHLIHLMFDDYVLYLLESLHCQERAN 478
           SLKKVAQQFLLMWSCEGTRVIRDMTLHSAPSFGSFHLIHLMFDDYVLYLLESLHCQERAN 480
           SLKRVAQQFLLMWSCEGTRVIRDMTLHSAPSFGSFHLIHLMFDDYVLYLLESLHCQERAN 478
           ***:***************************************************************

ELMRAMKGDGSTAEVRREEIILTEAAAPTPSPVPSFSPAKSATSMEVPPPSSPVSNPSPEY 538
           ELMRAMKGDGSTAEAQEETILTEATBPTPSPGSFSPAKSATSVEVPPSSPVSNPSPEY 540
           ELMRAMKGDGAPADTGEEIMLMSQTQISTSPGP-YSPAKSVHSVGVPAVGSPNSAQSPEY 537
           **********:.*: .**: *.:.:  .**  *  .****:.**.* * .* .****

TGLS--TTGAMQSYTWSLTYTVTTAAGSPAENSQQLPCMRN-THVPSSSVTHRIPVYPHRE 596
           TGLS--TAGAMQSYTWSLTYTVTTAAGSPAENSQQLPCMRS-THMPSSSVTHRIPVYSHRE 598
           TSISATTGAVQSYTWSLTYTVTTSGGSPTEPGSQLSCMRGGPALHGSSSAHRMPVYPHRD 597
           *.:* *.:*.*:***********.***.*  .: **. . .   *.:***:** * **:

EHGYTGSYNYGSYGNQHPHPMQSQYPALPHDTAISGPLHYAPYHRSSAQYPFNSPTSRME 656
           EHGYTGSYNYGSYGNQHPHPLQNQYPALPHDTAISGPLHYSPYHRSSAQYPFNSPTSRME 658
           EHGYTGSYNYSSYANQHHHAIQSQYSSLTHEAGLPTPLHYSSYHRTSAQYPLNSQMSRME 657
           ********** **.***.*  *.**..* *:: : ***..****:****.**  ****

Exons 16-18 PCLMSSTPRLHPTPVTPRWPEVPSANTCYTSPSVHSARYGNSSDMYTPLTTRRNSEYEHM 716
            PCLMSSTPRLHPTPVTPRWPEVPTANACYTSPSVHSTRYGNSSDMYTPLTTRRNSEYEHM 718
            SCLMSGSPLLHSSPVTPRWPDVPSANSCYSSPTVHASRYS-TGDMYSPLAPRRNSEYEHA 716
            .****.** ** .******:**:**.**:**:** :**. : :***:**  ********

QHFPGFAYINGEASTGWAK 735
           QHFPGFAYINGEASTGWAK 737
           QHFPGFAYINGEATTGWAK 735
           **************:*****
```

FIG. 6

COMPOSITIONS AND METHODS FOR DIAGNOSTICS AND THERAPEUTICS FOR HYDROCEPHALUS

CROSS REFERENCE TO RELATED APPLICATIONS

This is the §371 U.S. National Stage of International Application No. PCT/US03/12348, filed Apr. 18, 2003, which was published in English under PCT Article 21(2), which in turn claims the benefit of U.S. provisional patent application No. 60/374,184 filed Apr. 19, 2002, and U.S. provisional patent application No. 60/388,266 filed Jun. 13, 2002, all three of which are incorporated herein by reference.

FIELD OF THE DISCLOSURE

The present disclosure relates to congenital hydrocephalus, and particularly to a new variant protein that is associated with its development. Also disclosed are methods of determining an individual's risk of developing disease states and conditions.

BACKGROUND

Congenital hydrocephalus is a common birth defect that is estimated to occur with a frequency of 0.5-1.8 per 1000 births (Howard, et al., J. Med. Genet., 18:252-255 [1981]). It has been estimated that about ⅔ of patients with congenital hydrocephalus have some degree of aqueductal stenosis (Duckett, S., Pediatric Neuropathology, p. 199 [1995]) which results in an excess of cerebrospinal fluid (CSF) in the ventricles of the brain. This excess fluid results in expansion and trauma to the surrounding brain tissue. Hydrocephalus has significant social and economic costs. In 1993, surgery for shunt placement cost almost $100 million per year. Congenital hydrocephalus also has adverse effects on the developing brain, which may persist as neurological deficits in children and adults, such as mental retardation, cerebral palsy, epilepsy and visual disabilities.

Many cases of hydrocephalus are caused by chromosome X-linked genetic mutations. Other causes of congenital and familial congenital hydrocephalus are unknown. Current diagnostic procedures are very limited in that they show presence of hydrocephalus after significant malformations have occurred. Some of these diagnostic procedures for hydrocephalus include x-ray, magnetic resonance imaging (MRI) and CAT scans.

Regulatory factor X (RFX) members are evolutionarily conserved transcription factors that share a highly conserved winged helix DNA-binding domain. Human RFX4 contains evolutionarily conserved regions, including a RFX-type DNA-binding domain, a dimerization domain, and other conserved regions, and is closely related to RFX1, RFX2, and RFX3 in structure. RFX4 is associated with breast cancer, and is expressed in testis.

In view of these considerations, there is a need for systems and methods for better understanding, diagnosing, and controlling the complex biological processes that result in congenital hydrocephalus.

SUMMARY OF THE DISCLOSURE

A new splice variant of RFX4 has been found, and is identified herein as RFX4_v3. It has surprisingly been determined that this new variant is associated with the development of neurological structures, and that its reduction or absence promotes the development of congenital hydrocephalus. This disclosure therefore provides a substantially purified RFX4_v3 polypeptide, and in particular such a polypeptide that includes an amino acid sequence at least 70% identical (for example at least 80%, 85%, 90%, or 95% identical), to the human amino acid sequence set forth as SEQ ID NO: 8, a conservative variant of that sequence, or a sequence that is 100% identical to SEQ ID NO: 8. The polypeptide has RFX4_v3 activity, and the N-terminus of the polypeptide is at least 90% (for example at least 95% or 98%) identical to residues 1-14 of the human SEQ ID NO: 8.

In particular embodiments, the RFX4_v3 polypeptide includes a murine amino acid sequence (SEQ ID NO: 6) or a zebrafish sequence (SEQ ID NO: 10), or a sequence having at least 85% identity (for example at least 95% or even 100% sequence identity) to SEQ ID NO: 8.

Also provided are isolated nucleic acid molecules encoding the disclosed polypeptides. In some embodiments, the nucleic acid molecule includes a nucleic acid sequence at least 70% identical (for example at least 80%, 90% or 95% identical) to the human nucleic acid sequence set forth as SEQ ID NO: 37. Alternatively, the nucleic acid sequence is at least 80% or 90% (for example at least 95% or 98%) identical to the murine sequence SEQ ID NO: 38 or zebrafish sequence SEQ ID NO: 39.

The nucleic acid sequence may be operably linked to a heterologous promoter, for example a promoter having the sequence shown in SEQ ID NO: 11 or SEQ ID NO: 12. The nucleic acid molecule may also be included in a vector, and host cells are disclosed that are transformed with the vector. Examples of such host cells are a plant cell, an animal cell, or a prokaryotic cell.

Also provided herein is an isolated nucleic acid molecule that hybridizes under conditions of low stringency to a target nucleic acid molecule selected from the group consisting of nucleotides 1-42 of SEQ ID NO: 37, SEQ ID NO: 38, and SEQ ID NO: 39, wherein the isolated nucleic acid molecule is at least 15 nucleotides in length. In more particular embodiments, the isolated nucleic acid molecule hybridizes under conditions of high stringency to the target nucleic acid molecule, for example a target nucleic acid molecule that encodes a RFX4_v3 polypeptide (such as the human SEQ ID NO: 8, the murine SEQ ID NO: 6, or the zebrafish SEQ ID NO: 10). This isolated nucleic acid sequence can be incorporated into a vector, and introduced into a host cell.

The RFX4_v3 polypeptide inhibits the phenotypic expression of congenital hydrocephalus, and has the ability to bind to RFX4_v3 specific antibodies (such as antibodies that distinguish RFX4_v1 and RFX4_v2 from RFX4_v3). In particular embodiments, the polypeptide includes the 14 consecutive N-terminal amino acid residues of SEQ ID NO: 8, SEQ ID NO: 6, or SEQ ID NO: 10, which are not found in RFX4_v1 or v2.

Also disclosed are methods for producing a variant of a RFX4_v3 polypeptide, by mutagenizing the wild-type nucleic acid sequence of SEQ ID NO: 37, SEQ ID NO: 38, or SEQ ID NO: 39; and screening the variant for a RFX4_v3 activity.

Compositions are also provided that include a nucleic acid molecule that inhibits the binding of the first 42 nucleotides of SEQ ID NO: 37, SEQ ID NO: 38, or SEQ ID NO: 39 to its complementary sequence. For example, the nucleic acid molecule is a polynucleotide sequence comprising at least fifteen nucleotides capable of hybridizing under stringent conditions to nucleotides 1-42 of SEQ ID NO: 37.

Methods are also disclosed for detecting a nucleic acid molecule in a biological sample, wherein the nucleic acid molecule encodes a RFX4_v3 polypeptide, by hybridizing a polynucleotide to the nucleic acid molecule to produce a hybridization complex, wherein the polynucleotide hybridizes to nucleotides 1-42 of SEQ ID NO: 37, SEQ ID NO: 38, or SEQ ID NO: 39, and detecting the hybridization complex. The hybridization complex indicates the presence of a polynucleotide encoding RFX4_v3 in the biological sample. In particular embodiments, the polynucleotide hybridizes to the human sequence, SEQ ID NO: 37. The nucleic acid molecule in the biological sample may be amplified prior to hybridizing with the polynucleotide.

Methods are also provided for identifying a subject at risk of developing RFX4 v3 linked hydrocephalus, by detecting in the subject an abnormality in a RFX4 v3 polypeptide or in a RFX4 v3 nucleotide sequence that alters expression of the RFX4 v3. For example, the abnormality may be detected by detecting a mutation in a nucleic acid sequence that encodes RFX4 v3, wherein the mutation is associated with RFX4 v3 linked hydrocephalus. In one example, the abnormality is detected by performing a hybridization analysis with a nucleic acid probe that detects the mutation in the RFX4 v3 nucleic acid sequence. For example, the method identifies an individual carrying a mutated RFX4_v3 allele, by providing from a subject a nucleic acid molecule that includes a RFX4_v3 allele. A mutation is then detected in the RFX4_v3 allele that results in phenotypic expression of congenital hydrocephalus.

In alternative embodiments, the abnormality is detected in the RFX4_v3 polypeptide. For example, a reduced expression of the RFX4 v3 polypeptide is detected, or a mutation is detected in RFX4_v3 that results in phenotypic expression of congenital hydrocephalus. In certain examples the mutations are detected with an antibody (such as a monoclonal antibody) that specifically binds to the RFX4_v3 polypeptide.

To perform these detection methods, a biological sample is obtained from the subject, in which the abnormality in the RFX4_v3 polypeptide or in the RFX4_v3 nucleotide sequence is detected. Specific examples of the biological sample include blood, amniotic fluid, plasma, a biopsy specimen, or cerebral spinal fluid.

A kit may also be used for determining if a subject is a carrier of a mutated RFX4_v3 gene that is associated with congenital hydrocephalus. Such a kit may include a reagent that specifically detects a mutation in a RFX4_v3 allele, accompanied by instructions for determining whether the subject is at increased risk of expressing congenital hydrocephalus if the reagent specifically detects the mutation. Specific examples of the detection reagent are a nucleic acid probe that hybridizes under stringent conditions to the nucleic acid sequence of SEQ ID NO: 37, SEQ ID NO: 38 or SEQ ID NO: 39, or an antibody that specifically binds the protein expressed by the RFX4_v3 allele.

Antibodies specific for an RFX4_v3 polypeptide may be obtained by injecting an animal with RFX4_v3 polypeptides or an immunogenic portion thereof, and preparing a hybridoma that expresses the monoclonal antibody. The RFX4_v3 specific antibody may be used for detection of RFX4_v3 polypeptides, or as a therapeutic agent.

This disclosure also provides a transgenic mouse having somatic and germ cells that include a disrupted endogenous RFX4_v3 gene, wherein the disruption is sufficient to produce an increased susceptibility to developing congenital hydrocephalus. The disrupted gene is, for example, introduced into an ancestor of the mouse at an embryonic stage. In certain embodiments the mouse, if homozygous for the disrupted gene, does not reproduce. A particular example of the disruption is an insertion within the RFX4_v3 gene, or a deletion or substitution within the RFX4_v3 gene.

Also disclosed herein are methods of making a non-human transgenic animal with a knockout for the RFX4_v3 gene, by disrupting an RFX4_v3 transcript, the disruption being sufficient to produce hydrocephalus in the transgenic animal, such as a mouse. Disrupting the RFX4_v3 transcript may include, for example, deleting or substituting any portion of the RFX4_v3 transcript, inserting an exogenous gene into the RFX4_v3 transcript, or any combination thereof. The transgenic mice may be crossed with each other to produce other transgenic animals having a similar phenotype.

Compounds may be screened for the ability to alter RFX4_v3 activity, by providing a first polypeptide sequence comprising at least a portion of RFX4_v3, a second polypeptide sequence comprising at least a portion of a protein known to interact with RFX4_v3, and one or more test compounds. The polypeptide sequences are combined with each other and exposed to one or more test compounds under conditions such that the first polypeptide sequence, the second polypeptide sequence, and the test compound interact. The presence or absence of an interaction between the polypeptide sequences is then determined to detect a test compound that alters RFX4_v3 activity.

The present disclosure also provides a composition, such as a pharmaceutical composition, that includes the polypeptide. For example, the composition is a therapeutic composition that includes a therapeutically effective amount of the polypeptide. This disclosure also enables the treatment of congenital hydrocephalus, for example by administering a pharmaceutical composition that includes a therapeutically effective amount of an RFX4_v3 nucleic acid, an RFX4_v3 polypeptide, or a therapeutically effective variant or portion of either. Hydrocephalus can also be treated by administering to the subject a therapeutically effective amount of an agent that increases presence of a RFX4_v3 polypeptide in the brain of the subject. Examples of this therapeutic approach are administering exogenous RFX4_v3 polypeptide to the subject, increasing expression of RFX4_v3 polypeptide in the subject, or introducing into the subject a vector that expresses the RFX4_v3 polypeptide in the brain of the subject.

The foregoing and other features and advantages will become more apparent from the following detailed description of a several embodiments.

BRIEF DESCRIPTION OF THE FIGURES

FIG. 1 shows the alignment of mouse RFX4_v3 sequences (Query; SEQ ID NO: 40) with residues 315187 to 314965 of human chromosome 12 genomic clone NT_009720 (Sbjct; SEQ ID NO: 36).

FIG. 2 shows a schematic representation of 200 kb of human genomic sequence from NT_009720.8, shown in reverse complement orientation, and the position within this sequence of the exons that comprise the three indicated RFX4 transcripts. At the top of the figure is shown the transcript corresponding to RFX4_v2 (accession number NM_002920). Exon 1 in this transcript is unique to this transcript; exons 2-5 are shared with the novel RFX4_v3 transcript described herein; exons 6-15A are shared with the RFX4_v3 transcript as well as the transcript RFX4_v1; and exon 15B is apparently unique to this transcript, and contains a polyadenylation sequence and presumably a polyA tail as indicated by the wavy line. The location of these exons on the genomic sequence are indicated. Below the genomic sequence is represented the transcript RFX4_v1. It contains a unique exon 1; exons 2-11 shared with both RFX4_v2 and RFX4_v3; and exons 12-14 shared only with RFX4_v3. The RFX4_v3 transcript contains a unique exon 1; exons 2-5 shared only with RFX4_v2; exons 6-15 shared with both RFX4_v1 and RFX4_v2; and exons 16-18 shared only with RFX4_v1. The site of transgene insertion is indicated in the genomic clone by the black X in the intron between exons 13 and 14 of RFX4_v1; its position between exons 17 and 18 of RFX4_v3 is also indicated. The portions of the RFX4_v3 transcript coding for the 737 amino acid human RFX4_v3 protein are indicated, as is the protein's DNA binding domain (DBD).

FIG. 3 shows the nucleic acid sequence alignment of human and mouse proximal promoters for RFX4_v3 (residues 3794-4000 of SEQ ID NO: 11 and residues 1-207 of SEQ ID NO: 12, respectively).

FIG. 4 shows the amino acid sequence alignment of human, mouse and zebrafish RFX4_v3 at the amino terminal end (residues 1-178 of SEQ ID NO: 8, residues 1-180 of SEQ ID NO: 6, and residues 1-158 of SEQ ID NO: 10, respectively).

FIG. 5 shows the amino acid sequence alignment of human and murine RFX4_v3 (SEQ ID NOs: 8 and 6, respectively).

FIG. 6 shows a schematic alignment of mouse, human and zebrafish RFX4_v3 amino acid sequences (SEQ ID NOs: 8, 6 and 10, respectively). The predicted amino acid sequences from these three RFX4_v3 orthologues were aligned using ClustalW. The position of the characteristic RFX DNA binding domain (DBD) is indicated by the box; other boxes contain the B and C boxes and the dimerization domain (DD). The shaded first 14 amino acids labeled exon 1 were unique to RFX4_v3 (human); the next unshaded sequences represent exons 2-5 and are identical to sequences from RFX4_v2; the next shaded sequences represent exons 6-15 and are identical to sequences from both RFX4_v1 and RFX4_v2; and the next unshaded sequences represent exons 16-18 and are identical to sequences in RFX4_v1. Asterisks indicate amino acid identity; double dots indicate a high degree of amino acid similarity; and single dots indicate less similarity.

FIG. 7A shows two mice in lateral (top) and frontal (bottom) view at about two months of age, showing the characteristic domed head and lateral displacement of the ears in the transgenic (TG) mouse compared to its wild-type (WT) littermate. FIG. 7B shows parasagittal sections, stained with hematoxylin and eosin, of brains from four littermate mice, three TG and one WT, at about seven weeks of age. The marked dilatation of the lateral ventricles (LV) is obvious in the TG mice; however, there is no evidence for dilatation of the fourth ventricles (arrows). Bar=1 mm.

FIG. 9A shows coronal sections in a rostral (R) to caudal (C) direction from P0.5 WT and TO littermates stained with hematoxylin and eosin, demonstrating the apparent absence of the SCO in the TG mouse. FIG. 9B shows similar sections stained with an antibody to Reissner's fibers. Note the near-absence of antibody staining in the TG section (top) compared to the WT section (bottom).

Figure 9:
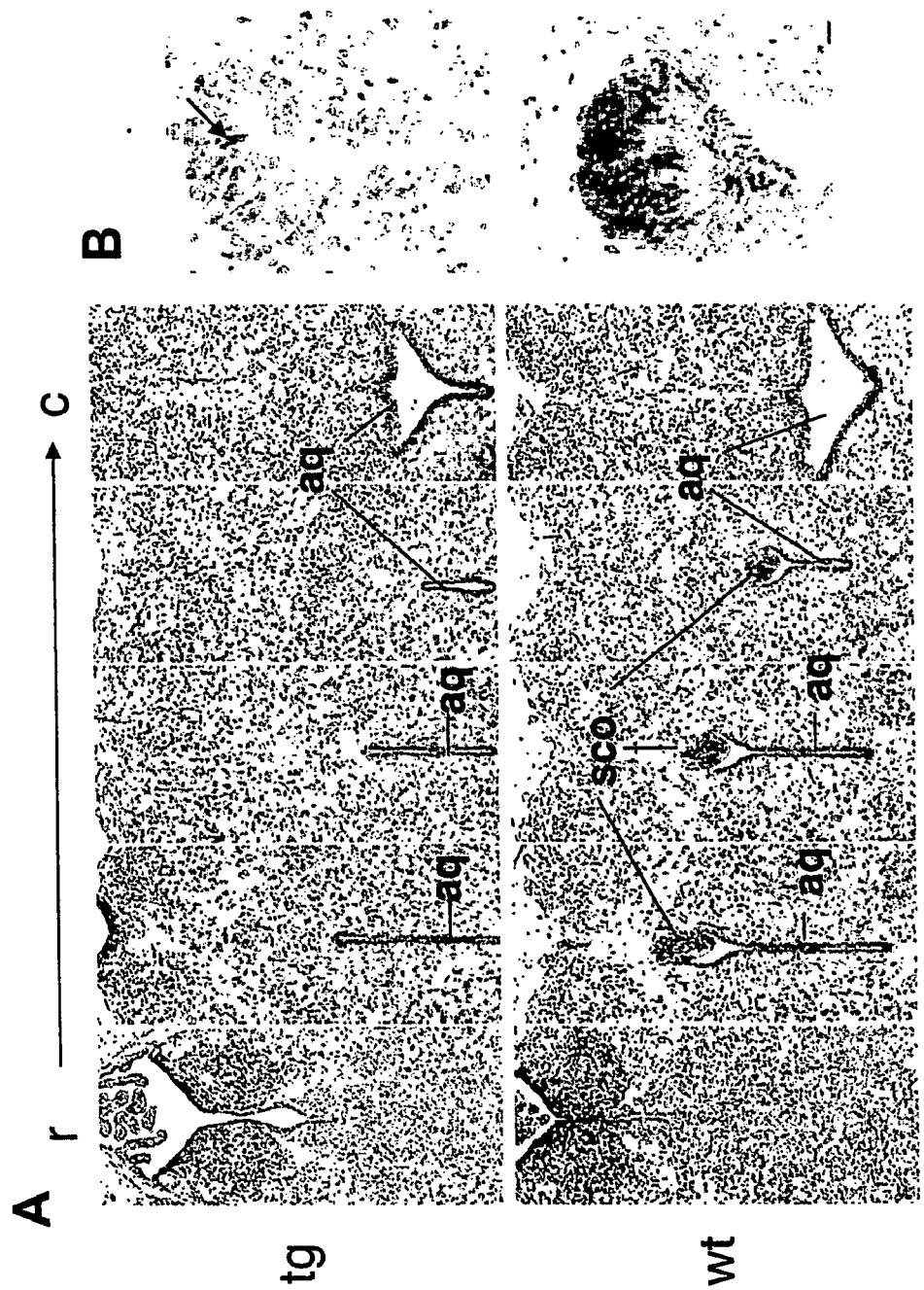
FIG. 9 is a set of digital images showing the aqueduct of Sylvius and SCO in WT and TG mice.

The arrow in the top section indicates a small amount of antibody staining in one section from the KO mouse, indicating the presence of the Reissner's fiber antigen. The counterstain was hematoxylin; the bar in the bottom section in FIG. 9B represents 50 μm, and the top section was further magnified 2.5 times.

Figure 10:
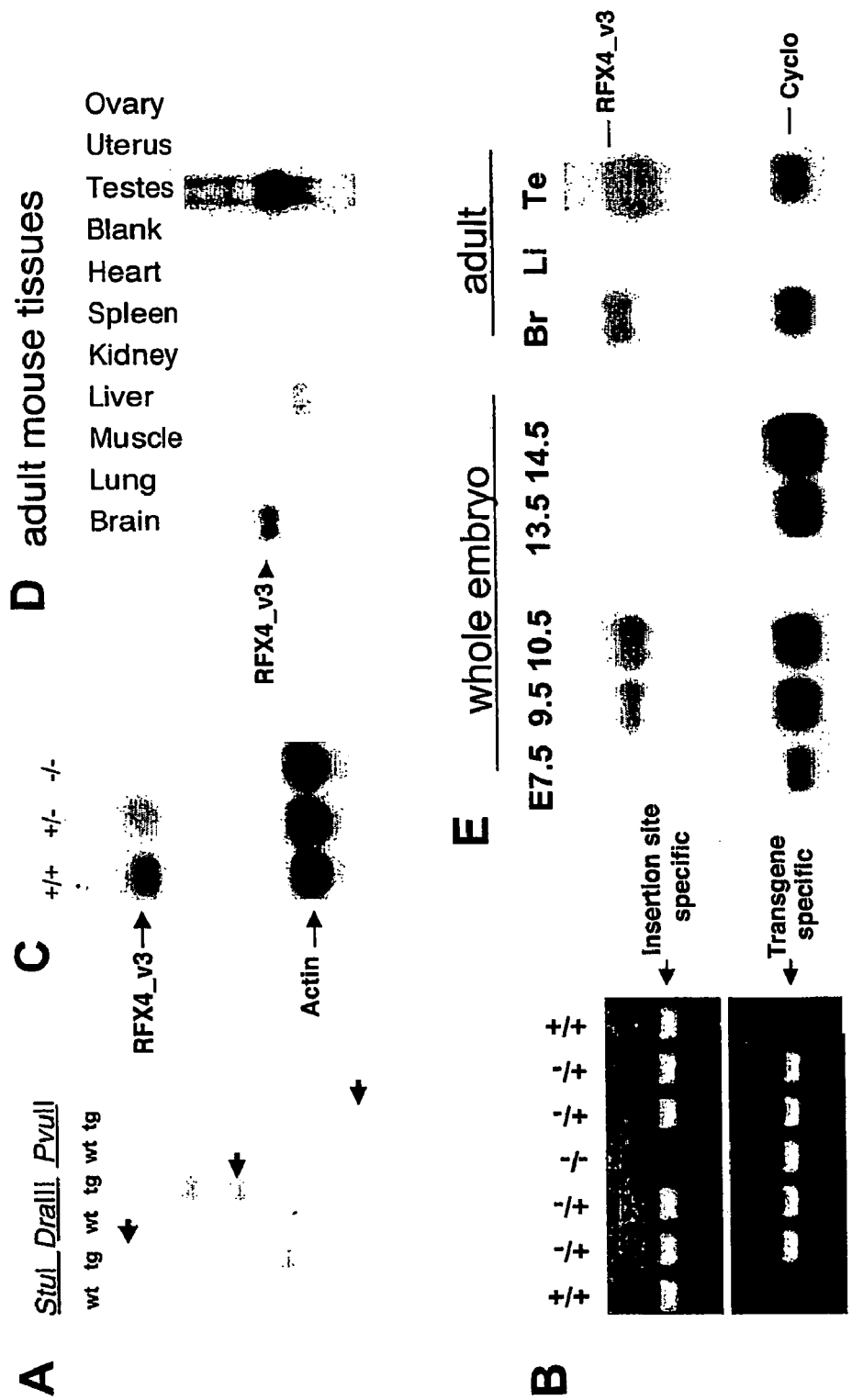

FIG. 10 is a set of digital images identifying the transgene insertion site. FIG. 10A shows a Southern blot of genomic DNA from WT and TG mice, digested with the three restriction enzymes indicated and probed with a 3'-insertion site-specific probe. The arrows indicate the three single, novel bands hybridizing to the probe in the DNA from the TG mice, indicating the likelihood of a single transgene insertion site. FIG. 10B shows a PCR-based analysis of genomic DNA from one litter of interbred TG mice, indicating the PCR products that were specific for the presence of the transgene (Transgene-specific) and those that were specific for the endogenous sequence that was interrupted by the transgene (Insertion site-specific). The transgene specific primers were 5'-AGCCAGTAATAAGAACTGCAGA-3' (SEQ ID NO: 29) and 5'-GGCACTCTTAGCAAACCTCAGG-3' (SEQ ID NO: 30), which correspond to bp 264-285 of the human cytochrome P450 cDNA clone accession number NM_000775.2 and bp 5225-5246 of the mouse α-myosin heavy chain promoter clone accession number MMU71441, respectively. The insertion site specific primers were 5'-CATG-GAAAGGGCAGAGTGAGC-3' (SEQ ID NO: 31) and 5'-GGCCATTGTCACCACTCGTAA-3' (SEQ ID NO: 32), which correspond to bp 732-752 and bp 323-343 of mouse trace archive sequence gnl|ti|91911671, respectively. In both cases, the results were confirmed by PCR using different pairs of primers. The DNA is characterized as +/+, +/− and −/− by the presence of the interrupted allele. FIG. 10C shows a northern blot of total brain RNA from newborn mice of the +/+, +/− and −/− genotypes. This blot was probed with a mouse EST clone that was 94% identical over 284 bases to a region corresponding to the 3'-end of the human testis-specific RFX4 transcript H10145. The only visible transcript was of approximately 4 kb (RFX4_v3); this was decreased in expression in the +/− sample, and undetectable in the −/− sample. Longer exposure of the blot did not reveal the presence of any truncated mRNA species in the +/− and −/− lanes. The same blot was hybridized to an actin cDNA (lower panel), and demonstrates roughly equivalent loading of the three RNA samples. In D is shown the hybridization of the same probe to adult mouse tissues, revealing an approximately 4 kb transcript in brain (RFX4_v3), a 3.7 kb transcript in testis, and a still smaller transcript in liver. In E is shown the pattern of developmental expression of the 4 kb transcript, which was undetectable in whole embryos at E7.5, highly expressed in whole embryos at E9.5 and 10.5, and less well expressed at E13.5 and 14.5. The brain, liver and testis lanes from D are juxtaposed in E to illustrate the difference in size between the brain (RFX4_v3), liver and testis transcripts, and the size identity of the adult brain transcript and the embryonic transcript. Also shown is the expression of a control mRNA for cyclophillin (Cyclo.)

Figure 11:
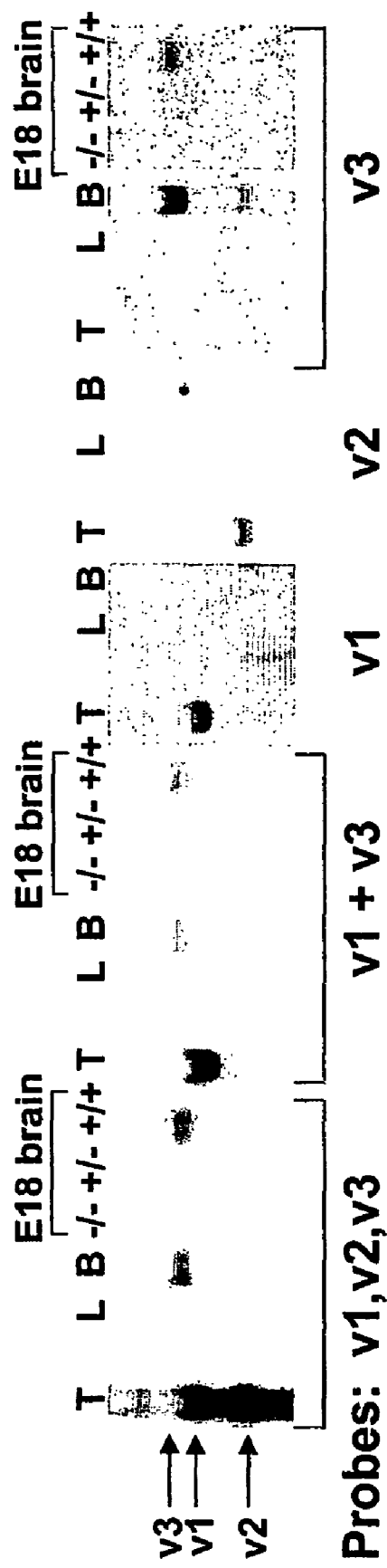

FIG. 11 is a digital image of a Northern analysis of RFX4 transcript expression using transcript-specific probes. cDNA probes corresponding to multiple or single RFX4 transcript variants, as indicated on the bottom of the figure, were used to probe northern blots containing total cellular RNA from adult testes (T), liver (L) and brain (B), or from brains of E18 mice of the +/+, +/− and −/− genotypes, as indicated. The blots were aligned to demonstrate the positions of the three hybridizing RFX4 species v1, v2 and v3 (arrows), as well as an uncharacterized transcript seen in adult mouse liver. There was no detectable hybridization of the specific v1 and v2 probes to the E18 brain RNA of any genotype.

Figure 12:
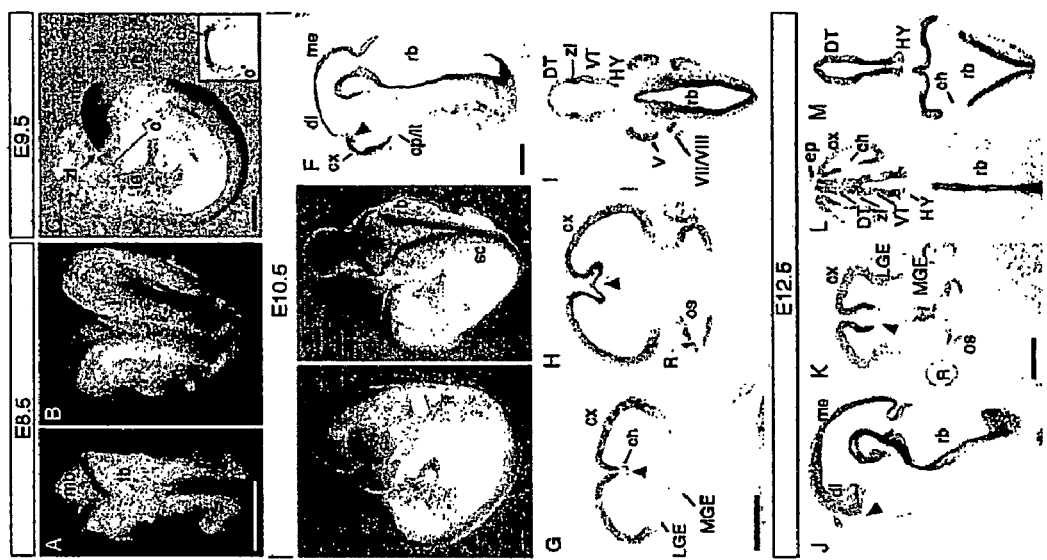

FIG. 12 is a set of digital images showing the developmental expression of RFX4_v3. FIGS. 12A-E are digital images of wholemount embryos at the indicated embryonic days (E) in which the RFX4_v3 transcript is indicated by the blue digoxigenin staining. For FIGS. 12A and B, the abbreviations are: mb, midbrain; fb, forebrain; hb, hindbrain. In FIG. 12C, the wholemount suggests minimal staining rostral of the zona limitans (zl); however, a section through the plane indicated as C' shows staining of the dorsal cortex (cx). Other abbreviations in FIG. 12C are: te, telencephalon; me, mesencephalon; rb, rhombencephalon; sc, spinal cord. FIGS. 12D and E are digital images of wholemounts at E10.5, whereas FIG. 12F is a digital image of a midline sagittal section, and FIGS. 12G-I are digital images of coronal sections, through similar embryos. New abbreviations in FIGS. 12D-I are: di, diencephalon; cb, cerebellum; cp/lt, commissural plate/lamina terminalis; LGE, lateral ganglionic eminence; MGE, median ganglionic eminence; ch, choroid plexus; R, retina; os, optic stalk; DT, dorsal thalamus; VT, ventral thalamus; HY, hypothalamus; V, trigeminal ganglion; VII/VIII, facial/vestibular gangion. The arrowheads in FIGS. 12F-H indicate the lost expression in the telencephalic dorsal midline at E10.5. J-M indicate one sagittal (J) and three caudal to rostral coronal sections through the head at E12.5. Note the lack of staining in the telencephalic dorsal midline (arrowheads in J, K), in the epiphysis (ep) in L, and in the fourth ventricle choroid plexus (ch) in M. Scale bars for (A-M), 500 µm.

Figure 13:
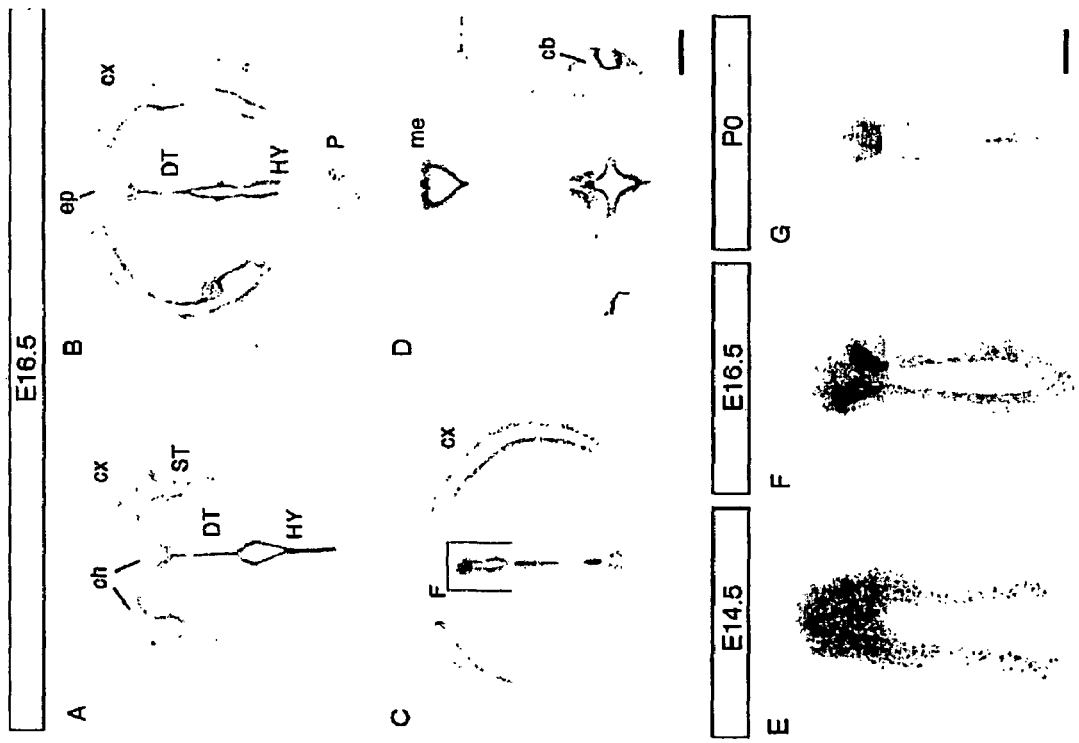

FIG. 13 is a set of digital images showing RFX4_v3 in situ staining in the region of the developing SCO. FIGS. 13A-D indicate progressively rostral to caudal sections through the brain of a normal embryo at E16.5. Abbreviations are the same as in the legend to FIG. 12 except for me (mesencephalon), cb (cerebellum), and P (pituitary). The box labeled F in section C contains the SCO and the aqueduct of Sylvius; this is shown enlarged in F at E16.5. The same region is shown at E14.5 (E) and at the time of birth (P0) (G). Note the high level expression of the RFX4_v3 transcript in the region of the developing SCO in E, and in the SCO itself in F and G. Scale bars for (A-D), 500 µm; (E-G), 100 µm.

Figure 14:
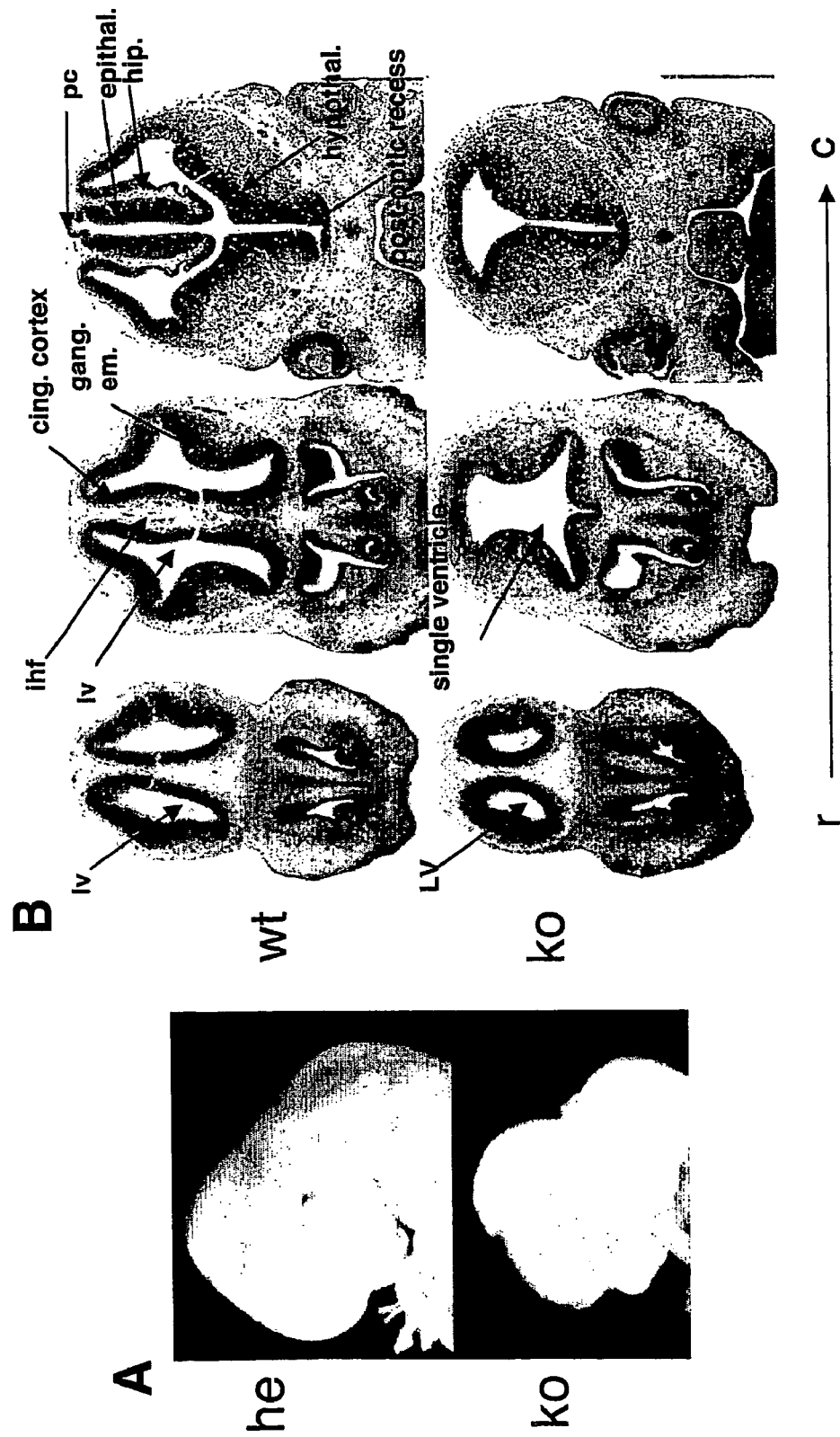

FIG. 14 is a set of digital images showing the head morphology from –/– mice at E12.5. FIG. 14A shows heads from two E12.5 littermates after fixation, one hemizygous (HE) and one KO (–/–) as indicated. Note the near normal appearance of the eyes and the facial structures, but the clearly abnormal doming of the skulls and the smaller heads of the –/– littermate. FIG. 14B shows coronal sections from WT (top row) and KO (bottow row) littermate mice at E12.5, stained with hematoxylin and eosin. In the most rostral (R) sections (left panels), the brains appear somewhat similar, showing both lateral ventricles (LV) and apparently normal midline structures, although the brains were somewhat smaller in the KO mice. In more caudal (FIG. 14C) sections (middle two panels), however, there was a striking loss of midline structures and the formation of a single central ventricle. In still more caudal sections (right panels), taken at the level of the retinas, there were continued striking abnormalities and loss of essentially all dorsal midline structures. Other abbreviations: IHF, interhemispheric fissure; Cing. cortex, cingulate cortex; Gang. em., ganglionic eminence; PC, posterior commissure; Epithal., epithalamus; Hip., hippocampus; Hypothal., hypothalamus.

Figure 15:
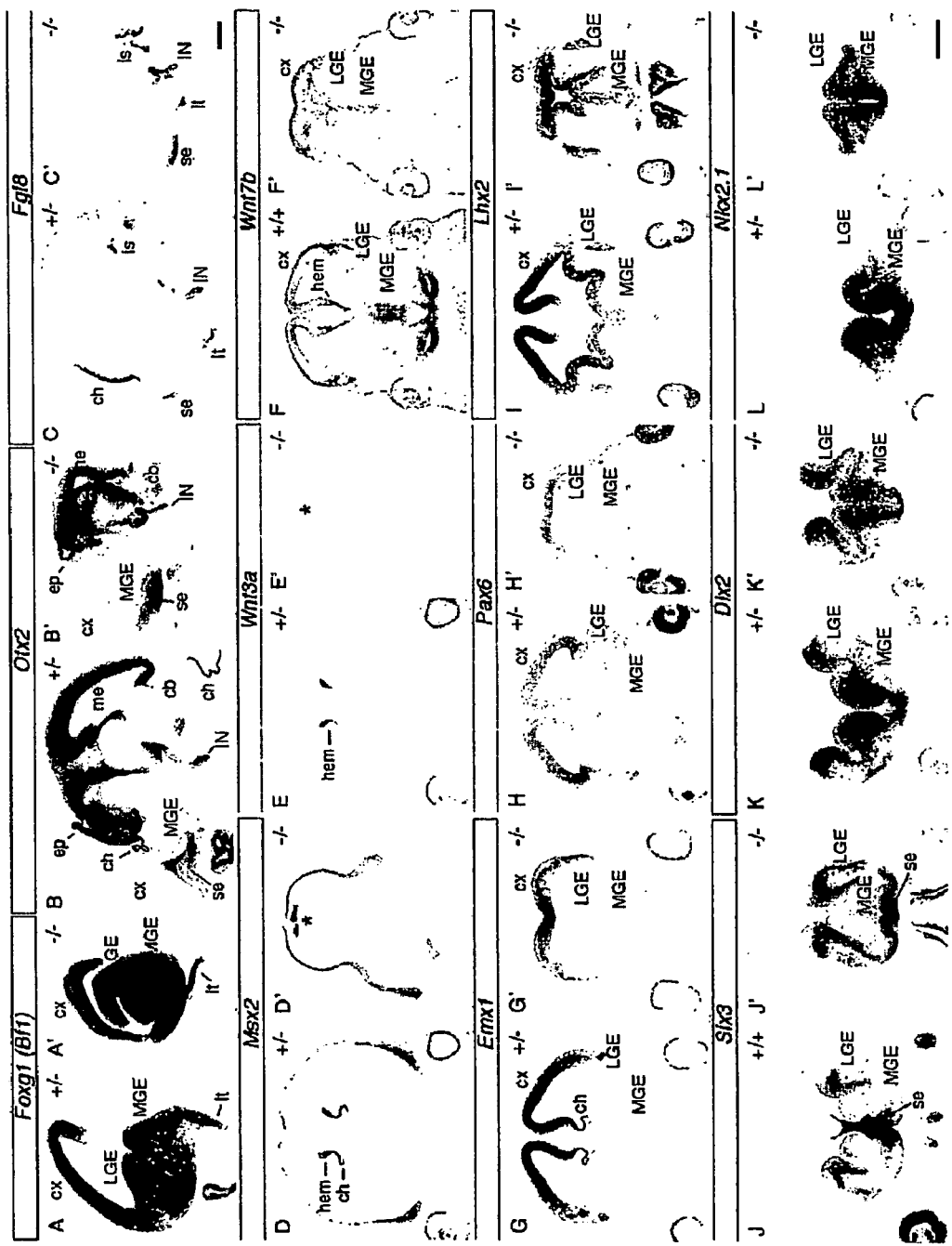

FIG. 15 is a set of digital images showing expression of molecular markers in WT and littermate KO mice at E12.5. Shown are the in situ hybridization staining patterns of sagittal (FIGS. 15A-C) and coronal sections through WT (+/–or +/+) and KO (–/–) heads at E12.5. The digoxigenin staining indicates the presence of the specific transcript being evaluated. New abbreviations not found in the legends of FIGS. 12-14 include: se, septum; IN, infundibulum; It, lamina terminalis; is, istmus; hem (cortical hem). Note that Fgf8 expression is maintained in the istmus (is), infundibulum (IN), lamina terminalis (it) and septum (se), but is lost in the choroid plexus (ch) of the forebrain (C and C'). The asterisks in FIGS. D' and E' indicate the decrease in Msx2 expression (D, D') and the lack of Wnt3a expression (E, E') in the dorsal midline of the KO embryos. Scale bars for (A-I), 500 µm.

BRIEF DESCRIPTION OF THE SEQUENCE LISTINGS

The nucleic acid and protein sequences listed in the accompanying sequence listing is shown using standard letter abbreviations for nucleotide bases, and triple letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleic acid sequence of human RFX4_v2 (GenBank Accession No. NM_002920).

SEQ ID NO: 2 shows the amino acid sequence of human RFX4_v2 (GenBank Accession No.: NP_002911.2).

SEQ ID NO: 3 shows the nucleic acid sequence of human RFX4_v1 (GenBank Accession No. AF332192).

SEQ ID NO: 4 shows the amino acid sequence of human RFX4_v1 (GenBank Accession No.: AAK17191.1).

SEQ ID NO: 5 shows a nucleic acid sequence of murine RFX4_v3 (GenBank Accession No. AY102010), including untranslated sequences.

SEQ ID NO: 6 shows the amino acid sequence of murine RFX4_v3.

SEQ ID NO: 7 shows a nucleic acid sequence of human RFX4_v3 (GenBank Accession No. AY102009), including untranslated sequences.

SEQ ID NO: 8 shows the amino acid sequence of human RFX4_v3.

SEQ ID NO: 9 shows a nucleic acid sequence of zebrafish RFX4_v3 (GenBank Accession No. AY102011), including untranslated sequences.

SEQ ID NO: 10 shows the amino acid sequence of zebrafish RFX4_v3.

SEQ ID NO: 11 shows the nucleic acid sequence of the proximal promoter of human RFX4_v3.

SEQ ID NO: 12 shows the nucleic acid sequence of the proximal promoter of murine RFX4_v3.

SEQ ID NO: 13 shows the N-terminal amino acid sequence of zebrafish RFX4_v3.

SEQ ID NO: 14 shows a nucleic acid sequence of human RFX4_v1 (GenBank Accession No. NM 032491), including untranslated sequences.

SEQ ID NO: 15 shows the amino acid sequence of human RFX4_v1 (GenBank Accession No. NP_115880).

SEQ ID NO: 16 shows the first forward primer for RFX4_v1.

SEQ ID NO: 17 shows the first reverse primer for RFX4_v1.

SEQ ID NO: 18 shows the shows the second forward primer for RFX4_v1.

SEQ ID NO: 19 shows the shows the second reverse primer for RFX4_v1.

SEQ ID NO: 20 shows the forward primer for mouse RFX4_v3.

SEQ ID NO: 21 shows the reverse primer for mouse RFX4_v3.

SEQ ID NO: 22 shows the first forward primer for human RFX4_v2.

SEQ ID NO: 23 shows the reverse primer for human RFX4_v2.

SEQ ID NO: 24 shows the second forward primer for human RFX4_v2.

SEQ ID NO: 25 shows the first forward nested BSIRFRX4-specific primer.

SEQ ID NO: 26 shows the first reverse nested BSIRFRX4-specific primer.

SEQ ID NO: 27 shows the second forward nested BSIR-FRX4-specific primer.

SEQ ID NO: 28 shows the second reverse nested BSIR-FRX4-specific primer.

SEQ ID NO: 29 shows the transgene-specific forward primer.

SEQ ID NO: 30 shows the transgene-specific reverse primer.

SEQ ID NO: 31 shows the insertion site specific forward primer.

SEQ ID NO: 32 shows the insertion site specific reverse primer.

SEQ ID NO: 33 shows amino acids 1-14 from the N-terminus of human RFX4_v3.

SEQ ID NO: 34 shows amino acids 1-14 from the N-terminus of murine RFX4_v3.

SEQ ID NO: 35 shows amino acids 1-14 from the N-terminus of zebrafish RFX4_v3.

SEQ ID NO: 36 shows a portion of human chromosome 12 genomic clone NT-009720.

SEQ ID NO: 37 shows the nucleic acid coding sequence that encodes the human RXF4_v3 amino acid sequence shown in SEQ ID NO: 8.

SEQ ID NO: 38 shows the nucleic acid coding sequence that encodes the murine RFX4_v3 amino acid sequence shown in SEQ ID NO: 6.

SEQ ID NO: 39 shows the nucleic acid coding sequence that encodes the zebrafish RFX4_v3 amino acid sequence shown in SEQ ID NO: 10.

TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments, the following explanations of specific terms are provided:

The term "gene" refers to a nucleic acid (e.g., DNA) sequence that comprises coding sequences necessary for the production of a polypeptide or precursor (e.g., RFX4_v3). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb on either end such that the gene corresponds to the length of the full-length mRNA. The sequences that are located 5' of the coding region and which are present in the mRNA are referred to as 5' untranslated sequences. The sequences that are located 3' or downstream of the coding region and that are present in the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (mRNA); introns may contain regulatory elements such as enhancers. Introns are removed or "spliced out" from the nuclear or primary transcript; introns, therefore, are absent in the messenger RNA (mRNA) transcript. The mRNA functions during translation to specify the sequence or order of amino acids in a nascent polypeptide.

In particular, the term "RFX4_v3 gene" refers to the full-length RFX4_v3 nucleotide sequence (e.g., nucleotides 2,829,445 to 2,991,076 of Accession no. NT_035235, Human Chromosome 12 Genomic Contig; or nucleotides 2,737,642 to 2,889,558 of Accession no. NT_039498, Mouse Chromosome 10 Genomic Contig). However, it is also intended that the term encompass fragments of the RFX4_v3 sequence, as well as other domains within the full-length RFX4_v3 nucleotide sequence. Furthermore, the terms "RFX4_v3 nucleotide sequence" or "RFX4_v3 polynucleotide sequence" encompasses DNA, cDNA, and RNA (e.g. mRNA) sequences.

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

As used herein, a RFX4_v3 polypeptide is an amino acid sequence, for example, SEQ ID NO: 6, SEQ ID NO: 8, or SEQ ID NO: 10, or a variant amino acid sequence with substantial sequence identity to SEQ ID NO: 6, SEQ ID NO: 8, or SEQ ID NO: 10, for example 70%, 75%, 80%, 85%, 90%, 95%, or 98% sequence identity. In some embodiments, the RFX4_v3 polypeptide retains at least one RFX4_v3 activity. As used herein, a RFX4_v3 activity is an activity that promotes the development of the brain's ventricular system, the absence of which activity is demonstrated by the development of hydrocephalus. In one embodiment, the RFX4_v3 activity is the inhibition of the phenotypic expression of congenital hydrocephalus. In another example, the RFX4_v3 activity is the ability to bind to RFX4_v3 specific antibodies. Screening for a RFX4_v3 activity can be accomplished by, for example, screening for the morphological or behavioral signs of hydrocephalus, or screening for binding to RFX4_v3 antibodies (see below).

As used herein, "abnormal" refers to a difference from wild-type, particularly a difference that results in expression of a protein that is associated with a disease condition. For example, "abnormal expression" refers to a perturbation in the level at which a particular protein is expressed, for example an increase or decrese in expression as compared to a wild-type level of expression. An "abnormal RFX4 v3 polypeptide" refers to such a difference in either the protein itself the level or its expression, or a difference in the nucleic acid that encodes the protein and results in the abnormality.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "heterozygous" refers to having different alleles at a corresponding chromosomal locus.

As used herein, the term "homozygous" refers to having similar alleles at a corresponding chromosomal locus.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

Those of skill in the art know that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g. the presence or absence of formamide, dextran sulfate, polyethylene glycol) are considered and the hybridization solution may be varied to generate conditions of low stringency hybridization different from, but equivalent to, the above listed conditions. In addition, those of skill in the art know conditions that promote hybridization under conditions of high stringency (e.g. increasing the temperature of the hybridization and/or wash steps, the use of formamide in the hybridization solution, etc.)

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, a specific binding agent is an agent that binds substantially only to a defined target. Thus a RFX4_v3-specific binding agent binds substantially only the RFX4_v3 RNA or DNA sequence, or the RFX4_v3 polypeptide. As used herein, the phrase RFX4_v3-specific binding agent includes anti- RFX4_v3 protein antibodies and other agents (such as nucleic acids) that bind substantially only to the RFX4_v3 nucleic acid sequence or polypeptide. As used herein, "specific binding" includes specific hybridization.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is affected by such factors as the degree of complementarity between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g. hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The following terms are used to describe the sequence relationships between two or more polynucleotides: "reference sequence," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math., 2: 482 [1981]) by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA, 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g. A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present disclosure (e.g., RFX4_v3).

As applied to polypeptides, the term "substantial identity" means that two peptide sequences, when optimally aligned, such as by the programs GAP or BESTFIT using default gap weights, share at least 70 percent sequence identity, at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "mutagenize" refers to any method of inducing a mutation in an RNA, DNA or amino acid sequence. Methods of mutagenization include, but are not limited to chemical mutagenization, for example using bromouracil, nitrous acid, nitrosoguanidine, methyl methanesulfonate, ethyl methanesulfonate, acridine orange, proflavin, or ethidium bromide, or by irradiation, for example ultraviolet irradiation.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present disclosure) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at which little or no variation is seen between members of the population (generally taken to be a locus at which the most common allele exceeds a frequency of 0.95 in the gene pool of the population).

As used herein, the term "polymorphism information" refers to the presence of absence of one or more polymorphisms (e.g., mutations) in a gene (e.g. the RFX4_v3 gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, "providing a polypeptide from a subject" includes providing any biological sample from the subject that includes a polynucleotide. Examples of suitable biological samples include samples of any type of tissue, for example brain, liver, lung, stomach, intestine, pancreas, bone, skin, spleen, kidney, ovary, testis, or connective tissue, or any body fluid, for example blood, serum, plasma, cerebral spinal fluid, tears, sweat, amniotic fluid, semen, urine, gastric and intestinal fluids, saliva, mucous, or sinovial fluid.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acids. Amplification techniques have been designed primarily for this sorting out.

An example of amplification is the polymerase chain reaction (see below). Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (D. L. Kacian et al., Proc. Natl. Acad. Sci. USA, 69:3038 [1972]). This amplification enzyme will not replicate other nucleic acid. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of 'target ' (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification, and isolation of particular gene sequences. It is contemplated that any probe used in the present disclosure will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present disclosure be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of K. B. Mullis U.S. Pat. Nos. 4,683,195, 4,683,202, and 4,965,188 that describe methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to nucleic acid sequences that are complementary to a specific target nucleic acid sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand. Regions of a nucleic acid sequences that are accessible to antisense molecules can be determined using available computer analysis methods.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding RFX4_v3 includes, by way of example, such nucleic acid in cells ordinarily expressing RFX4_v3 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to a fragment of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, ATC).

As used herein, the term "purified" or "to purify" or "purified," refers to molecules including, but not limited to nucleic or amino acid sequences, proteins, peptides, antibodies, or any organic molecule, that are removed from their natural environment or from a sample. For example, RFX4_v3 antibodies are purified by removal of contaminating non-immunoglobulin proteins; they are also purified by the removal of immunoglobulin that does not bind RFX4_v3. The removal of non-immunoglobulin proteins and/or the removal of immunoglobulins that do not bind RFX4_v3 result in an increase in the percent of RFX4_v3-reactive immunoglobulins in the sample. In another example, recombinant RFX4_v3 polypeptides are expressed in bacterial host cells and the polypeptides are purified by the removal of host cell proteins; the percent of recombinant RFX4_v3 polypeptides is thereby increased in the sample. In another example, an "isolated nucleic acid sequence" is therefore a purified nucleic acid sequence. "Substantially purified" molecules are at least 60% free, preferably at least 75% free, and more preferably at least 90% free from other components with which they are naturally associated.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from, a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g. bacterial cells such as E. coli, yeast cells, mammalian cells, avian cells, amphibian cells, plant cells, fish cells, and insect cells), whether located in vitro or in vivo. For example, host cells may be located in a transgenic animal. In some embodiments, a host cell is a plant cell, an animal cell, or a prokaryotic cell.

The term "reduced expression" and grammatical equivalents, refers to a lesser expression of a nucleic acid product in a sample than is found in wild type controls. Expression may be reduced, for example, by 10%, 25%, 50%, or more. One method by which reduced expression may be determined is by using levels of mRNA to indicate a reduced level of expression as compared to that typically observed in a given tissue in a control or non-transgenic animal. For example, the comparison may be made between a wild type mouse and a transgenic mouse that is +/–or –/– for RFX4_v3 expression as a result of targeted gene disruption (see Detailed Description, section VI). Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced RFX4_v3 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding RFX4_v3 (e.g., SEQ ID NO: 5) or fragments thereof may be employed as hybridization probes. In this case, the RFX4_v3 encoding polynucleotide sequences are typically employed in an aqueous solution containing salts (e.g., NaCl), detergents (e.g., SDS), and other components (e.g. Denhardt's solution, dry milk, salmon sperm DNA, etc.)

The term "test compound" refers to any chemical entity, pharmaceutical, drug, and the like that can be used to treat or inhibit the development of a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present disclosure. A "known therapeutic compound" refers to a therapeutic compound that has been shown (e.g. through animal trials or prior experience with administration to humans) to be effective in such treatment or prevention.

The term "sample" as used herein is used in its broadest sense to include all biological samples, and by way of example includes amniotic fluid and tissue specimens (such as brain biopsy or tissue sections). A sample suspected of containing a human chromosome or sequences associated with a human chromosome may comprise a cell, chromosomes isolated from a cell (e.g. a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject. In addition, subject also refers to the unborn progeny of the any animal, including, but not limited to humans, non-human primates, rodents, and the like.

GENERAL DESCRIPTION OF THE DISCLOSURE

The present disclosure relates to a novel splice variant of the Regulatory Factor X 4 (RFX4) member of the winged helix transcription factor family that is preferentially expressed in the developing brain. Members of the RFX family of winged-helix transcription factors are involved in the regulation of many cellular processes. This novel splice variant is designated RFX4 variant transcript 3, (RFX4_v3.) When one allele is defective, there is universal congenital hydrocephalus with aqueductal stenosis, probably secondary to agenesis of the subcommissural organ. This defect appears to be compatible with life, and in some cases normal fertility. This hydrocephalus exhibits an autosomal dominant inheritance pattern. When two alleles are defective, there is severe disruption of brain formation and prenatal or perinatal death.

While an understanding of the mechanism is not required to practice the present disclosure and the present disclosure is not limited to any particular mechanism, it is contemplated that the RFX4 transcript is responsible for dose-dependent brain phenotypes: hydrocephalus associated with hypoplasia or aplasia of the subcommissural organ in the heterozygote, and severe and lethal defects of telencephalon formation in the homozygote. The subcommissural organ appears to be highly susceptible to quantitative decreases in the expression of this transcript and thereby be a key regulator of early telencephalon development. Continued high levels of expression in the adult brain also suggest a key role after development.

In humans, this RFX4 transcript is composed of 18 exons from an approximately 200 kb region on human chromosome 12. Some of the exons are common to other RFX4 isoforms that are generally enriched in testis. However, the RFX4_v3 transcript is novel in that it contains a mixture of exons from two previously identified transcripts as well as a completely novel exon that encodes the amino terminus in the protein.

This transcript finds use as the basis for diagnostic tests for this type of familial congenital hydrocephalus, applied to prenatal samples such as amniotic fluid, or to parental DNA specimens for use in genetic counseling. Knowledge of a familial predisposition to congenital hydrocephalus aids family planning and genetic counseling decisions, and also permits prenatal diagnosis and early shunt placement to prevent death or neurological morbidity.

Diagnostic tests also find use for screening potentially heterozygous affected children, both prenatal and postnatal, and their heterozygous parents. In some embodiments, the diagnostic tests utilize cDNAs spanning either the complete transcript, partial transcript, splice site mutations, promoter abnormalities, or mutations in the key DNA binding domain.

DETAILED DESCRIPTION OF THE DISCLOSURE

The present disclosure relates to RFX4_v3 protein and nucleic acids encoding the RFX4_v3 protein. The present disclosure encompasses both native and recombinant wild-type forms of RFX4_v3, as well as mutant and variant forms, some of which possess altered characteristics relative to the wild-type RFX4_v3. The present disclosure also relates to methods of using RFX4_v3, including altered expression in transgenic organisms and expression in prokaryotes and cell culture systems. The present disclosure also encompasses methods for screening for drugs that inhibit or potentiate RFX4_v3 action. The present disclosure also relates to methods for screening for susceptibility to congenital hydrocephalus.

An embodiment of the present disclosure demonstrates that the disrupted expression of the novel isoform of the RFX4 transcript (RFX4_v3) is responsible for a dosage-dependent brain phenotype. Congenital hydrocephalus is associated with hypoplasia or absence of the subcommissural organ (SCO) in heterozygous mice, whereas severe and lethal defects of midline brain structure formation are found in homozygous mice missing both alleles of the RFX4_v3 gene. The present disclosure demonstrates that a quantitative decrease in the expression of the RFX4_v3 transcript is sufficient to interfere specifically with the development of the SCO, leading to effective stenosis of the aqueduct of Sylvius and congenital hydrocephalus. This partial RFX4_v3 deficiency is nonetheless compatible with post-natal life, and in some cases with successful fertility. In contrast, in alternate embodiments of the present disclosure, complete deficiency of this transcript leads to catastrophic failure of midline structure formation in early brain development and universal prenatal or perinatal death. The present disclosure identifies RFX4_v3 as a key, early regulator of midline brain structure development in the vertebrate animal. An embodiment of the disclosure demonstrates that the continued high-level expression of RFX4_v3 in the adult mouse brain also indicates a role after development.

The RFX family of winged-helix transcription factors is comprised of seven primary transcripts, each of which is thought to bind to the "X box" of gene promoters and thus regulate gene expression (Morotomi-Yano, et al, *J. Biol. Chem.*, 277:836-842 [2002]), herein incorporated by reference). The RFX proteins belong to the winged-helix subfamily of helix-turn-helix transcription factors, and are so named because they bind to "X-boxes." The RFX4 member of this family has been described as a testis-specific transcript whose downstream DNA targets were not known (Morotomi-Yano, et al., *J. Biol. Chem.*, 277:836-842 [2002]). In addition, an estrogen receptor related protein contains a portion of the putative RFX4 transcript, and other variants including portions of the RFX4 sequence are present in GenBank.

The X-box consensus sequence is 5'-GTNRCC(0-3N) RGYAAC-3', where N is any nucleotide, R is a purine and Y is a pyrimidine. Five RFX proteins have been described in man (RFX1-RFX5), all of which contain a highly conserved DNA binding domain near the amino terminus. A structure has been determined for the binding of this domain from RFX1 to an X-box sequence (Gajiwala et al., Nature, 403: 916-21 [2000]); this shows that the "wing" of this DNA binding domain is used to recognize DNA. Members of this family have been implicated in the transcriptional regulation of a number of important genes.

A partial sequence of a novel family member, termed RFX4, was initially identified by Dotzlaw et al. (Dotzlaw et al., *Mol. Endocrinol.*, 6:773-7785 [1992]) as part of a fusion cDNA in human breast cancers, in which the amino-terminal estrogen binding domain of the estrogen receptor was fused with the RFX DNA binding domain. More recently, two full-length RFX4 cDNAs have been described and categorized. The new RFX4_v3 variant described here is composed of novel exons as well as exons derived from one or both of these two earlier variants. As illustrated in FIG. 2, the RFX4_v3 cDNA is the largest of the three and is composed of a unique 5' exon of approximately 476 bp that encodes the first 14 amino acids of RFX4_v3; this is then followed by four exons shared only with RFX4_v2, then 10 exons shared with both RFX4_v1 and RFX4_v2, and finally three 3'-exons shared only with RFX4_v1.

An embodiment of the present disclosure shows that the novel RFX4_v3 transcript is highly expressed during early to mid-gestation in the mouse, during the critical periods of telencephalon formation. The novel RFX4_v3 transcript is also highly expressed in adult brain. In still further embodiments of the present disclosure, a 3'-probe used for northern analysis detected abundant expression of the RFX4_v1 transcript in testis, and still smaller transcripts in liver.

Abnormalities of the SCO have been associated with hydrocephalus in many studies (reviewed by Perez-Figares et al, Microsc. Res. Tech., 52:591-607 [2001]). It is contemplated that the SCO abnormalities preceding and causing the hydrocephalus are due to effective stenosis of the aqueduct of Sylvius. Therefore, it appears that the aplasia or hypoplasia of the SCO seen in the RFX4_v3 hemizygous mice is the cause of the congenital hydrocephalus, presumably by interfering with cerebrospinal fluid flow through the rostral part of the aqueduct.

I. RFX4_v3 Polynucleotides

The present disclosure arose from the discovery that an epoxygenase transgene had interrupted the RFX4_v3 gene. Genomic sequences flanking the transgene were identified using PCR based on 5' and 3' transgene sequences. At least two tandem copies of the 7.5 kb transgene in genomic DNA from the transgenic mice, indicated that the potential genomic interruption was at least 15 kb in size; Southern blot analysis using a transgene specific probe indicated that there was only one copy of this concatenated transgene in the mouse genome. Using the GENOMEWALKER technique with genomic DNA from the transgenic mice and transgene specific oligonucleotide primers, both the 5' and 3' flanking genomic sequences into which the transgene had been inserted were identified. When these sequences were compared to the mouse genomic sequences in the GenBank trace archives, the transgene insertion site was identified as between bp 528 and 529 in gnl|ti|13973384 and between bp 171 and 172 in gnl|ti|84074979. The 5' and 3' flanking sequences identified by the GENOMEWALKER technique were contiguous in the normal mouse genomic sequences in the trace archives, indicating that the transgene insertion was not accompanied by a genomic deletion, as has been seen in some recent examples of accidental transgenic insertional mutagenesis (Durkin, et al., Genomics, 73:20-7, [2001]; Overbeek, et al., Genesis, 30:26-35, [2001]). Southern analysis using a 3'-insertion site-specific probe demonstrated the presence of single novel bands in restriction enzyme-digested DNA from the transgenic mice, confirming a single transgene insertion site at this location.

The flanking sequences identified by the GENOMEWALKER approach were merged with available mouse genomic sequences from trace archives to form a small contig; no cDNAs or expressed sequence tags (ESTs) matched. Therefore, the assembled mouse contig was used to search the human genome sequences then available in GenBank, using BLAST. The mouse sequence was highly related (4e-28) to a human genomic sequence corresponding to a portion of human chromosome 12 (GenBank Accession No.: NT_009720.8). See FIG. 1 (entitled, "Alignment of mouse sequences with the human chromosome 12 genomic clone NT_009720"). When this small region of human genomic sequence was analyzed for expressed sequences, it did not match any expressed in GenBank. However, when a much larger amount of human genomic DNA from this locus was used to search for expressed sequences, genomic DNA within 200 kb of the human sequence corresponding to the transgene insertion site was found to contain all of the exons of two distinct cDNAs in GenBank that correspond to two forms of the human winged helix protein RFX4. One embodiment, RFX4 variant transcript 2 (RFX4_v2) is represented by GenBank Accession7.1 No. NM_002920 (SEQ ID NO: 1), corresponding to protein accession number NP_002911 (SEQ ID NO:2). The other embodiment, RFX4 variant transcript 1 (RFX4_v1) is represented by GenBank Accession No. NM 032491 (SEQ ID NO: 14) corresponding to protein accession number NP_115880 (SEQ ID NO: 15). RFX4_v1 is derived from GenBank Accession No. AF332192 (SEQ ID NO: 3), corresponding to protein accession number AAK17191 (SEQ ID NO: 4). See FIG. 2 (entitled, "The human RFX4_v3 locus"). According to these alignments, the site of the transgene insertion within the mouse genome was at a corresponding region within the human genome that would be within the intron between exons 13 and 14 of AF332192 (SEQ ID NO: 3) (or RFX4_v1) and would not have affected the exon arrangements of NM_002920 (SEQ ID NO:1) (or RFX4_v2).

Using PCR primers based on the inserted transgene and the neighboring endogenous mouse genomic DNA, the wild-type (+/+) and transgene-interrupted alleles (+/−) for one disrupted allele (heterozygous) ((−/−) for both alleles disrupted (homozygous)) were found to be readily distinguished in a litter of newborn mice from interbred transgenic mice.

To examine whether the transgene insertion interfered with the expression of a full-length mouse RFX4 transcript in brain, Northern blots from brains of neonatal (+/+), (+/−), and (−/−) were performed with a mouse brain EST cDNA clone (IMAGE # 763537, GenBank Accession Nos. AA285775 and AI462920) that was highly related (e-124 over 284 aligned bases) to the 3'-end of the human cDNA RFX4_v1 (SEQ ID NO: 14). Brains from the +/+mice expressed a prominent band of ~4 kb that is referred to as RFX4 variant transcript 3, (RFX4_v3). This revealed that the brains from the (+/−) heterozygous mice expressed approximately 50% of the normal transcript, whereas the brains from the (−/−) homozygous mice expressed no detectable transcript of this size. Probing the same blot with an actin cDNA demonstrated that gel loading was similar in the three lanes. Similar results were obtained in three separate experiments. There was no evidence for the expression of a truncated mRNA in the brain samples from either the +/-or −/− mice. These studies confirmed that an mRNA species of 4 kb that was recognized by a probe derived from putative mouse 3' RFX4_v1 sequences was decreased in amount in brains of the (+/−) heterozygous and absent in the brains (−/−) homozygous mice, indicating that the insertion of the transgene interfered with the expression of the putative brain RFX4_v3 transcript.

Using the same probe to examine the tissue-specific and developmental expression of this RFX4 transcript, high-level expression of a slightly smaller transcript in normal adult testis was found, and lower level expression of a considerably smaller transcript in liver. The largest species, which corresponds to the brain-specific transcript, was primarily found in whole embryos early in development. RFX4_v3 in the adult is highly expressed in the whole embryo in early development, initially appearing between embryonic day (E) 7.5 and 9.5.

Using primers based on brain-specific mouse EST sequences that contained internal sequences highly related to the human RFX4 cDNAs in GenBank, PCR and an adult mouse brain cDNA library were used to generate a 3 kb plasmid insert that was then sequenced. This cDNA has been designated the RFX4 variant transcript 3 (RFX4_v3). When this sequence was merged with all available 5' and 3' mouse ESTs from GenBank, the resulting mouse RFX4_v3 transcript (SEQ ID NO: 5) (GenBank Accession No. AY1020010) closely approximated the transcript size seen on Northern blots. Similar probes were then used to screen a human brain cDNA library, and positive inserts were sequenced. This novel DNA sequence has been designated human RFX4_v3 (SEQ ID NO: 7) (GenBank Accession No. AY102009). The predicted unique mouse amino terminal protein sequence also was used to search the non-human non-mouse ESTs in GenBank, and a zebrafish EST clone (AI657628) with a nearly identical predicted protein sequence was obtained from the IMAGE consortium and sequenced. This cDNA sequence is referred to as zebrafish RFX4_v3 (SEQ ID NO: 9) (GenBank Accession No.: AY102011).

The human chromosome 12 sequence was then searched with the mouse and human cDNA sequences, and it was determined that the exons contributed to the novel human RFX4_v3 isoform (SEQ ID NO: 7), in addition to those embodiments described above that corresponded to the two previously described human cDNAs (SEQ ID NOS: 1, 3, and 14). The two previously described human RFX4 cDNAs (RFX4_v1 and RFX4_v2) are composed of both unique and shared exons. In the case of the cDNA represented by accession number NM_002920 (SEQ ID NO: 1), the first five exons (shown as exons 1-5 of RFX4_v2 (NM_002920) in FIG. 2) correspond to five exon coding sequences within the 90 kb interval between bp 390,000-480,000 of the genomic clone NT_009720.8 (in reverse complement orientation). The next nine exons and part of a tenth (exons 6-15A of RFX4_v2 in FIG. 2) are common to the other version of RFX4 in GenBank (RFX4_v1), represented by the cDNA NM_032491 (SEQ ID NO: 14). These 10 exons are derived from exon coding sequences in the genomic clone NT_009720.8 between 340,000 and 400,000. As shown in FIG. 2, the final (15th) exon of RFX4_v2 contains a polyadenylation (poly A) sequence that allows for final processing of the mature mRNA.

The other human cDNA, RFX4_v1, contains an amino terminal exon 1 (hatching) that is encoded by an exon located between exons 5 and 6 of RFX_v2 (see FIG. 2). RFX4_v1 then shares exons (2-11) with RFX_v2 (exons 6-15A), followed by three unique carboxyl terminal exons (exons 12-14 of RFX4_v1). These last three unique exons are found within the interval bp 315,000-325,000 of the genomic clone NT_009720.8. Exon 12 from RFX4_v1 is apparently spliced into exon 15 of RFX4_v2, resulting in the novel 3' end of RFX4_v1 and a different poly A tail. The displaced sequence in RFX4_v2 is represented as exon 15B in FIG. 2.

The exon pattern that corresponds to the mouse and human RFX4_v3 mRNAs and proteins is illustrated at the bottom of FIG. 2. A completely novel exon 1, derived from a sequence between 480,000 and 500,000 of NT_009720.8, was used to form the first 14 amino acids at the amino terminal end (FIG. 2). The next four exons, 2-5, are composed of the four exons of the same number from RFX4_v2; exon 1 of RFX4_v2 is not present in the RFX4_v3 cDNA. The middle of the RFX4_v3 cDNA is formed by the 10 exons (exons 6-15 of RFX4_v3) held in common between RFX4_v2 (exons 6-15A) and RFX4_v1 (exons 2-11). The carboxyl terminus of RFX4_v3 (exons 16-18) is composed of the three carboxyl-terminal exons present only in RFX4_v1 (exons 12-14)). Thus, the novel RFX4_v3 isoform (SEQ ID NO: 7) described here comprises of a unique arrangement of 18 exons derived from almost 200 kb of human genomic sequence. One exon (the first) appears to be unique to this sequence; exons 2-5 are shared with RFX4_v2; exons 6-15 are shared with both RFX4_v1 and RFX4_v2; and exons 16-18 are shared with only RFX4_v1.

The site of transgene interruption of RFX4_v3 is also illustrated in FIG. 2 with a large black X. The greater than 15 kb transgene was inserted into the intron between exons 17 and 18 of RFX4_v3 (SEQ ID NO: 7), within the carboxyl-terminal end of the protein coding region, and appears to interfere with splicing of the final exon and generation of an intact mature mRNA. However, an understanding of the mechanism is not necessary in order to make and use the present disclosure.

The present disclosure also provides nucleic acids encoding RFX4_v3 genes, homologs, variants, and mutants (e.g., SEQ ID NOS: 1, 3, 5, 7, and 9). In some embodiments, polynucleotide sequences are capable of hybridizing to SEQ ID NOS: 1, 3, 5, 7, and 9 under conditions of low to high stringency as long as the polynucleotide sequence capable of hybridizing encodes a protein that retains a biological activity of the naturally occurring RFX4_v3. In some embodiments, the protein that retains a biological activity of naturally occurring RFX4_v3 is 70% homologous to wild-type RFX4_v3, preferably 80% homologous to wild-type RFX4_v3, more preferably 90% homologous to wild-type RFX4_v3, and most preferably 95% homologous to wild-type RFX4_v3. In preferred embodiments, hybridization conditions are based on the melting temperature ($T_m$) of the nucleic acid binding complex and confer a defined "stringency" as explained above (see e.g., Wahl, et al., *Meth. Enzymol.*, 152:399-407 [1987]).

In other embodiments of the present disclosure, alleles of RFX4 v3 are provided. In preferred embodiments, alleles result from a mutation, (i.e., a change in the nucleic acid sequence) and generally produce altered mRNAs or polypeptides whose structure or function may or may not be altered. Any given gene may have none, one or many allelic forms. Common mutational changes that give rise, to alleles are generally ascribed to deletions, additions or substitutions of nucleic acids. Each of these types of changes may occur alone, or in combination with the others, and at the rate of one or more times in a given sequence. Examples of the alleles of the present disclosure include those encoded by SEQ ID NOS: 5, 7 and 9 (wild-type) and those same sequences with an epoxygenase transgene insertion resulting in congenital hydrocephalus alleles.

In still other embodiments of the present disclosure, the nucleotide sequences of the present disclosure may be engineered in order to alter a RFX4_v3 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.) In some embodiments, mutations are created in the sequence to generate a dysfunctional gene product (e.g., a stop codon is placed at any position within the coding sequence). Such compositions find use as positive controls and for generating null cell lines and animal models through homologous recombination substituting for the wild-type counterpart. Such compositions also find use as a control for dose-dependent expression of congenital hydrocephalus.

In some embodiments, the polynucleotide sequence of RFX4_v3 may be extended utilizing the nucleotide sequences (e.g., SEQ ID NOS: 5, 7, and 9) in various methods known in the art to detect upstream sequences such as promoters and regulatory elements. Using this method, the sequence for the proximal promoter for human RFX4_v3 (SEQ ID NO: 11) and mouse RFX4_v3 (SEQ ID NO: 12) were identified. FIG. 3 demonstrates a partial alignment of human and mouse proximal promoter sequences for RFX4_v3.

In other embodiments, it is contemplated that restriction-site polymerase chain reaction (PCR) finds use in the present disclosure for identifying unknown sequences adjacent to RFX4_v3. This is a direct method that uses universal primers to retrieve unknown sequence adjacent to a known locus (Gobinda et al., *PCR Methods Applic.*, 2:318-22 [1993]). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR is used to amplify or extend sequences using divergent primers based on a known region (Triglia et al., *Nucleic Acids Res.*, 16:8186 [1988]). The primers may be designed using Oligo 4.0 (National Biosciences Inc, Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., *Nucleic Acids Res.*, 19:3055-60 [1991]). The PROMOTERFINDER kit (Clontech) uses PCR, nested primers and special libraries to "walk in" genomic DNA. This process avoids the need to screen libraries and is useful in finding intron/exon junctions. Preferred libraries for screening for full-length cDNAs include mammalian libraries (e.g., mouse and human libraries that were used to originally identify isoforms of RFX4) that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present disclosure, variants of the disclosed RFX4_v3 sequences are provided. In preferred embodiments, variants result from mutation, (i.e., a change in the nucleic acid sequence) and generally produce altered mRNAs or polypeptides whose structure or function may or may not be altered. Wherein mRNAs or polypeptides structures or functions are altered, a dose-dependent phenotype of congenital hydrocephalus appears. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence. Diagnostic methods can detect mutational changes to diagnose or predict the development of RFX4_v3 linked congenital hydrocephalus.

A modified peptide can be produced in which the nucleotide sequence encoding the polypeptide has been altered, such as by substitution, deletion, or addition. In particularly preferred embodiments, these modifications do not significantly reduce the biological activity of the modified RFX4_v3. In other words, a modified construct can be evaluated in order to determine whether it is a member of the genus of modified or variant RFX4_v3's of the present disclosure as defined functionally, rather than structurally. In preferred embodiments, the activity of variant or mutant RFX4_v3 is evaluated by the presence of the congenital hydrocephalus phenotype, for example in mice that express the variant. Accordingly, in some embodiments, the present disclosure provides nucleic acids encoding a RFX4_v3 that differentially provides varying degrees of congenital hydrocephalus.

Moreover, as described above, variant forms of RFX4_v3 are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present disclosure provide variants of RFX4_v3 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g. Stryer ed., *Biochemistry*, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g. LASERGENE software, DNASTAR Inc., Madison, Wis.).

As described in more detail below, variants may be produced by methods such as directed evolution or other techniques for producing combinatorial libraries of variants, described in more detail below. In still other embodiments of the present disclosure, the nucleotide sequences of the present disclosure may be engineered in order to alter a RFX4_v3 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.)

II. RFX4_v3 Polypeptides

In other embodiments, the present disclosure provides RFX4_v3 polynucleotide sequences that encode RFX4_v3 polypeptide sequences. An alignment of the amino terminal end of three predicted amino acid sequences is shown in FIG. 4 and in FIG. 6 for human, mouse and zebrafish RFX4_v3 (SEQ ID NOS: 8, 6, and 10, respectively); these translation protein sequences correspond to nucleic acid sequences of SEQ ID NOS: 37, 38 and 39, respectively. There is significant amino acid identity between the mouse and human proteins as demonstrated by FIG. 5 and FIG. 6. There is 96% amino acid identity between the predicted mouse and human proteins, and 83% amino acid identity between the human and zebrafish proteins. The alignment also illustrates several of the characteristic domains of the RFX4_v3 proteins that are conserved in all three orthologues, i.e., the highly conserved DNA binding domain, boxes B and C, and the dimerization domain (Morotomi-Yano, et al., *J. Biol. Chem.*, 277:836-842 [2002]). See FIG. 6.

Other embodiments of the present disclosure provide fragments, fusion proteins or functional equivalents of these RFX4_v3 proteins. In still other embodiments of the present disclosure, nucleic acid sequences corresponding to these various RFX4_v3 homologs and mutants may be used to generate recombinant DNA molecules that direct the expression of the RFX4_v3 homologs and mutants in appropriate host cells. In some embodiments of the present disclosure, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present disclosure may be glycosylated or may be non-glycosylated. In other embodiments, the polypeptides of the disclosure may also include an initial methionine amino acid residue.

In one embodiment of the present disclosure, due to the inherent degeneracy of the genetic code, DNA sequences other than the polynucleotide sequences described above, which encode substantially the same or a functionally equivalent amino acid sequence, may be used to clone and express RFX4_v3. In general, such polynucleotide sequences hybridize to the sequences described above under conditions of high to medium stringency as described above. As will be understood by those of skill in the art, it may be advantageous to produce RFX4_v3-encoding nucleotide sequences possessing non-naturally occurring codons. Therefore, in some preferred embodiments, codons preferred by a particular prokaryotic or eukaryotic host (Murray et al., *Nucl. Acids Res.*, 17 [1989]) are selected, for example, to increase the rate of RFX4_v3 expression or to produce recombinant RNA transcripts having desirable properties, such as a longer half-life, than transcripts produced from naturally occurring sequence.

1. Vectors for Production of RFX4_v3

The polynucleotides of the present disclosure may be employed for producing polypeptides by recombinant techniques. Thus, for example, the polynucleotide may be included in any one of a variety of expression vectors for expressing a polypeptide. In some embodiments of the present disclosure, vectors include, but are not limited to, chromosomal, nonchromosomal, and synthetic DNA sequences (e.g., derivatives of SV40, bacterial plasmids, phage DNA, baculovirus, yeast plasmids, vectors derived from combinations of plasmids and phage DNA, and viral DNA such as vaccinia, adenovirus, fowl pox virus, and pseudorabies). It is contemplated that any vector may be used as long as it is repilcable and viable in the host.

In particular, some embodiments of the present disclosure provide recombinant constructs comprising one or more of the sequences as broadly described above (e.g., SEQ ID NOS: 5, 7, and 9). In some embodiments of the present disclosure, the constructs comprise a vector, such as a plasmid or viral vector, into which a sequence of the disclosure has been inserted, in a forward or reverse orientation. In still other embodiments, the heterologous structural sequence is assembled in appropriate phase with translation initiation and termination sequences. In preferred embodiments of the present disclosure, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present disclosure, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present disclosure, the DNA sequence in the expression vector is operatively linked to an appropriate expression control sequence(s) (promoter) to direct mRNA synthesis. Promoters useful in the present disclosure include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present disclosure, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present disclosure, transcription of the DNA encoding the polypeptides of the present disclosure by higher eukaryotes is increased by inserting an enhancer sequence into the vector. Enhancers are cis-acting elements of DNA, usually about from 10 to 300 bp that act on a promoter to increase its transcription. Enhancers useful in the present disclosure include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present disclosure, the vector may also include appropriate sequences for amplifying expression.

2. Host Cells for Production of RFX4_v3

In a further embodiment, the present disclosure provides host cells containing the above-described constructs. In some embodiments of the present disclosure, the host cell is a higher eukaryotic cell (e.g., a mammalian or insect cell). In other embodiments of the present disclosure, the host cell is a lower eukaryotic cell (e.g., a yeast cell). In still other embodiments of the present disclosure, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell, 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (see e.g., Davis et al., *Basic Methods in Molecular Biology*, [1986]). Alternatively, in some embodiments of the present disclosure, the polypeptides of the disclosure can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present disclosure. Appropriate cloning and expression vectors for use with prokaryotic and eukaryotic hosts are described by Sambrook, et al., *Molecular Cloning: A Laboratory Manual*, Second Edition, Cold Spring Harbor, N.Y., [1989].

In some embodiments of the present disclosure, following transformation of a suitable host strain and growth of the host strain to an appropriate cell density, the selected promoter is induced by appropriate means (e.g., temperature shift or chemical induction) and cells are cultured for an additional period. In other embodiments of the present disclosure, cells are typically harvested by centrifugation, disrupted by physical or chemical means, and the resulting crude extract retained for further purification. In still other embodiments of the present disclosure, microbial cells employed in expression of proteins can be disrupted by any convenient method, including freeze-thaw cycling, sonication, mechanical disruption, or use of cell lysing agents.

3. Purification of RFX4_v3

The present disclosure also provides methods for recovering and purifying RFX4_v3 from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present disclosure, protein refolding steps can be used as necessary, in completing configuration of the mature protein. In still other embodiments of the present disclosure, high performance liquid chromatography (HPLC) can be employed for final purification steps.

The present disclosure further provides polynucleotides that can have the coding sequence fused in frame to a marker sequence, which allows for purification of the polypeptide of the present disclosure. A non-limiting example of a marker sequence is a hexahistidine tag which may be supplied by a vector, such as a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., *Cell*, 37:767 [1984]).

4. Truncation Mutants of RFX4_v3

In addition, the present disclosure provides fragments of RFX4_v3 (i.e., truncation mutants). In some embodiments of the present disclosure, when expression of a portion of the RFX4_v3 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., *J. Bacteriol.*, 169:751 [1987]) and *Salmonella typhimurium* and its in vitro activity has been demonstrated on recombinant proteins (Miller et al, *Proc. Natl. Acad. Sci. USA* 84:2718 [1990]). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP.

5. Fusion Proteins Containing RFX4_v3

The present disclosure also provides fusion proteins incorporating all or part of RFX4_v3. Accordingly, in some embodiments of the present disclosure, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a RFX4_v3 protein. In some embodiments of the present disclosure, the VP6 capsid protein of rotavirus is used as an immunologic carrier protein for portions of the RFX4_v3 polypeptide, either in the monomeric form or in the form of a viral particle. In other embodiments of the present disclosure, the nucleic acid sequences corresponding to the portion of RFX4_v3 against which antibodies are to be raised can be incorporated into a fusion gene construct which includes coding sequences for a late vaccinia virus structural protein to produce a set of recombinant viruses expressing fusion proteins comprising a portion of RFX4_v3 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present disclosure, chimeric constructs coding for fusion proteins containing a portion of RFX4_v3 and the poliovirus capsid protein are created to enhance immunogenicity of the set of polypeptide antigens (see e.g., EP Publication No. 025949; and Evans et al., *Nature*, 339:385 [1989]; Huang et al., *J. Virol.*, 62:3855 [1988]; and Schlienger et al., *J. Virol.*, 66:2 [1992]).

In still other embodiments of the present disclosure, the multiple antigen peptide system for peptide-based immunization can be utilized In this system, a desired portion of RFX4_v3 is obtained directly from organo-chemical synthesis of the peptide onto an oligomeric branching lysine core (see e.g., Posnett et al., *J. Biol. Chem.*, 263:1719 [1988]; and Nardelli et al., *J. Immunol.*, 148:914 [1992]). In other embodiments of the present disclosure, antigenic determinants of the RFX4_v3 proteins can also be expressed and presented by bacterial cells.

In addition to utilizing fusion proteins to enhance immunogenicity, it is widely appreciated that fusion proteins can also facilitate the expression of proteins, such as the RFX4_v3 protein of the present disclosure. Accordingly, in some embodiments of the present disclosure, RFX4_v3 can be generated as a glutathione-S-transferase (i.e., GST fusion protein). It is contemplated that such GST fusion proteins will enable easy purification of RFX4_v3, such as by the use of glutathione-derivatized matrices (see e.g., Ausabel et al. (eds.), *Current Protocols in Molecular Biology*, John Wiley & Sons, NY [1991]). In another embodiment of the present disclosure, a fusion gene coding for a purification leader sequence, such as a poly-(His)/enterokinase cleavage site sequence at the N-terminus of the desired portion of RFX4_v3, can allow purification of the expressed RFX4_v3 fusion protein by affinity chromatography using a $Ni^{2+}$ metal resin. In still another embodiment of the present disclosure, the purification leader sequence can then be subsequently removed by treatment with enterokinase (see e.g., Hochuli et al., *J. Chromatogr.*, 411:177 [1987]; and Janknecht et al., *Proc. Natl. Acad Sci USA,* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present disclosure, the fusion gene can be synthesized by conventional techniques including automated DNA synthesizers. Alternatively, in other embodiments of the present disclosure, PCR amplification of gene fragments can be carried out using anchor primers which give rise to complementary overhangs between two consecutive gene fragments which can subsequently be annealed to generate a chimeric gene sequence (see e.g., *Current Protocols in Molecular Biology*, supra).

6. Variants of RFX4_v3

Still other embodiments of the present disclosure provide mutant or variant forms of RFX4_v3 (i.e., muteins). It is possible to modify the structure of a peptide having an activity of RFX4_v3 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject RFX4_v3 proteins as defined herein. A modified peptide can be produced in which the amino acid sequence has been altered, such as by amino acid substitution, deletion, or addition.

Moreover, as described above, variant forms (e.g., mutants) of the subject RFX4_v3 proteins are also contemplated as being equivalent to those peptides and DNA molecules that are set forth in more detail. For example, as described above, the present disclosure encompasses mutant and variant proteins that contain conservative or non-conservative amino acid substitutions.

This disclosure further contemplates a method of generating sets of combinatorial mutants of the present RFX4_v3 proteins, as well as truncation mutants, and is especially useful for identifying potential variant sequences (i.e., homologs) that are functional. The purpose of screening such combinatorial libraries is to generate, for example, novel RFX4_v3 homologs that can act as either agonists or antagonists, or alternatively, possess novel activities all together, such as a replacement therapy for a defective RFX4_v3 transcript to prevent phenotypic expression of congenital hydrocephalus.

Therefore, in some embodiments of the present disclosure, RFX4_v3 homologs are engineered by the present method to provide a more efficient transcription factor. In other embodiments of the present disclosure, combinatorially-derived homologs are generated which have a selective potency relative to a naturally occurring RFX4_v3. Such proteins, when expressed from recombinant DNA constructs, can be used in gene therapy protocols.

Still other embodiments of the present disclosure provide RFX4_v3 homologs that have intracellular half-lives dramatically different than the corresponding wild-type protein. For example, the altered protein can be rendered either more stable or less stable to proteolytic degradation or other cellular process that result in destruction of, or otherwise inactivate RFX4_v3. Such homologs, and the genes which encode them, can be utilized to alter the location of RFX4_v3 expression by modulating the half-life of the protein. For instance, a short half-life can give rise to more transient RFX4_v3 biological effects and, when part of an inducible expression system, can allow tighter control of RFX4_v3 levels within the cell. As above, such proteins, and particularly their recombinant nucleic acid constructs, can be used in gene therapy protocols.

In still other embodiments of the present disclosure, RFX4_v3 homologs are generated by the combinatorial approach to act as antagonists, in that they are able to interfere with the ability of the corresponding wild-type protein to regulate cell function. These antagonists may be useful in the controlled production of animal models with dose-dependent manifestations of hydrocephalus for further study.

In some embodiments of the combinatorial mutagenesis approach of the present disclosure, the amino acid sequences for a population of RFX4_v3 homologs or other related proteins are aligned, preferably to promote the highest homology possible. Such a population of variants can include, for example, RFX4_v3 homologs from one or more species, or RFX4_v3 homologs from the same species but which differ due to mutation. Amino acids that appear at each position of the aligned sequences are selected to create a degenerate set of combinatorial sequences.

In a preferred embodiment of the present disclosure, the combinatorial RFX4_v3 library is produced by way of a degenerate library of genes encoding a library of polypeptides which each include at least a portion of potential RFX4_v3 protein sequences. For example, a mixture of synthetic oligonucleotides can be enzymatically ligated into gene sequences such that the degenerate set of potential RFX4_v3 sequences are expressible as individual polypeptides, or alternatively, as a set of larger fusion proteins (e.g., for phage display) containing the set of RFX4_v3 sequences therein.

There are many ways by which the library of potential RFX4_v3 homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential RFX4_v3 sequences. The synthesis of degenerate oligonucleotides is well known in the art (see e.g., Narang *Tetrahedron Lett.,* 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., *Annu. Rev. Biochem.,* 53:323 [1984]; Itakura et al., *Science*, 198:1056 [1984]; Ike et al., *Nucl. Acid Res.,* 11:477 [1983]). Such techniques have been employed in the directed evolution of other proteins (see e.g., Scott et al., *Science*, 249:386 [1990]; Roberts et al., *Proc. Natl. Acad. Sci. USA,* 89:2429 [1992]; Devlin et al., *Science*, 249: 404 [1990]; Cwirla et al., *Proc. Natl. Acad. Sci USA,* 87: 6378 [1990]; as well as U.S. Pat. Nos. 5,223,409; 5,198,346; and 5,096,815).

It is contemplated that the RFX4_v3 nucleic acids (e.g. SEQ ID NOS: 5, 7 and 9, and fragments and variants thereof) can be utilized as starting nucleic acids for directed evolution. These techniques can be utilized to develop RFX4_v3 variants having desirable properties such as increased or decreased ability to compete with a naturally occurring defective transcript that induces congenital hydrocephalus.

In some embodiments, artificial evolution is performed by random mutagenesis (e.g. by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, *Nat. Biotech.*, 14, 458 [1996]; Leung et al, *Technique*, 1:11 [1989]; Eckert and Kunkel, *PCR Methods Appl.*, 1:17-24 [1991]; Caldwell and Joyce, *PCR Methods Appl.*, 2:28 [1992]; and Zhao and Arnold, *Nuc. Acids. Res.*, 25:1307 [1997]). After mutagenesis, the resulting clones are selected for desirable activity (e.g., screened for RFX4_v3 activity). Successive rounds of mutagenesis and selection are often necessary to develop enzymes with desirable properties. It should be noted that only the useful mutations are carried over to the next round of mutagenesis.

In other embodiments of the present disclosure, the polynucleotides of the present disclosure are used in gene shuffling or sexual PCR procedures (e.g. Smith, *Nature*, 370:324 [1994]; U.S. Pat. Nos. 5,837,458; 5,830,721; 5,811,238; 5,733,731). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations present in different clones becoming mixed and accumulating in some of the resulting sequences. Multiple cycles of selection and shuffling have led to the functional enhancement of several enzymes (Stemmer, *Nature*, 370:398 [1994]; Stemmer, *Proc. Natl. Acad. Sci. USA*, 91:10747 [1994]; Crameri et al., *Nat. Biotech.*, 14:315 [1996]; Zhang et al, *Proc. Natl. Acad Sci USA*, 94:4504 [1997]; and Crameri et al., *Nat. Biotech.*, 15:436 [1997]).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of RFX4_v3 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of RFX4_v3

In an alternate embodiment of the disclosure, the coding sequence of RFX4_v3 is synthesized, in whole or in part, using chemical methods well known in the art (see e.g., Caruthers et al., *Nucl. Acids Res. Symp. Ser.*, 7:215 [1980]; Crea and Horn, *Nucl. Acids Res.*, 9:2331 [1980]; Matteucci and Caruthers, *Tetrahedron Lett.*, 21:719 [1980]; and Chow and Kempe, *Nucl. Acids Res.*, 9:2807 [1981]). In other embodiments of the present disclosure, the protein itself is produced using chemical methods to synthesize either an entire RFX4_v3 amino acid sequence or a portion thereof. For example, peptides can be synthesized by solid phase techniques, cleaved from the resin, and purified by preparative high performance liquid chromatography (see e.g., Creighton, *Proteins Structures And Molecular Principles*, W H Freeman and Co, New York N.Y. [1983]). In other embodiments of the present disclosure, the composition of the synthetic peptides is confirmed by amino acid analysis or sequencing (see e.g., Creighton, supra).

Direct peptide synthesis can be performed using various solid-phase techniques (Roberge et al., *Science*, 269:202 [1995]) and automated synthesis may be achieved, for example, using ABI 431A Peptide Synthesizer (Perkin Elmer) in accordance with the instructions provided by the manufacturer. Additionally, the amino acid sequence of RFX4_v3, or any part thereof, may be altered during direct synthesis and/or combined using chemical methods with other sequences to produce a variant polypeptide.

III. Detection of RFX4_v3 Alleles

A. RFX4_v3 Alleles

In some embodiments, the present disclosure includes alleles of RFX4_v3 that increase a subject's susceptibility to congenital hydrocephalus (e.g., including, but not limited to, sequences described above with the epoxygenase transgene insert). In some embodiments, subjects (e.g., human subjects) with an increased susceptibility to congenital hydrocephalus are identified through the detection of mutant RFX4_v3 alleles. Any mutation that results in the undesired phenotype is within the scope of the present disclosure.

For example, in some embodiments, the present disclosure provides single-nucleotide polymorphisms of RFX4_v3 that produce varying levels of expression of the congenital hydrocephalus phenotype compared to the wild-type sequence.

B. Detection of RFX4_v3 Alleles

Accordingly, the present disclosure provides methods for determining whether a subject has an increased susceptibility to congenital hydrocephalus by determining whether the individual has a mutated gene. In other embodiments, the present disclosure provides methods for providing a prognosis of increased risk for congenital hydrocephalus to an individual based on the presence or absence of one or more mutations. In some embodiments, the mutation is in the RFX4_v3 gene. In other embodiments, the mutation manifests as dose dependent congenital hydrocephalus. In some embodiments, the mutation is a single nucleotide polymorphism caused by an insertion of any number of residues or a single nucleotide substitution. In other embodiments, the mutation can result from multiple nucleotide polymorphisms caused by an insertion of any number of residues or a single nucleotide substitution into the RFX4_v3 transcript.

In still further embodiments, the detection of polymorphisms is not limited to the RFX4 v3 transcript. Since RFX4_v1 and RFX4_v2 each have exons in common with RFX4_v3 (see FIG. 2), detection of polymorphisms in any of the common exons provides additional methods for detecting an increased susceptibility to congenital hydrocephalus.

To perform a diagnostic test for the presence or absence of a mutation in a RFX4_v3 sequence of an individual, a suitable genomic DNA-containing sample from a subject is obtained and the DNA extracted using conventional techniques. For instance, a blood sample, a buccal swab, a hair follicle preparation, a nasal aspirate, a cerebral spinal fluid sample, or an amniotic fluid sample is used as a source of cells to provide the DNA sample. Similarly, a surgical specimen, such as a brain tissue biopsy, or other biological sample containing genomic DNA could be used. The extracted DNA is then subjected to amplification, for example according to standard procedures. The allele of the single base-pair mutation is determined by conventional methods including manual and automated fluorescent DNA sequencing, primer extension methods (Nikiforov, et al., *Nucl Acids Res.* 22:4167-4175, 1994), oligonucleotide ligation assay (OLA) (Nickerson et al., *Proc. Natl. Acad. Sci. USA* 87:8923-8927, 1990), allele-specific PCR methods (Rust et al., *Nucl. Acids Res.* 6:3623-3629, 1993), RNase mismatch cleavage, single strand conformation polymorphism (SSCP), denaturing gradient gel electrophoresis (DGGE), Taq-Man™, oligonucleotide hybridization, and the like. Also, see the following U.S. Patents for descriptions of methods or applications of polymorphism analysis to disease prediction and/or diagnosis: U.S. Pat. No. 4,666,828 (RFLP for Huntington's); U.S. Pat. No. 4,801,531 (prediction of atherosclerosis); U.S. Pat. No. 5,110,920 (HLA typing); U.S. Pat. No. 5,268,267 (prediction of small cell carcinoma); and U.S. Pat. No. 5,387,506 (prediction of dysautonomia).

In general, assays for detecting polymorphisms or mutations fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present disclosure.

1. Direct Sequencing Assays

In some embodiments of the present disclosure, polymorphisms are detected using a direct sequencing technique. In these assays, DNA samples are first isolated from a subject using any suitable method. In some embodiments, the RFX4_v3 gene or any part thereof is cloned into a suitable vector and amplified by growth in a host cell (e.g. a bacterium). In other embodiments, DNA in the RFX4_v3 gene or any part thereof is amplified using PCR.

Following amplification, DNA in the RFX4_v3 gene or any part thereof (e.g., the region containing the polymorphism or mutation of interest) is sequenced using any suitable method, including but not limited to manual sequencing using radioactive marker nucleotides, or automated sequencing. The results of the sequencing are displayed using any suitable method. The sequence is examined and the presence or absence of a given polymorphism or mutation is determined.

2. PCR Assay

In some embodiments of the present disclosure, polymorphisms are detected using a PCR-based assay. In some embodiments, the PCR assay comprises the use of oligonucleotide primers that hybridize only to the mutant or wild-type allele of RFX4_v3 (e.g., to the region of polymorphism). Both sets of primers are used to amplify a sample of DNA. If only the mutant primers result in a PCR product, then the patient has the mutant RFX4_v3 allele. If only the wild-type primers result in a PCR product, then the patient has the wild-type allele of RFX4_v3.

3. Fragment Length Polymorphism Assays

In some embodiments of the present disclosure, polymorphisms are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a polymorphism or a mutation will have a different banding pattern than wild-type.

a. RFLP Assay

In some embodiments of the present disclosure, polymorphisms are detected using a restriction fragment length polymorphism assay (RFLP). The RFX4_v3 gene or any part thereof is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, polymorphisms are detected using a CLEAVASE fragment length polymorphism assay (CFLP; Third Wave Technologies, Madison, Wis.; see e.g., U.S. Pat. Nos. 5,843,654; 5,843,669; 5,719,208; and 5,888,780). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given polymorphism or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

4. Hybridization Assays

In preferred embodiments of the present disclosure, polymorphisms are detected in a hybridization assay. In a hybridization assay, the presence of absence of a given polymorphism or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a polymorphism or mutation) is detected directly by visualizing a bound probe (e.g., a Northern or Southern assay; see e.g., Ausabel et al. (eds.), *Current Protocols in Molecular Biology*, John Wiley & Sons, NY [1991]). In these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the polymorphism or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present disclosure, polymorphisms are detected using a DNA chip hybridization assay. In this assay, a series of oligonucleotide probes are affixed to a solid support The oligonucleotide probes are designed to be unique to a given polymorphism or mutation. The DNA sample of interest is contacted with the DNA "chip" and hybridization is detected.

In some embodiments, the DNA chip assay is a GeneChip (Affymetrix, Santa Clara, Calif.; see e.g., U.S. Pat. Nos. 6,045,996; 5,925,525; and 5,858,659) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (see e.g., U.S. Pat. Nos. 6,017,696; 6,068,818; and 6,051,380). Through the use of microelectronics, Nanogen's technology enables the active movement and concentration of charged molecules to and from designated test sites on its semiconductor microchip. DNA capture probes unique to a given polymorphism or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g. a PCR amplified RFX4_v3 gene). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (see e.g., U.S. Pat. Nos. 6,001,311; 5,985,551; and 5,474,796). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by centrifugation.

DNA probes unique for the polymorphism or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; see e.g., PCT Publications WO 99/67641 and WO 00/39587). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given polymorphism or mutation. Batches of beads are combined to form a pool specific to the array. To perform an assay, the BEAD ARRAY is contacted with a prepared subject sample (e.g. DNA). Hybridization is detected using any suitable method.

C. Enzymatic Detection of Hybridization

In some embodiments of the present disclosure, genomic profiles are generated using an assay that detects hybridization by enzymatic cleavage of specific structures (INVADER assay, Third Wave Technologies; see e.g., U.S. Pat. Nos. 5,846,717; 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and polymorphisms in unamplified genomic DNA. The isolated DNA sample is contacted with the first probe specific either for a polymorphism/mutation or wild-type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; see e.g. U.S. Pat. Nos. 5,962,233 and 5,538,848). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorometer.

In still further embodiments, polymorphisms are detected using the SNP-IT primer extension assay (Orchid Biosciences, Princeton, N.J.; see e.g., U.S. Pat. Nos. 5,952,174 and 5,919,626). In this assay, single nucleotide polymorphisms (SNPs) are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g. if the nucleotide contains a biotin label, detection is via a fluorescently labeled antibody specific for biotin).

5. Mass Spectroscopy Assay

In some embodiments, a MassARRAY system (Sequenom, San Diego, Calif.) is used to detect polymorphisms (see e.g., U.S. Pat. Nos. 6,043,031; 5,777,324; and 5,605,798). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 seconds including repetitive data collection. The SpectroTYPER software then calculates, records, compares and reports the genotypes at the rate of three seconds per sample.

6. Mutant Analysis by Differential Differential Detection of RFX4_v3 Homologs

With the provision herein of the unique N-terminus of human, mouse and zebrafish RFX4_v3 homologs, it is now possible to design and/or construct specific binding molecules, such as nucleic acid probes or antibodies, to specifically identify RFX4_v3 homologs. Such RFX4_v3-specific binding molecules are useful, for example, to distinguish RFX4_v3 homologs from related RFX4 variants (e.g., RFX4_v1 and RFX4_v2).

In some embodiments, antibodies that are utilized discriminate between mutant (i.e., truncated proteins) and wild-type proteins (SEQ ID NOS: 6, 8, and 10). In some other embodiments, the antibodies are directed to the C-terminus of RFX4_v3 or the N-terminus of RFX4_v3. In other embodiments, the antibodies are directed to the first 14 amino acids at the N-terminus of RFX4_v3 (e.g., SEQ ID NOS: 33, 34 or 35). In certain embodiments, the antibodies are directed to the Reissner's fibers of the subcommissural organ. Production and use of RFX4_v3 antibodies is discussed in detail above in the section entitled "Generation of RFX4_v3 Antibodies."

In other embodiments, probes are used that discriminate between mutant (i.e., truncated proteins) and wild-type proteins (SEQ ID NOS: 6, 8, and 10). For example, in some embodiments probes are directed to the C-terminus of RFX4_v3 or the N-terminus of RFX4_v3. In other embodiments, probes are directed to the first 14 amino acids at the N-terminus of RFX4_v3 (e.g., SEQ ID NOS: 33, 34 or 35).

The preparation and use of nucleic acid probes are well-known in the art. For discussions of nucleic acid probe design and hybridization conditions, see, e.g., *Molecular Cloning: A Laboratory Manual* (2nd Ed.), Vols. 1-3, Sambrook, ed., Cold Spring Harbor Laboratory, (1989); *Current Protocols In Molecular Biology*, Ausubel, ed., John Wiley & Sons, Inc., New York (1997); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

7. Kits for Analyzing Risk of Congenital Hydrocephalus

The present disclosure also provides kits for determining whether an individual contains a wild-type or mutant allele of RFX4_v3. In some embodiments, the kits are useful for determining whether the subject is at risk of passing on a defective RFX4_v3 gene resulting in children with congenital hydrocephalus. The diagnostic kits are produced in a variety of ways. In some embodiments, the kits contain at least one reagent for specifically detecting a mutant RFX4_v3 allele or protein. In preferred embodiments, the reagent is a nucleic acid that hybridizes to nucleic acids containing a polymorphism and does not bind to nucleic acids that do not contain a polymorphism. In other preferred embodiments, the reagents are primers for amplifying the region of DNA containing a polymorphism. In still other embodiments, the reagents are antibodies that preferentially bind either the wild-type or truncated RFX4_v3 proteins. In some embodiments, the kit contains instructions for determining whether the subject is a carrier of a defective RFX4_v3 gene (e.g., instructions required by the regulations for in vitro diagnostic products). In preferred embodiments, the instructions specify that by detecting the presence or absence of a mutant RFX4_v3 allele in the subject, subjects having an allele containing a mutation have an increased risk of passing that mutated gene to their children, which may result in congenital hydrocephalus. In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a negative control sample.

8. Bioinformatics

In some embodiments, the present disclosure provides methods of determining whether and individual carries a defective RFX4_v3 allele. In some embodiments, the analysis of polymorphism data is automated. For example, in some embodiments, the present disclosure provides a bioinformatics research system comprising a plurality of computers running a mulit-platform object oriented programming language (see e.g., U.S. Pat. No. 6,125,383). In some embodiments, one of the computers stores genetics data (e.g., the severity of the congenital hydrocephalus with a given polymorphism). In some embodiments, one of the computers stores application programs (e.g. for analyzing transmission disequilibria data or determining genotype relative risks and population attributable risks). Results are then delivered to the user (e.g., via one of the computers or via the internet).

IV. Generation of RFX4_v3 Antibodies

Antibodies can be generated to allow for the specific detection of RFX4_v3 protein. The antibodies may be prepared using various immunogens. In one embodiment, the immunogen is a RFX4_v3 peptide to generate antibodies that recognize human and non-human RFX4_v3, but not RFX4_v1 or RFX4_v2. Such antibodies include, but are not limited to polyclonal, monoclonal, chimeric, single chain, Fab fragments, and Fab expression libraries.

Various procedures known in the art may be used for the production of polyclonal antibodies directed against RFX4_v3. For the production of antibody, various host animals can be immunized by injection with the peptide corresponding to a RFX4_v3 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward RFX4_v3, it is contemplated that any technique that provides for the production of antibody molecules by continuous cell lines in culture will find use with the present disclosure (see e.g. Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature, 256:495-497 [1975]), as well as the trioma technique, the human B-cell hybridoma technique (see e.g., Kozbor et al, Immunol. Tod., 4:72 [1983]), and the EBV-hybridoma technique to produce human monoclonal antibodies (Cole et al., "The EBV-hybridoma technique and its application to human lung cancer," in *Monoclonal Antibodies and Cancer Therapy*, Alan R. Liss, Inc., pp. 77-96 [1985]).

In an additional embodiment of the disclosure, monoclonal antibodies are produced in germ-free animals utilizing technology such as that described in PCT/US90/02545. Furthermore, it is contemplated that human antibodies will be generated by human hybridomas (Cote et al., *Proc. Natl. Acad. Sci. USA*, 80:2026-2030 [1983]) or by transforming human B cells with EBV virus in vitro (Cole et al., "The EBV-hybridoma technique and its application to human lung cancer," in *Monoclonal Antibodies and Cancer Therapy*, Alan R Liss, pp. 77-96 [1985]).

In addition, it is contemplated that techniques described for the production of single chain antibodies (U.S. Pat. No. 4,946, 778) will find use in producing RFX4_v3 specific single chain antibodies. An additional embodiment of the disclosure utilizes the techniques described for the construction of Fab expression libraries (Huse et al., Science, 246:1275-1281 [1989]) to allow rapid and easy identification of monoclonal Fab fragments with the desired specificity for RFX4_v3.

It is contemplated that any technique suitable for producing antibody fragments will find use in generating antibody fragments that contain the idiotype (antigen binding region) of the antibody molecule. For example, such fragments include but are not limited to: F(ab')2 fragments that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold or enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present disclosure. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of RFX4_v3 (e.g., for Western blotting), measuring levels thereof in appropriate biological samples, etc. The antibodies can be used to detect RFX4_v3 in a biological sample from an individual. The biological sample can be a biological fluid, such as, but not limited to, blood, serum, plasma, interstitial fluid, urine, cerebrospinal fluid, amniotic fluid and the like, containing cells.

The biological samples can then be tested directly for the presence of human RFX4 v3 using an appropriate strategy (e.g., ELISA or radioimmunoassay) and format (e.g. microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of RFX4_v3 detected by immunoblotting (Western blotting). Immunoblotting techniques are generally more effective with antibodies generated against a peptide corresponding to an epitope of a protein, and hence, are particularly suited to the present disclosure.

V. Gene Therapy Using RFX4_v3

The present disclosure also provides methods and compositions suitable for gene therapy to alter RFX4_v3 expression, production, or function. As described above, the present disclosure provides human RFX4_v3 genes and provides methods of obtaining RFX4_v3 genes from other species. Thus, the methods described below are generally applicable across many species. In some embodiments, it is contemplated that gene therapy is performed by providing a subject with a wild-type allele of RFX4_v3. Subjects in need of such therapy are identified by the methods described above. As described above, RFX4_v3 is primarily expressed in the brain. Accordingly, a preferred method of gene therapy is to replace the defective transcript with wild-type RFX4_v3.

Viral vectors commonly used for in vivo or ex vivo targeting and therapy procedures are DNA-based vectors and retroviral vectors. Methods for constructing and using viral vectors are known in the art (see e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present disclosure lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 0.1 (HSV1) vector (Kaplitt et al., Mol. Cell. Neurosci, 2:320-330 [1991]), defective herpes virus vector lacking a glycoprotein L gene (see e.g., Patent Publication RD 371005 A), or other defective herpes virus vectors (see e.g., WO 94/21807; and WO 92/05263); an attenuated adenovirus vector, such as the vector described by Stratford-Perricaudet et al. (J. Clin. Invest., 90:626-630 [1992]; see also, La Salle et al., Science, 259:988-990 [1993]); and a defective adeno-associated virus vector (Samulsid et al., J. Virol., 61:3096-3101 [1987]; Samulski et al., J. Virol., 63:3822-3828 [1989]; and LebkowskietaL, Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the disclosure to a variety of cell types. Various serotypes of adenovirus exist. Of these serotypes, preference is given, within the scope of the present disclosure, to type 2 or type 5 human adenoviruses (Ad 2 or Ad 5), or adenoviruses of animal origin (see e.g., WO94/26914). Those adenoviruses of animal origin that can be used within the scope of the present disclosure include adenoviruses of canine, bovine, murine (e.g., Mav1, Beard et al., Virol., 75-81 [1990]), ovine, porcine, avian, and simian (e.g., SAV) origin.

Preferably, the replication of defective adenoviral vectors of the disclosure comprises ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-Bg/II fragment) or 382 to 3446 (HinfII-Sau3A fragment). Other regions may also be modified, in particular the E3 region (e.g., WO95/02697), the E2 region (e.g., WO94/28938), the E4 region (e.g. WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the disclosure can be prepared by any technique known to the person skilled in the art (see e.g. Levrero et al., Gene, 101:195 [1991]; EP 185 573; and Graham, EMBO J., 3:2917 [1984]). In particular, they can be prepared by homologous recombination between an adenovirus and a plasmid, which carries inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J Gen Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, which are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (see e.g., WO 91/18088; WO 93/09239; U.S. Pat. No. 4,797,368; U.S. Pat. No. 5,139,941; and EP 488 528). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346; 4,650,764; 4,980,289; and 5,124,263; Mann et al., *Cell*, 33:153 [1983]; Markowitz et al., *J. Virol.*, 62:1120 [1988]; PCT/US95/14575; EP 453242; EP178220; Bernstein et al. *Genet Eng.*, 7:235 [1985]; McCormick, *BioTechnol.*, 3:689 [1985]; WO 95/07358; and Kuo et al., *Blood*, 82:845 [1993]). The retroviruses are integrating viruses that infect dividing cells. The retrovirus genome includes two LTRs, an encapsidation sequence and three coding regions (gag pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney Leukaemia Virus" MSV ("murine Moloney Sarcoma Virus"), HaSV ("Harvey Sarcoma Virus"); SNV ("Spleen Necrosis Virus"); RSV ("Rous Sarcoma Virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719), the PsiCRIP cell line (see, WO90/02806), and the GP+envAm-12 cell line (see, WO89/07150). In addition, the recombinant retroviral vectors can contain modifications within the LTRs for suppressing transcriptional activity as well as extensive encapsidation sequences that may include a part of the gag gene (Bender et al., *J. Virol.*, 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., *Proc. Natl. Acad. Sci. USA*, 84:7413-7417 [1987]; see also, Mackey, et al, *Proc. Natl. Acad. Sci. USA*, 85:8027-8031 [1988]; Ulmer et al., *Science*, 259:1745-1748 [1993]). The use of cationic lipids may promote encapsulation of negatively charged nucleic acids, and also promote fusion with negatively charged cell membranes (Felgner and Ringold, *Science*, 337:387-388 [1989]). Particularly useful lipid compounds and compositions for transfer of nucleic acids are described in WO95/18863 and WO96/17823, and in U.S. Pat. No. 5,459,127.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (see e.g., Wu et al., *J. Biol. Chem.*, 267:963 [1992]; Wu and Wu, *J. Biol. Chem.*, 263:14621 [1988]; and Williams et al., *Proc. Natl. Acad. Sci. USA*, 88:2726 [1991]). Receptor-mediated DNA delivery approaches can also be used (Curiel et al., *Hum. Gene Ther.*, 3:147 [1992]; and Wu and Wu, *J. Biol. Chem.*, 262:4429 [1987]).

VI. Transgenic Animals Expressing Heterologous RFX4_v3 Genes and Homologs, Mutants, and Variants thereof A line of transgenic mice that lacks RFX4_v3 was generated by a transgene insertion within the last intron of the RFX4 gene. Targeted insertional mutagenesis in mice has become a standard method for uncovering the roles of a specific gene in development. However, several instances of accidental insertion of a transgene into a critical genomic locus have yielded important information as well. For example, a Reeler-like phenotype was observed in one line of transgenic mice harboring an unrelated transgene (Miao, et al, *Natl. Acad. Sci. USA*, 91:11050-4 [1994]) herein incorporated by reference. The transgene had interrupted what is now known as the Reeler locus, and much has since been learned about the function of this gene and its gene product, reelin, in regulating the development of the central nervous system (D'Arcangelo, et al, *Nature*, 374:719-23, [1995]; D'Arcangelo, et al., *Brain Res. Mol. Brain Res.*, 39:234-6, [1996]; Rice and Curran, *Annu. Rev. Neurosci.*, 24:1005-39 [2001]). Several other examples have been described recently (Friedman, et al., *Laryngoscope*, 110:489-96, [2000]; Durkin, et al., *Genomics*, 73:20-7, [2001]; Overbeek, *Genesis*, 30:26-35, [2001]).

The phenotypes of the transgenic mice were dosage-dependent: brains from heterozygous mice expressed approximately 50% of normal levels of brain-specific transcript, and exhibited universal, severe congenital hydrocephalus. This obstructive hydrocephalus appeared to be secondary to failure of development of the subcommissural organ (SCO), a structure that is important for the patency of the aqueduct of Sylvius and normal cerebrospinal fluid flow in the brain (Perez-Figares, et al, *Microsc. Res. Tech.*, 52:591-607 [2001]; Rodriguez, et al., *Microsc. Res. Tech.*, 52:573-90 [2001]; Vio, et al., *Exp. Brain Res.*, 135:41-52 [2000]; Perez-Figares, et al., *J. Neuropathol. Exp. Neurol.*, 57:188-202 [1998]; Rodriguez, et al., *Microsc. Res. Tech.*, 41:98-123 [1998]; Cifuentes, et al., *Exp. Brain Res.*, 98:43140 [1994]). The heterozygous condition was compatible with life and fertility in some cases.

A single transgene insertion was demonstrated by Southern blotting of genomic DNA from affected mice. PCR-based techniques revealed that the inserted transgene consisted of at least 15 kb of foreign DNA, representing at least two tandem copies of the original 7.5 kb transgene. Using a GENOMEWALKER (BD Biosciences, Palo Alto, Calif.) approach with genomic DNA from transgenic mice, the 5' and 3' genomic sequences adjacent to the transgene insertional site was identified. These sequences were matched to incomplete mouse genomic sequences in GenBank. The mouse genomic sequences are highly related to a human chromosome 12 sequence. A BAC contig containing the human chromosome 12 sequence was analyzed for expressed sequences. All exons of the human winged helix protein RFX4, a testis-specific transcript (Morotomi-Yano et al., *J. Biol. Chem.*, 277:836-842 [2002] herein incorporated by reference), was found over a genomic region of nearly 100 kb.

Using probes derived from the junctions between the inserted transgene and the endogenous mouse genomic DNA, the wild-type (+/+) and transgene-interrupted alleles were distinguished by both Southern blotting and PCR-based approaches. Southern blot indicated additional bands present in heterozygous mice that were not present in wild-type mice. The Southern blot was hybridized with a transgene specific probe. PCR were also used to identify wild-type (+/+), heterozygous (+/−), and homozygous (−/−) mutant mice. PCR reactions were performed with primer pairs that either spanned the transgene insertion site or were transgene specific. Both approaches revealed the presence of both wild-type and "knockout" alleles in all of the affected mice.

Despite having severe hydrocephalus, significant proportions of both male and female mice survived to adulthood and were fertile. Interbreeding heterozygous (+/−) mice resulted in the birth of live pups with the homozygous (−/−) genotype, but these pups died shortly after birth and had obvious brain malformations. Investigation of fetal mice showed that homozygous mice exhibited severe brain malformations at embryonic (E) days 18.5 and 16.5. Mice at E12.5 had more orderly and characteristic brain structures, but these mice also exhibited severe brain malformations. The characteristic obstructive midline brain malformation was seen in all homozygous mice embryos examined.

To confirm that transgene insertion could prevent expression of a full-length RFX4 transcript in brain, Northern blots from brains of neonatal wild-type, heterozygous, and homozygous mice were probed with a mouse EST cDNA clone that was highly related to the putative final exon of the human cDNA and genomic sequence (Morotomi-Yano et al., *J. Biol. Chem.*, 277:836-842 [2002]). The EST probe revealed expression of a transcript of approximately 4 kb in brain, whereas a smaller transcript of about 3 kb was revealed in testis and liver. The brains from heterozygous mice expressed approximately 50% of the normal complement of the 4 kb transcript, whereas the homozygous mice expressed no detectable transcript of this size.

Heterozygous mice appear to have a higher than normal in utero mortality rate. Many appear normal morphologically and behaviorally, although these mice were shown to have histological evidence of hydrocephalus. Some of these mice survived to adulthood and were fertile. Hydrocephalus was externally obvious in many of the heterozygous mice within 4-8 weeks after birth. Some mice with obvious hydrocephalus developed rapid neurological deterioration and died within a few days.

Histologically in heterozygous mice, the hydrocephalus was apparent in the third and lateral ventricles. In addition, there was dilatation of the olfactory ventricles seen at the time of birth. Anatomically, examination revealed the absence or near absence of the subcommissural organ (SCO). This organ is thought to be critical for the maintenance of cerebrospinal fluid (CSF) flow through the aqueduct of Sylvius; ablation by various techniques leads to hydrocephalus (Perez-Figares, et al; *Microsc. Res. Tech.*, 52:591-601 [2001] herein incorporated by reference). The absence of this organ was detectable by routine histological staining. Upon antibody staining, using antibodies specific for the Reissner's fibers that comprise this organ, the staining of the heterozygous mice was lower than compared to wild-type mice. A small amount of antibody staining could be detected occasionally in the SCO region of the heterozygous mice, demonstrating that the molecular pathways leading to the production of the Reissner's fiber proteins is present, if underused, in the heterozygous animals.

The present disclosure also contemplates the generation of additional transgenic animals, including but not limited to mice, comprising an exogenous RFX4_v3 gene or homologs, mutants, or variants thereof. In preferred embodiments, the transgenic animal displays an altered phenotype as compared to wild-type animals. In some embodiments, the altered phenotype is the abnormal expression of mRNA for a RFX4_v3 gene as compared to wild-type levels of RFX4_v3 expression. Methods for analyzing the presence or absence of such phenotypes include Northern blotting, mRNA protection assays, and RT-PCR In other embodiments, the transgenic animals have a knock out mutation of the RFX4_v3 gene. In still further embodiments, transgenic animals have expression of a RFX4_v3 variant gene. In preferred embodiments, the transgenic animals display a congenital hydrocephalus phenotype.

In other embodiments, test compounds (e.g. a drug or other exogenous agent that is suspected of being useful to treat congenital hydrocephalus) and control compounds (e.g., a placebo) are administered to the transgenic animals and the control animals and the effects evaluated.

The transgenic animals can be generated via a variety of methods, including, but not limited to the method described above. In some embodiments, embryonic cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1-2 picoliters (p1) of DNA solution. The use of zygotes as a target for gene transfer has a major advantage in that in most cases the injected DNA will be incorporated into the host genome before the first cleavage (Brinster et al., *Proc. Natl. Acad. Sci. USA*, 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912). In other embodiments, the developing non-human embryo can be cultured in vitro to the blastocyst stage. During this time, the blastomeres can be targets for retroviral infection (Janenich, *Proc. Natl. Acad. Sci. USA*, 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., *Proc. Natl. Acad Sci. USA,* 82:6927 [1985]). Transfection is easily and efficiently obtained by culturing the blastomeres on a monolayer of virus-producing cells (Van der Putten, supra; Stewart, et al., *EMBO J.,* 6:383 [1987]). Alternatively, infection can be performed at a later stage. Virus or virus-producing cells can be injected into the blastocoele (Jahner et al., *Nature,* 298:623 [1982]). Most of the founders will be mosaic for the transgene since incorporation occurs only in a subset of cells, which form the transgenic animal. Further, the founder may contain various retroviral insertions of the transgene at different positions in the genome, which generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, *Mol. Reprod. Dev.,* 40:386 [1995]).

In other embodiments, the transgene is introduced into embryonic stem (ES) cells and the transfected stem cells are utilized to form an embryo. ES cells are obtained by culturing pre-implantation embryos in vitro under appropriate conditions (Evans et al., *Nature,* 292:154 [1981]; Bradley et al., *Nature,* 309:255 [1984]; Gossler et al., *Proc. Natl. Acad. Sci. USA,* 83:9065 [1986]; and Robertson et al., *Nature,* 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, see, Jaenisch, *Science,* 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination utilizes knock-out gene function or creates deletion mutants. Methods for homologous recombination are described in U.S. Pat. No. 5,614,396.

VII. Drug Screening Using RFX4_v3

The present disclosure provides methods and compositions for using RFX4_v3 as a target for screening drugs that can alter expression of congenital hydrocephalus.

A technique for drug screening provides high throughput screening for compounds having suitable binding affinity to RFX4_v3 peptides and is described in detail in WO 84/03564, incorporated herein by reference. Briefly, large numbers of different small peptide test compounds are synthesized on a solid substrate, such as plastic pins or some other surface. The peptide test compounds are then reacted with RFX4_v3 peptides and washed. Bound RFX4_v3 peptides are then detected by methods well known in the art.

Another technique uses RFX4_v3 antibodies, generated as discussed above. Such antibodies capable of specifically binding to RFX4_v3 peptides compete with a test compound for binding to RFX4_v3. In this manner, the antibodies can be used to detect the presence of any peptide that shares one or more antigenic determinants of the RFX4_v3 peptide.

The present disclosure contemplates many other means of screening compounds. The examples provided above are presented merely to illustrate a range of techniques available. One of ordinary skill in the art will appreciate that many other screening methods can be used.

In particular, the present disclosure contemplates the use of cell lines transfected with RFX4_v3 and variants or mutants thereof for screening compounds for activity, and in particular to high throughput screening of compounds from combinatorial libraries (e.g., libraries containing greater than $10^4$ compounds). The cell lines of the present disclosure can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding RFX4_v3 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., *Drug Discov. Today,* 3:323 [1998]; and Gonzales et al., *Drug. Discov. Today,* 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (see, e.g. Schroeder and Neagle, *J. Biomol. Screening*, 1:75 [1996]), and plate-reading systems. In some preferred embodiments, the response (e.g., increase in fluorescent intensity) caused by a compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product.

VIII Pharmaceutical Compositions Containing RFX4_v3 Nucleic Acid, Peptides, and Analogs The present disclosure further provides pharmaceutical compositions which may comprise all or portions of RFX4_v3 polynucleotide sequences, RFX4_v3 polypeptides, inhibitors, antagonists, enhancers or agonists of RFX4_v3 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present disclosure find use in treating diseases or altering physiological states. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this disclosure are useful for parenteral administration, such as intravenous, subcutaneous, intramuscular, intraperitoneal, intrathecal, or intraventricular. Therapeutic administration of a polypeptide intracellularly can also be accomplished using gene therapy as described above, or by intravenous administration of the pharmaceutical composition.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present disclosure, RFX4_v3 nucleotide and RFX4_v3 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present disclosure, the pharmaceutically acceptable carrier is pharmaceutically inert. In another embodiment of the present disclosure, RFX4_v3 polynucleotide sequences or RFX4_v3 amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton, Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the disclosure may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present disclosure can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present disclosure include compositions wherein the active ingredients are contained in an effective amount to achieve the intended purpose. For example, an effective amount of RFX4_v3 may be that amount that protects against congenital hydrocephalus. Determination of effective amounts is well within the capability of those skilled in the art, especially in light of the disclosure provided herein.

In addition to the active ingredients, these pharmaceutical compositions may contain suitable pharmaceutically acceptable carriers comprising excipients and auxiliaries, which facilitate processing of the active compounds into preparations that can be used pharmaceutically. The preparations formulated for oral administration may be in the form of tablets, dragees, capsules, or solutions.

The pharmaceutical compositions of the present disclosure may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the disclosure formulated in a pharmaceutical acceptable carrier may be prepared, placed in an appropriate container, and labeled for treatment of an indicated condition. For polynucleotide or amino acid sequences of RFX4_v3, conditions indicated on the label may include treatment of condition related to congenital hydrocephalus.

The pharmaceutical composition may be provided as a salt and can be formed with many acids, including but not limited to hydrochloric, sulfinuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the disclosure, the therapeutically effective dose can be estimated initially from cell culture assays. Then, preferably, dosage can be formulated in animal models (particularly murine models) to achieve a desirable circulating concentration range that adjusts RFX4_v3 levels.

A therapeutically effective dose refers to that amount of RFX4_v3 that ameliorates symptoms of the disease state. Toxicity and therapeutic efficacy of such compounds can be determined by standard pharmaceutical procedures in cell cultures, experimental animals or transgenic animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors, which may be taken into account, include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (see, U.S. Pat. Nos. 4,657,760; 5,206,344; or 5,225,212). Those skilled in the art will employ different formulations for RFX4_v3 than for the inhibitors of RFX4_v3.

The subject matter of the present disclosure is further illustrated by the following non-limiting Examples.

EXAMPLES

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); volume for volume (v/v).

Example 1

Development of RFX4_v3 Transgenic Mice

In this example, the development of the RFX4_v3 transgenic mice is described. RFX4_v3 transgenic mice were generated in which transgenic mice were created for the cardiac-specific expression of human CYP2J2, a cytochrome P450 arachidonic acid epoxygenase, using a mouse cardiac myosin promoter and a human growth hormone 3'-untranslated region (3'-UTR). The vector CYP2J2-pBS-αMHC-hGH, which contains the coding region of the CYP2J2 cDNA, αMHC promoter to drive cardiomyocyte-specific expression of the transgene and human growth hormone intron/polyA sequences to enhance transgene mRNA stability, was constructed. The linearized transgene was microinjected into pronuclei of single cell mouse embryos that were implanted into pseudopregnant female mice. Founder pups were identified by a combination of PCR and Southern blotting of tail genomic DNAs. Offspring from one of the founder lines (line Tr5) had congenital hydrocephalus. Details of the transgene construction and methods used in creating the transgenic mice are described below and have been described elsewhere (Yang et al, submitted for publication, 2003) herein incorporated by reference.

Example 2

Identification of the Transgene Insertion Site

This example describes methods used to identify the insertion site of the transgene into the mouse genome. A Universal GenomeWalker Kit (Clontech, Palo Alto, Calif.) was used to identify the mouse genomic sequences adjacent to the transgene insertion site. Briefly, genomic DNA from transgenic mice was digested with DraI, EcoRV, PvuII or StuI, and ligated to adaptors supplied by the manufacturer. PCR amplification of 3' adjacent sequences utilized the Advantage Genomic PCR Kit (Clontech), the universal adaptor primers AP1 and AP2, and the following nested gene-specific primers: 5'-ACAACTCTGCGATGGGCTCTGCTTT-3' (SEQ ID NO: 25) and 5'-CTGACCAATTTGACGGCGCTGCACA-3' (SEQ ID NO: 26). PCR products were cloned into the pCRII vector utilizing the TA Cloning Kit (InVitrogen/Life Technologies, Carlsbad, Calif.) and sequenced using the Big Dye Terminator Cycle Sequencing Ready Reaction Kit (Applied Biosystems, Foster City, Calif.). PCR amplification of 5' adjacent sequences was similarly performed using the following nested gene-specific primers: 5'-GGCCATTGTCAC-CACTCGTAA-3' (SEQ ID NO: 27) and 5'-CACAAG-TAAAGGCTAACGCGC-3' (SEQ ID NO: 28).

Example 3

Plasmids Utilized

In this example, the plasmids used in developing the RFX4_v3 transgenic mice and in identifying homologous RFX4_v3 transcripts in other non-mouse species are described. The plasmid insert containing the 7.5 kb transgene insert has been described elsewhere (Yang et al., submitted for publication, 2003); it consists of a 1.8 kb protein coding region of the human cytochrome P450 epoxygenase, driven by 5.5 kb of the mouse cardiac myosin promoter and contained 1.8 kb of the human growth hormone 3'-untranslated region. Plasmids containing the indicated human, mouse and zebrafish ESTs were obtained from the IMAGE consortium. A plasmid containing the putative protein coding region of the mouse RFX4_v3 was made by first using Platinum Pfx polymerase (InVitrogen/LifeTechnologies, Carlsbad, Calif.) to reverse transcribe total adult mouse brain RNA as the template. The resulting cDNA was then subjected to two rounds of nested PCR using primers based on the 5' and 3' sequences of apparent mouse brain RFX4 sequences from GenBank. The first pair of primers corresponded to bp 255-278 of accession number BB873367 and to bp 100-124 of accession number BB379807, and the second set of primers corresponded to 291-309 of accession number BB873367 and 99-78 of accession number BB379807. The resulting PCR product was sequenced using the ABI Prism dRhodamine Terminator Cycle Sequencing Ready Reaction Kit (Applied Biosystems, Foster City, Calif.).

Probes corresponding to the unique 5'-ends of mouse RFX4_1 and RFX4_3 were constructed by PCR amplification of reverse-transcribed mouse testis RNA or brain RNA, respectively. Reverse transcription was carried out using 1 µg of total RNA, an anchored oligo (dT) primer ($T_{18}VN$) and Superscript II RNase If Reverse Transcriptase (Invitrogen Life Technologies, Carlsbad, Calif.). PCR was performed using primers based on the sequence for human RFX4_v1 (accession number NM_032491) or the sequence for mouse RFX4_v3 contained in the mouse brain EST accession number BB595996. The forward primer for RFX4_v1 was 5'-AG-GTGGGAAGGCAGTTATGACAG-3' (SEQ ID NO: 16; corresponding to bases 1-23 of NM_032491) and the reverse primer was 5'-TCCGTGATATTTCTGCTTAGTGGGC-3' (SEQ ID NO: 17; bases 201-177). A second round of PCR was carried out with forward primer 5'-GGCAGTTATGA-CAGTTGAGAAGTAGTAG-3' (SEQ ID NO: 18; bases 10-37) and reverse primer 5'-CTGCTTAGTGGGCATCTC-GAATCTATC-3' (SEQ ID NO: 19; bases 189-163). The forward primer for mouse RFX4_v3 was 5'-TTTTGACGGGTTTGGCTTTG-3' (SEQ ID NO: 20; bases 118-137 of BB595996) and the reverse primer was 5'-TTCCTCCAGTAACCCACAATGC-3' (SEQ ID NO: 21; bases 447426). A probe corresponding to the unique 5'-end of RFX4_v2 was isolated by PCR amplification from mouse L cell genomic DNA using primers based on the sequence for human RFX4_v2 (accession number NM_002920). PCR was carried out using forward primer 5'-TGGAGAGGCCA-CAGCTGCTGG-3' (SEQ ID NO: 22; bases 1-21 of NM_002920) and reverse primer 5'-TCGAGGCCTGGTC-CTGTCGC-3' (SEQ ID NO: 23; bases 159-140). A second round of PCR was performed with 5'-CACAGCTGCTG-GCTTCCTGG-3' (SEQ ID NO: 24; bases 10-29) and the same reverse primer as in the first round of PCR. All three unique 5'-ends of RFX4_v1, RFX4_v2 and RFX4_v3 were sequenced using the ABI Prism dRhodamine Terminator Cycle Sequencing Ready Reaction Kit (Applied Biosystems, Foster City, Calif.).

A cDNA corresponding to human RFX4_v3 was cloned by screening a human fetal brain cDNA library (Stratagene) with the insert from the human IMAGE clone # 46678 (GenBank accession number H10145). The resulting cDNA clone was sequenced by dideoxynucleotide techniques (see above). A plasmid (GenBank accession number AI657628) containing a zebrafish EST sequence that predicted a protein closely related to the amino terminus of mouse and human RFX4_v3 was also obtained from the IMAGE Consortium and sequenced by dideoxynucleotide techniques.

Example 4

Histology and Antibody Staining of Brain Tissue

In this example, the histology and antibody staining of brain tissue from the RFX4_v3 transgenic mice are described. For histology, embryos and tissues from newborn or adult mice were fixed in Bouin's fixative for 1248 hours, depending on tissue size, and then cleared in 70% (v/v) ethanol. Tissues were then embedded in paraffin, sectioned and stained with hematoxylin and eosin by standard methods. For immunohistochemistry, paraffin sections were stained with an antibody (Rodriguez, et al., Cell Tissue Res., 237:427-41 [1984]) to Reissner's fibers (RF) within the SCO, as described previously for a different antibody (Blackshear et al., Dev. Brain Res., 96:62-75 [1996]). The anti-RF antibody was a gift from Dr. E. M. Rodriguez, Instituto de Histologia y Patologia, Facultad de Medicina, Universidad Austral de Chile, Valdivia, Chile.

Example 5

In situ Hybridization Histochemistry

This example describes methods for in situ hybridization using brain tissue from the RFX4 v3 transgenic mice. Embryos were dissected in PBS and fixed in 4% (w/v) paraformaldehyde/PBS at 4° C. Specimens for whole-mount in situ hybridization were gradually dehydrated in methanol/PBS and stored in 100% methanol at −80° C. Specimens for in situ hybridization on frozen sections were cryoprotected in 30% sucrose and embedded in TissueTek (Sakura), and 20 µm thick sections were obtained using a cryostat. Whole mount and section in situ hybridizations were performed according to the methods of Wilkinson and Tsuchida et al., respectively (Wilkinson et al., 1992). In *In situ hybridization: a practical approach*, (ed. D. G. Wilkinson), pp. 75-83. Oxford: IRL Press; Tsuchida et al., (1994). *Cell* 79, 957-70). The probes used and their sources were as follows: RFX4 (this paper); Otx2 (Antonio Simeone); Bf1 (Eseng Lai); Fgf8 (Gail Martin); Msx2 (Betham Thomas); Wnt3a and Wnt7b (Andrew MacMahon); Lhx2 (Heiner Westphal); Pax6 and Six3 (Peter Gruss); Emx1, Dlx2 and Nkx2.1 (J.L.R.R.'s laboratory).

Example 6

Evaluation of Transgenic Mice

Figure 7:
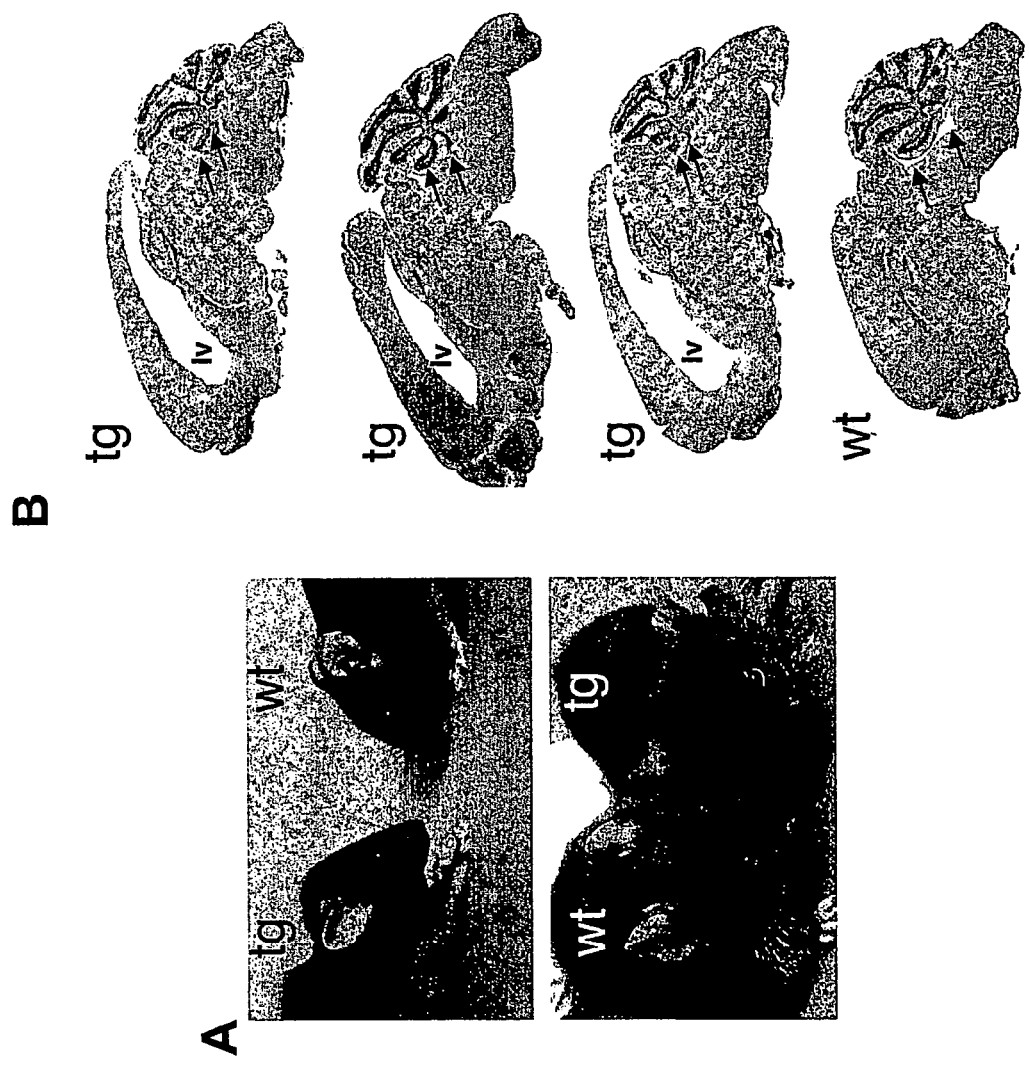
FIG. 7 is a set of digital images showing hydrocephalus in adult TG mice.

This example describes the results of evaluation of the transgenic mice. A large percentage of mice in one (Tr5) of six transgenic (TG) lines exhibited head swelling followed by rapid neurological deterioration and death in young adulthood. The external swelling was apparent by the increased convexity of the head, and the lateral displacement of the ears (FIG. 7A). Histological examination of the brains of symptomatic adult mice revealed severe hydrocephalus in the anterior brain, with extreme dilatation of the lateral ventricles but no apparent effect on the fourth ventricle (FIG. 7B). Although many of the mice developed the severe form of the syndrome within the first two months of life, sufficient mice survived to propagate the line. Nonetheless, examination of the brains of successful adult breeders showed severe hydrocephalus, with extreme lateral ventricle dilatation and the formation of false ventricles near the external capsule, as well as midline structural disruption by the extreme hydrocephalus. These findings were compatible with an obstructive hydrocephalus, and were consistent with the form of hydrocephalus seen with stenosis of the aqueduct of Sylvius, or aqueductal stenosis. It should be noted that CYP2J2 transgene expression did not occur in brains from the TG mice, as evaluated with two different CYP2J2-specific antibodies on western blots.

Figure 8:
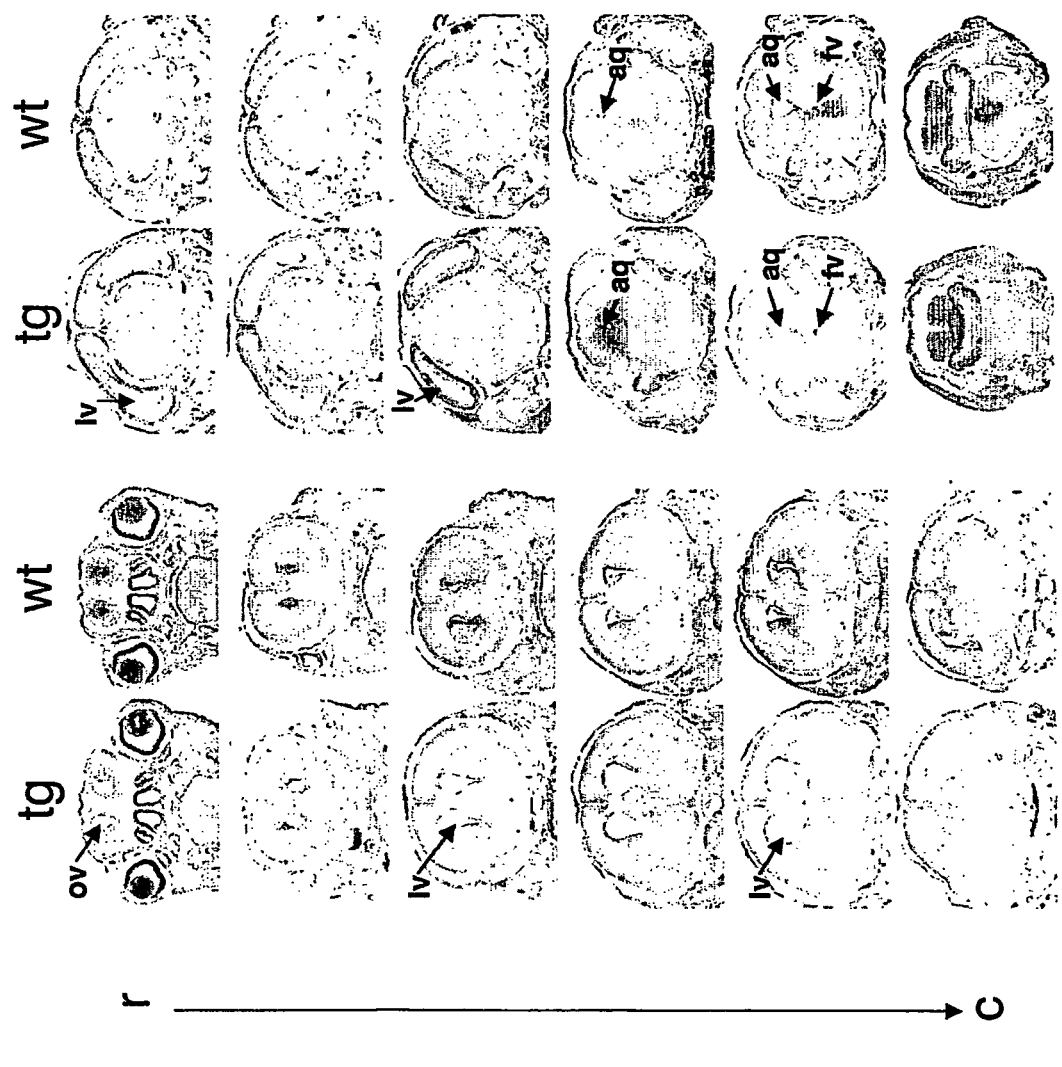
FIG. 8 is a set of digital images showing hydrocephalus in newborn TG mice. Serial rostral (R) to caudal (C) coronal sections, stained with hematoxylin and eosin, from newborn (P0.5) TG and WT littermates are shown, with each pair of sections representing approximately the same coronal plane. Note the extreme hydrocephalus apparent in the olfactory ventricles (OV) and the lateral ventricles (LV) of the TG compared to the WT mouse. In the more posterior sections, note the similar appearance of the aqueduct of Sylvius (Aq) and the fourth ventricle (FV) in the WT and TG mice.

Examination of TG mice from the Tr5 line at the time of birth (P0.5) showed that severe hydrocephalus was present in all mice harboring the transgene, indicating that the hydrocephalus was congenital. In contrast, none of the wild-type (WT) littermates had hydrocephalus. The hydrocephalus was most apparent in the olfactory and lateral ventricles, with apparent sparing of the fourth ventricle (FIG. 8). These data support the possibility of a congenital obstruction in the aqueduct of Sylvius.

Examination of the aqueduct in serial coronal sections from a TG mouse and its WT littermate at P0.5 showed the apparent absence of the subcommissural organ (SCO) in the transgenic mice (FIG. 9A). This organ produces Reissner's fibers, and both the organ and the fibers have been shown to be important for the patency of the aqueduct, in that destruction of the SCO leads to obstructive hydrocephalus (Perez-Figares et al., 2001). Antibodies specific to Reissner's fibers (Rodriguez et al., 1984; Rodriguez et al., 2001; Rodriguez et al., 1998) strongly and specifically labeled the SCO from the WT mice (FIG. 9B), but this label was generally not detected in the same anatomical region in the TG mice. Rarely, a small amount of staining could be found in sections from the TG mice at the anatomical location that should have contained the SCO (FIG. 9B); however, this staining was always markedly less than that seen in the WT mice. Although the SCO appeared to be largely absent in the TG mice, other midline structures, such as the pineal body and posterior commissure, were present and appeared to be anatomically normal.

We next examined the birth statistics from this line of transgenic animals for Mendelian frequencies. For crosses in which TG mice were bred to WT mice, there were 6.7+/−0.4 (SE) live births per litter based on data from 47 litters. Of 315 pups born, 46% were TG and 54% were WT. For comparison, TG mice originating from another founder line crossed with WT mice resulted in 7.0+/−0.4 (SE) live births per litter based on data from 45 litters, with 52% of 317 pups genotyped as TG. These data suggest minimal if any prenatal loss of TG pups, despite the presence of congenital hydrocephalus. In the TG mice, severe hydrocephalus requiring euthanasia developed in about 75% of the mice at an average age of 47+/−3 days (range 24-84 days). There was no significant difference in frequency of hydrocephalus between males and females. The hydrocephalus phenotype has persisted in TG mice through nine generations.

All other non-brain tissues of the TG mice appeared to be histologically normal.

Example 7

Identification of Genomic Sequences Flanking the Transgene

This example describes the identification of genomic sequences flanking the transgene. Because it appeared that the transgene had interrupted the coding or regulatory regions of an important gene, the mouse genomic sequences flanking the transgene were identified. Using PCR based on 5' and 3' transgene sequences, there were at least two tandem copies of the 7.5 kb transgene in genomic DNA from the TG mice, indicating that the potential genomic interruption was at least 15 kb in size; Southern analysis using a transgene-specific probe indicated that there was only one copy of this concatenated transgene in the mouse genome. Using the "GenomeWalker" technique with genomic DNA from the TG mice and transgene-specific oligonucleotide primers, both the 5' and 3' flanking genomic sequences into which the transgene had been inserted were identified. When these sequences were compared to the mouse genomic sequences in the GenBank trace archives, the transgene insertion site was identified as between bp 528 and 529 in gnl|ti|13973384 and between bp 171 and 172 in gnl|ti|84074979. The 5' and 3' flanking sequences identified by the GenomeWalker technique were contiguous in the normal mouse genomic sequences in the trace archives, indicating that the transgene insertion was not accompanied by a genomic deletion, as has been seen in some recent examples of accidental transgenic insertional mutagenesis (Durkin et al, (2001) *Genomics* 73, 20-7; Overbeek et al., (2001) *Genesis* 30, 26-35). Southern analysis using a 3'-insertion site-specific probe demonstrated the presence of single novel bands in restriction enzyme-digested DNA from the transgenic mice, confirming a single transgene insertion site at this location (FIG. 10A).

The flanking sequences identified by the GenomeWalker approach were merged with the available mouse genomic sequence from the trace archives to form a small contig; this did not recognize any cDNAs or expressed sequence tags (ESTs) in the database at that time. Therefore, the assembled mouse contig was used to search the human genome sequences then available in GenBank, using blastn. The mouse sequence was highly related (4e-28) to a human genomic sequence corresponding to a portion of human chromosome 12 (accession number NT_009720.8). When this small region of human genomic sequence was analyzed for expressed sequences, it did not match any deposited in GenBank. However, when a much larger amount of human genomic DNA from this locus was used to search for expressed sequences, genomic DNA within 200 kb of the human sequence corresponding to the transgene insertion site was found to contain all of the exons of two distinct cDNAs in GenBank that correspond to two forms of the human winged helix protein RFX4: One is represented by GenBank accession number NM_032491, referred to as RFX4 variant transcript 1, or RFX4_v1, and corresponds to protein accession number NP_115880; the other is represented by GenBank accession number NM_002920 and is referred to as RFX4 variant transcript 2, or RFX4_v2, corresponding to protein accession number NP_002911. See the nomenclature recommendations of the Human Genome Nomenclature committee for the conventions described here.

According to the mouse—human alignments, the site of the transgene insertion within the mouse genome was at a corresponding region within the human chromosomal 12 sequence that would be within the intron between exons 13 and 14 of RFX4_v1 (see below); it would not have affected the exon arrangements of RFX4_v2.

Using PCR primers based on the inserted transgene and the neighboring endogenous mouse genomic DNA, the WT (+/+) and transgene-interrupted alleles (+/−for one allele disrupted, −/− for both alleles disrupted) were found to be readily distinguished in a litter of newborn mice from interbred TG mice (FIG. 10B).

To examine the possibility that the transgene insertion had in some way interfered with the expression of a full-length mouse RFX4 transcript in brain, northern blots from brains of neonatal+/+, +/−and −/− mice were probed with a mouse brain EST cDNA clone (IMAGE # 763537, GenBank accession numbers AA285775 and AI462920) that was highly related (e-124 over 284 aligned bases) to the 3'-end of the human cDNA for RFX4_v1. Brains from the +/+mice expressed a prominent band of ~4 kb that are referred to as RFX4 variant transcript 3, or RFX4_v3 (FIG. 10C; see below). Brains from the +/−mice expressed approximately 50% of the normal complement of this transcript, whereas the brains from the −/− mice expressed no detectable transcript of this size (FIG. 10C). Probing the same blot with an actin cDNA demonstrated that gel loading was similar in the three lanes (FIG. 10C). Similar results were obtained in three separate experiments. There was no evidence for the expression of a truncated mRNA in the brain samples from either the +/−or −/− mice. These studies confirmed that an mRNA species of ~4 kb that was recognized by a probe derived from putative mouse 3' RFX4_v1 sequences was decreased in amount in brains of the +/−mice, and absent from the brains of the −/− mice. These data suggested that the insertion of the transgene interfered with the expression of the putative brain RFX4_v3 transcript.

Using the same probe to examine the tissue-specific and developmental expression of this RFX4 transcript, high-level expression of a slightly smaller transcript was found in normal adult testis, and lower level expression of a considerably smaller transcript was found in liver (FIG. 10D). The largest species, corresponding to the apparent brain-specific transcript labeled RFX4_v3 in FIG. 10D, was the only one detected in whole embryos early in development (FIG. 10E). These data suggested that an apparently brain-specific isoform of RFX4 in the adult was highly expressed in the whole embryo during early development, initially appearing between embryonic day (E) 7.5 and 9.5 (FIG. 10E).

Example 8

Identification of the RFX4_v3 Transcripts and Proteins

This example describes the results obtained from identification of the RFX4_v3 transcripts and proteins. Using primers based on mouse brain EST sequences that contained internal sequences highly related to the human RFX4 cDNAs in GenBank, PCR and an adult mouse brain cDNA library were used to generate a ~3 kb plasmid insert that was then sequenced. This cDNA has been designated RFX4 transcript variant 3 (RFX4_v3), and the mouse sequence was deposited in GenBank (accession number AY102010). When this sequence was merged with all available 5' and 3' mouse ESTs from GenBank, the resulting transcript was 3952 b, closely approximating the tanscript size seen on northern blots. In addition, a cDNA sequence was deposited in GenBank on Dec. 5, 2002 (GenBank accession number AK034131.1) that was 3535 b in length; over this length, it was more than 99% identical to the putative RFX4_v3 full-length transcript described above, and include the entire putative protein coding region. This cDNA was isolated from an adult male mouse diencephalon library and confirms the existence in brain of at least the protein coding region of our predicted full length RFX4_v3 transcript.

Similar probes as used to generate the northern blots shown in FIG. 10 were then used to screen a human brain cDNA library, and positive inserts were sequenced. This cDNA sequence has been deposited in GenBank as human RFX4_v3 (accession number AY102009; SEQ ID NO: 7). The predicted unique mouse amino terminal protein sequence (see below) also was used to search the non-human, non-mouse ESTs in GenBank, and a zebrafish EST clone (accession number AI657628) with a nearly identical predicted amino-terminal protein sequence was obtained from the IMAGE consortium and sequenced. This sequence is referred to as zebrafish RFX4_v3, and the complete insert cDNA sequence has been assigned accession number AY102011 (SEQ ID NO: 9).

An alignment of these three predicted amino acid sequences is shown in FIG. 6. There was 96% amino acid identity between the predicted mouse and human proteins, and 83% amino acid identity between the predicted human and zebrafish proteins. The alignment also illustrates several of the characteristic domains of the RFX proteins that are highly conserved in all three orthologues, i.e., the DNA binding domain, boxes B and C, and the dimerization domain (Morotomi-Yano et al., (2002) *J Biol Chem* 277, 836-42).

Human chromosome 12 sequence was then re-searched with the mouse and human cDNA sequences, and the exons that contributed to the novel human RFX4_v3 isoform described here, in addition to those described above that corresponded to the two previously described human cDNAs were identified. The results of this analysis are shown in FIG. 2. The two previously described human RFX4 cDNAs are composed of both unique and shared exons. In the case of the cDNA represented by accession number NM_002920 (RFX4_v2), the first five exons (shown in FIG. 2) correspond to five exons within the 90 kb interval between bp 390,000-480,000 of the genomic clone NT_009720.8 (in reverse complement orientation). The next nine exons and part of a tenth are common to the other version of RFX4 in GenBank (RFX4_v1), represented by the cDNA NM_032491. These 10 exons are derived from coding sequences in the genomic clone NT_009720.8 between 340,000 and 400,000. As shown in FIG. 2, the final (15$^{th}$) exon of RFX4_v2 contains a polyadenylation sequence that allows for final processing of the mature mRNA.

The other human cDNA, RFX4_v1 (NM_032491), contains a 5' exon that is encoded by genomic sequences in NT_009720.8 that are located between the exons 5 and 6 of RFX4_v2 (FIG. 2) and is unique to that cDNA. RFX4_v1 then shares 10 exons with RFX4_v2, followed by three unique 3' exons. These last three unique exons are found within the interval between bp 315,000-325,000 of the genomic clone NT_009720.8. Remarkably, exon 12 from RFX4_v1 is apparently spliced into exon 15 of RFX4_v2, resulting in the novel 3' end of RFX4_v1 and a different poly A tail. The displaced sequence in RFX4_v2 is represented as exon 15B in FIG. 2.

The exon pattern that corresponds to the mouse and human RFX4_v3 mRNAs and proteins is illustrated at the bottom of FIG. 2. A novel exon derived from a sequence between 480,000 and 500,000 of NT_009720.8 was used to form the first 14 amino acids at the amino terminus (FIG. 2). The next four exons, 2-5, are composed of the four exons of the same number from RFX4_v2; exon 1 of RFX4_v2 is not present in the RFX4_v3 cDNA. The middle of the RFX4_v3 cDNA and protein are formed by the 10 exons held in common between RFX4_v1 and RFX4_v2. The carboxyl terminus of RFX4_v3 is composed of the three carboxyl-terminal exons present only in RFX4_v1. Thus, the novel RFX4_v3 isoform described here is composed of a unique arrangement of 18 exons derived from almost 200 kb of human genomic sequence. One exon (the first) is unique to this sequence; exons 2-5 are shared with RFX4_v2; exons 6-15 are shared with both RFX4_v1 and RFX4_v2; and exons 16-18 are shared with only RFX4_v1.

The site of transgene interruption is also illustrated in FIG. 2. The >15 kb transgene was inserted into the intron between exons 17 and 18 of RFX4_v3, within the carboxyl-terminal end of the protein coding region, and presumably interferes with splicing of the final exon and generation of an intact mature mRNA. No evidence has been found to date that a stable truncated mRNA species results from this transgene insertion.

Specific cDNA probes corresponding to unique 5' sequences were designed and cloned for each of the three RFX4 transcript variants RFX4_v1, v2 and v3. These were then used to probe northern blots of RNA from brains of E18.5 mice as well as from adult testes, liver and brain. A probe that spanned regions common to the RFX4_v1, v2 and v3 transcripts hybridized to two major mRNA species in testes, a single transcript of intermediate size in liver, and a single transcript of the largest size (~4 kb) in RNA from adult brain. This probe only hybridized to the 4 kb RNA species in brains from E18.5 mice; the amount of hybridization of this probe decreased from the +/+ to the +/−mouse brain, and was undetectable in brain from the −/− sample. When similar blots were hybridized with a probe specific for v1 and v3, only the larger of the two testes transcripts (v1) was detected, while the largest transcript (v3) was again identified in the adult brain sample and in the brain from E18.5+/+ fetal mice. Again, the expression of the transcript hybridizing to this probe decreased with decreasing allelic dosage.

The identities of the various transcripts were determined by the use of transcript-specific probes, which confirmed the assignments of the v1 and v2 transcripts in testis, and the complete absence of hybridization of either probe to transcripts from normal adult brain (FIG. 11), or brain from E18.5 mice of the +/+, +/− and −/−. There was no evidence of compensatory expression of either the v1 or v2 transcripts in the E18.5 brains of the −/− mice. The v3-specific probe was used to confirm the identity of the single, large transcript in brain as RFX4_v3, and also confirmed its allelic dose-related expression in E18.5 mouse brain (FIG. 11). These data indicate that the v3 transcript variant is the only form significantly expressed in the adult and fetal brain, and also confirmed it as the transcript variant expressed in the whole embryo and brain in earlier development (see FIG. 10E).

The apparently liver-specific transcript may represent a "RFX4_v4", or it could represent cross hybridization of the longer probes to another member of the RFX transcript family that is highly expressed in liver.

Example 9

Analysis of RFX_v3 Transcript Expression During Development

This example describes the pattern of RFX4_v3 transcript expression in mouse embryos, as analyzed using RNA in situ hybridization. A probe was used that contained sequences specific to both RFX4_v1 and v3. RFX4_v3 RNA was found primarily in the brain where its regional expression was highly dynamic during development. At E8.5, RFX4_v3 expression was detected in most of the neural plate, but its expression was excluded from the presumptive forebrain region (FIG. 12A, B). By E9.5, most of its expression encompassed two large regions: the caudal diencephalon/mesencephalon and the spinal cord (FIG. 12C). The rostral limit of the diencephalic expression approximated the zona limitans; the only expression extending anterior of this boundary was in the caudodorsal telencephalon (FIG. 12C).

At E10.5, RFX4 v3 expression extended throughout the neural tube (FIG. 12D-F). In the telencephalon, its expression was limited to the cerebral cortex. Expression in the telencephalic dorsal midline was not detectable (FIG. 12F-H, arrowheads), and remained negative from that time onward during development. Thus, expression in the telencephalic roof plate was temporally restricted to the period just after neural tube closure (~E9.5).

Transient RFX4 v3 expression appeared in the central retina. The lateral optic stalks also exhibited RFX4_v3 expression (FIG. 12H), while the medial optic stalks showed expression at later stages (FIG. 12K).

From E12.5 to birth, the neuroepithelium and later the ependyma of most of the neural tube expressed variable levels of RFX4_v3 transcripts. For example, in the cerebral cortex, RFX4_v3 was expressed in a dorsal to ventral gradient (FIG. 12K). The majority of roof plate derivatives of the central nervous system, including most of the circumventricular organs, had turned off RXF4_v3 expression by this stage (for example, the epiphysis, and the choroid plexus of the lateral and fourth ventricles in FIG. 12L, M). A striking exception to this pattern was the expression of RFX4_v3 in the region of the developing SCO found in the caudal diencephalon, where there was strong expression from E14.5 to birth (FIG. 13C, E-G).

The only RFX4_v3 positive structures noted outside of the central nervous system were the trigeminal and facial/vestibular ganglia (FIG. 12I) and the anterior pituitary (FIG. 13B).

Example 10

Phenotype of RFX4_v3-deficient Mice

This example describes the phenotype of RFX4_v3-deficient mice. Surviving TG mice, which are referred to as RFX4_v3 +/− mice, were interbred to generate −/− mice. Ten pregnant+/− mice were allowed to carry to term and deliver; the average litter size of these pregnancies was 5.3+/− 0.6, which was significantly smaller than litters from a control line 7.0+/−0.4 (p=0.022). Of 53 pups born, 19 (36%) were WT, 28 (53%) +/−, and 6 (11%) −/−, suggesting substantial intrauterine or perinatal loss of the −/− pups. All of the −/− pups born died within an hour of birth. Seven additional litters were obtained between E8 and E18. The average size of those litters was 8.7+/−0.5, which was not significantly different from control litters. Of 61 pups obtained, there were 10 (16%) +/+, 36 (59%) +/− and 15 (25%) −/−, indicating no excess intrauterine mortality.

The brains of the −/− mice at the time of birth and at E16.5 were grossly dysmorphic. Thus, the −/− mice were examined at an earlier developmental stage, E12.5. The phenotype at this age was striking (FIG. 14). Externally, there were clear abnormalities of head appearance, although the position of the eyes, vibrissae and other facial structures appeared relatively normal (FIG. 14A). Coronal sections suggested that dorsal structures in the rostral brain were hypoplastic and lacked morphological differentiation of medial and paramedial dorsal structures. This was most striking in the forebrain and midbrain (FIG. 14B), but abnormalities persisted into the hindbrain and spinal cord. As in the hemizygotes, the anatomy of the rest of the body in the E12.5 −/− embryos was apparently normal.

To characterize the patterning of the mutant brains, the expression of genes that play important roles in regionalization was analyzed (Marin and Rubenstein (2002) In *Mouse Development*, (ed. J. Rossant and P. Tam), pp. 75-106: Academic Press). The analysis was focused mainly on the telencephalon of E12.5 −/− embryos (FIG. 15). The lateral walls of the telencephalic vesicles primarily consist of the basal ganglia (rostroventral) and the cerebral cortex (caudodorsal). The rostral and rostrodorsal midline is constituted by the commissural plate and adjacent parts of the septal area; the caudodorsal midline consists of the choroid plexus and the cortical hem. The cortical hem is a Wnt- and BMP-rich signaling center in the dorsomedial telencephalon that has been shown to be crucial in cortical development (Furuta et al., (1997) *Development* 124, 2203-12; Galceran et al., (2000) *Development* 127, 469-82; Grove et al., (1998) *Development* 125, 2315-25; Lee et al., (2000) *Development* 127, 457-67).

Expression of the telencephalic marker Foxg1 (Bf1) was maintained in the cortex and basal ganglia of RFX4_v3 mutants. The expression of markers specific for midline structures, the cerebral cortex and the basal ganglia revealed that the principal telencephalic defects in RFX4_v3 mutants involved severe hypoplasia of the dorsal midline and adjacent cerebral cortex (FIG. 15). The lack of dorsal midline structures was demonstrated by the loss of Wnt3a, Wnt7b and Bmp4 expression in the hem (FIG. 15E, F and not shown) and the reduction of Msx2 expression in the hem and choroid plexus (FIG. 15D). The cerebral cortex was present, based on the expression of Wnt7b, Enix1, Pax6 and Lhx2 (FIG. 15F-I); however, it was severely hypoplastic. Despite the severe hypoplasia, the cortex did produce post-mitotic cells, based on the mantle zone expression of Wnt7b (FIG. 15F).

In wild-type mice, Lhx2 and Emx1 are expressed in a dorsoventral gradient in the cortical neuroepithelium. In the RFX4_v3 mutants, Lhx2 and Emx1 expression levels were similar to those seen in the ventral part of the normal cortex, suggesting that dorsal parts of the cortex were missing (FIG. 15G, I). An Emx1-negative, Lhx2-positive territory intercalated between the striatum and the prospective piriform cortex, which develops into parts of the claustroamygdaloid complex (Puelles et al, (2000) *J Comp Neurol* 424, 409-38; Yun et al., (2001) *Development* 128, 193-205), was maintained in the mutants (FIG. 15G, I). Finally, Pa6 is normally detected in a ventrodorsal gradient In the mutants, the ventral stronger-expressing area was detected (FIG. 15H). Thus, the most ventral subdivisions of the cortex, located adjacent to the striatum, i.e., the piriform cortex and parts of the claustroamygdaloid complex, seemed to be correctly specified, while the most medial cortical subdivisions, located adjacent to the cortical hem, i.e., the hippocampus and the neocortex, are either severely reduced, lost, or mis-specified.

The basal ganglia are formed in mammals by the lateral ganglionic eminence, which develops into the striatum, and the medial ganglionic eminence, which develops into the pallidum (Marin and Rubenstein (2002) In *Mouse Development*, (ed. J. Rossant and P. Tam), pp. 75-106: Academic Press). In the mutants, while the size of the basal ganglia was disproportionately large compared to the cortex, it is unclear whether or not there was an absolute increase in the sizes of the lateral and medial ganglionic eminences. The RFX4_v3 mutants exhibited normal expression of Dlx2 and Six3 transcription factors in the lateral and medial ganglionic eminences (FIG. 15J, K). Expression of Otx2, Fgf8 and Six3 in the septum, a basal ganglia-related structure, was detected as well (FIG. 15B, C, J). In addition, the specific expression of the transcription factor Nkx2.1 in the medial ganglionic eminence and ventral septum was apparently normal in the mutants (FIG. 15L).

Example 11

Other Embodiments

In some embodiments, an isolated and purified nucleic acid comprises a sequence encoding a protein selected from the group consisting of SEQ ID NOS: 5, 7 and 9. Alternatively, the nucleic acid sequence is selected from the group consisting of SEQ ID NOS: 5, 7, and 9 and variants thereof that are at least 90% identical. In some embodiments, the present disclosure provides nucleic acid sequence selected from the group consisting of SEQ ID NOS: 5, 7, and 9 and variants thereof that are at least 80% identical. In some embodiments, the nucleic acid sequence is selected from the group consisting of SEQ ID NOS: 5, 7, and 9 and variants thereof that are at least 70% identical. The nucleic acid sequence may be operably linked to a heterologous promoter (e.g., SEQ ID NOS: 11 or 12). The nucleic acid sequence may be contained within a vector, and the vector may be present within a host cell.

In other embodiments, an isolated and purified nucleic acid sequence hybridizes under conditions of low stringency to a nucleic acid selected from the group consisting of SEQ ID NOS: 5, 7, and 9. In some embodiments, the nucleic acid sequence encodes a protein (e.g., SEQ ID NOS: 6, 8, or 10, or is included in a vector that includes the nucleic acid sequence. The vector may be within a host cell, and the host cell may, for example, be located in an organism such as a plant, an animal, or a prokaryote.

In yet other embodiments, the protein is selected from the group consisting of SEQ ID NOS: 6, 8, and 10 and variants thereof that are at least 90% identical to SEQ ID NOS: 6, 8, or 10 and wherein the protein has at least one activity of RFX4 v3. In other embodiments, the present disclosure provides a protein selected from the group consisting of SEQ ID NOS: 6, 8, and 10 and variants thereof that are at least 80% identical to SEQ ID NOS: 6, 8, or 10 and wherein the protein has at least one activity of RFX4_v3. In other embodiments, the present disclosure provides a protein selected from the group consisting of SEQ ID NOS: 6, 8, and 10 and variants thereof that are at least 70% identical to SEQ ID NOS: 6, 8, or 10 and wherein the protein has at least one activity of RFX4_v3.

Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure, which are obvious to those skilled in the relevant fields, are intended to be within the scope of the following claims.

We claim:

1. An isolated nucleic acid molecule encoding a RFX4_v3 polypeptide, wherein the polypeptide comprises:
   a) an amino acid sequence at least 99% identical to the amino acid sequence of SEQ ID NO: 8;
   b) an amino acid sequence at least 95% identical to the amino acid sequence of SEQ ID NO: 8, wherein fourteen consecutive amino acids within the N-terminal sequence of the polypeptide are identical to residues 1-14 of SEQ ID NO: 8; or
   c) the amino acid sequence of SEQ ID NO: 8,
wherein the polypeptide in a), b), or c) has RFX4_v3 activity.

2. An isolated nucleic acid molecule encoding a RFX4_v3 polypeptide, comprising (i) a nucleic acid sequence at least 99% identical to the nucleic acid sequence of SEQ ID NO: 37, or (ii) a nucleic acid sequence at least 95% identical to the nucleic acid sequence of SEQ ID NO: 38 or SEQ ID NO: 39.

3. The nucleic acid molecule of claim 1 operably linked to a heterologous promoter.

4. The nucleic acid molecule of claim 3, wherein the heterologous promoter comprises SEQ ID NO: 11 or SEQ ID NO: 12.

5. A vector comprising the nucleic acid molecule of claim 1.

6. An in vitro host cell transformed with the vector of claim 5.

7. The in vitro host cell of claim 6, wherein the host cell is a plant cell, an animal cell, or a prokaryotic cell.

8. A composition comprising the nucleic acid molecule of claim 1.

9. An isolated nucleic acid molecule that hybridizes under conditions of high stringency to a polynucleotide consisting of nucleotides 1-42 of a nucleic acid sequence selected from the group consisting of SEQ ID NO: 37, SEQ ID NO: 38, and SEQ ID NO: 39, wherein the isolated nucleic acid molecule comprises at least 20 contiguous nucleotides of nucleotides 1-42 of SEQ ID NO:37, SEQ ID NO: 38, or SEQ ID NO: 39, and wherein the isolated nucleic acid molecule encodes a RFX4_v3 polypeptide at least 99% identical to the amino acid sequence of SEQ ID NO: 8, SEQ ID NO: 6, or SEQ ID NO: 10, respectively.

10. An isolated nucleic acid molecule comprising a nucleic acid sequence encoding a RFX4_v3 polypeptide comprising SEQ ID NO: 6, SEQ ID NO: 8, or SEQ ID NO: 10.

11. A vector comprising the nucleic acid molecule of claim 9.

12. An in vitro host cell transformed with the vector of claim 11.

13. The in vitro host cell of claim 12, wherein the host cell is a plant cell, an animal cell, or a prokaryotic cell.

14. A method for producing a variant RFX4_v3 polypeptide, wherein the method comprises:
   mutagenizing a wild-type nucleic acid sequence having SEQ ID NO: 37;
   expressing the mutagenized nucleic acid sequence; and
   screening the variant RFX4_v3 polypeptide for a RFX4_v3 activity, wherein the variant RFX4_v3 polypeptide comprises:
   a) an amino acid sequence at least 99% identical to the amino acid sequence of SEQ ID NO: 8;
   b) an amino acid sequence at least 95% identical to the amino acid sequence of SEQ ID NO:8, wherein fourteen consecutive amino acids within the N-terminal sequence of the polypeptide are identical to residues 1-14 of SEQ ID NO: 8; or
   c) the amino acid sequence of SEQ ID NO: 8,
wherein the polypeptide in a), b), or c) has RFX4_v3 activity.

15. A composition comprising the isolated nucleic acid molecule of claim 9 or its full-length complementary sequence.

16. The isolated nucleic acid molecule of claim 9, wherein the isolated nucleic acid molecule hybridizes under conditions of high stringency to the polynucleotide consisting of nucleotides 1-42 of SEQ ID NO: 37.

17. A method for detecting a polynucleotide molecule in a biological sample, comprising:
hybridizing the polynucleotide molecule in the biological sample to an isolated nucleic acid molecule comprising the sequence of SEQ ID NO: 37, SEQ ID NO: 38, or SEQ ID NO: 39, to produce a hybridization complex, wherein the polynucleotide molecule hybridizes under conditions of high stringency to nucleotides 1-42 of SEQ ID NO: 37, SEQ ID NO: 38, or SEQ ID NO: 39;
detecting the hybridization complex, wherein the presence of the hybridization complex indicates the presence of the polynucleotide molecule encoding RFX4_v3 in the biological sample, thereby detecting the polynucleotide molecule in the biological sample.

18. The method of claim 17, wherein the polynucleotide molecule hybridizes to the sequence of SEQ ID NO: 37.

19. The method of claim 17, further comprising amplifying the polynucleotide molecule prior to hybridizing with said isolated nucleic acid molecule.

20. A pharmaceutical composition, comprising:
a) a therapeutically effective amount of the isolated nucleic acid molecule of claim 1; and
b) a pharmaceutically acceptable carrier.

21. The isolated nucleic acid molecule of claim 1, wherein the polypeptide comprises an amino acid sequence at least 99% identical to the amino acid sequence of SEQ ID NO: 8.

22. The isolated nucleic acid molecule of claim 1, wherein the RFX4_v3 polypeptide inhibits the phenotypic expression of congenital hydrocephalus.

23. The isolated nucleic acid molecule of claim 1, wherein the polypeptide encoded by the nucleic acid molecule is bound by a RFX4_v3 specific antibody.

24. An isolated nucleic acid molecule encoding a RFX4_v3 polypeptide having RFX4_v3 activity, wherein the polypeptide comprises SEQ ID NO: 8.

25. An isolated nucleic acid molecule encoding a RFX4_v3 polypeptide having RFX4_v3 activity, wherein the isolated nucleic acid molecule comprises SEQ ID NO: 37.

26. The isolated nucleic acid molecule of claim 1, wherein the isolated nucleic acid molecule encodes a RFX4_v3 polypeptide comprising an amino acid sequence at least 95% identical to the amino acid sequence of SEQ ID NO: 8, wherein fourteen consecutive amino acids within the N-terminal sequence of the polypeptide are identical to residues 1-14 of SEQ ID NO: 8.

27. The nucleic acid molecule of claim 2, wherein the nucleic acid sequence is at least 99% identical to the nucleic acid sequence of SEQ ID NO: 38.

28. The nucleic acid molecule of claim 27, wherein the nucleic acid sequence comprises SEQ ID NO: 38.

29. The nucleic acid molecule of claim 2, wherein the nucleic acid sequence is at least 99% identical to the nucleic acid sequence of SEQ ID NO: 39.

30. The nucleic acid molecule of claim 29, wherein the nucleic acid sequence comprises SEQ ID NO: 39.

31. An isolated nucleic acid molecule encoding a RFX4_v3 polypeptide, consisting of the nucleic acid sequence of SEQ ID NO: 37, SEQ ID NO: 38, or SEQ ID NO: 39.

* * * * *

UNITED STATES PATENT AND TRADEMARK OFFICE
CERTIFICATE OF CORRECTION

PATENT NO. : 8,008,463 B2  
APPLICATION NO. : 10/511362  
DATED : August 30, 2011  
INVENTOR(S) : Blackshear et al.

Page 1 of 1

It is certified that error appears in the above-identified patent and that said Letters Patent is hereby corrected as shown below:

In the Specification

In column 13, line 8, the words "transcript cDNAs" should be --transcript. cDNAs--

In column 20, line 48, the words and punctuation "from, a naturally" should be --from a naturally--

In column 28, line 25, the words and punctuation "rise, to" should read --rise to--

In column 33, line 12, the punctuation and numbers "/1986])." should be --[1986]).--

In column 34, line 46, the words and punctuation "utilized In" should be --utilized. In--

In column 47, line 52, the words and number "herpes virus 0.1" should be --herpes virus 1--

In column 47, line 60, the word "Samulsid" should be --Samulski--

In column 47, line 62, the words and punctuation "LebkowskietaL" should be --Lebkowski et al.)--

In column 52, line 57, the letter and number "(p 1)" should be --(p1)--

In column 60, line 52, the letters and numbers "RFX4 V3" should be --"RFX4_v3--

In column 66, line 20, the letters and numbers "RFX4 V3" should be --"RFX4_v3--

In column 66, line 28, the letters and numbers "RFX4 V3" should be --"RFX4_v3--

In column 67, line 57, the letters and number "*Pa6*" should be --*Pax6*--

Signed and Sealed this  
Seventeenth Day of June, 2014

Michelle K. Lee  
*Deputy Director of the United States Patent and Trademark Office*

SEQUENCE LISTING

<160> NUMBER OF SEQ ID NOS: 40

<210> SEQ ID NO 1
<211> LENGTH: 2188
<212> TYPE: DNA
<213> ORGANISM: Homo sapiens
<220> FEATURE:
<221> NAME/KEY: CDS
<222> LOCATION: (106)..(1797)

<400> SEQUENCE: 1

```
tggagaggcc acagctgctg gcttcctggg cttctccaaa ctcctgtgtg tcgccactgc        60
caccggcagg gagccaggag agagacagaa aggggctgag acaga atg atc aaa agg      117
                                                   Met Ile Lys Arg
                                                     1 aga gcc cac cct ggt gcg gga ggc gac agg acc agg cct cga cgg cgc        165
Arg Ala His Pro Gly Ala Gly Gly Asp Arg Thr Arg Pro Arg Arg Arg
 5                  10                  15                  20 cgt tcc act gag agc tgg att gaa aga tgt ctc aac gaa agt gaa aac        213
Arg Ser Thr Glu Ser Trp Ile Glu Arg Cys Leu Asn Glu Ser Glu Asn
                 25                  30                  35 aaa cgt tat tcc agc cac aca tct ctg ggg aat gtt tct aat gat gaa        261
Lys Arg Tyr Ser Ser His Thr Ser Leu Gly Asn Val Ser Asn Asp Glu
         40                  45                  50 aat gag gaa aaa gaa aat aat aga gca tcc aag ccc cac tcc act cct        309
Asn Glu Glu Lys Glu Asn Asn Arg Ala Ser Lys Pro His Ser Thr Pro
     55                  60                  65 gct act ctg caa tgg ctg gag gag aac tat gag att gca gag ggg gtc        357
Ala Thr Leu Gln Trp Leu Glu Glu Asn Tyr Glu Ile Ala Glu Gly Val
 70                  75                  80 tgc atc cct cgc agt gcc ctc tat atg cat tac ctg gat ttc tgc gag        405
Cys Ile Pro Arg Ser Ala Leu Tyr Met His Tyr Leu Asp Phe Cys Glu
85                  90                  95                 100 aag aat gat acc caa cct gtc aat gct gcc agc ttt gga aag atc ata        453
Lys Asn Asp Thr Gln Pro Val Asn Ala Ala Ser Phe Gly Lys Ile Ile
                105                 110                 115 agg cag cag ttt cct cag tta acc acc aga aga ctc ggg acc cga gga        501
Arg Gln Gln Phe Pro Gln Leu Thr Thr Arg Arg Leu Gly Thr Arg Gly
            120                 125                 130 cag tca aag tac cat tac tat ggc att gca gtg aaa gaa agc tcc caa        549
Gln Ser Lys Tyr His Tyr Tyr Gly Ile Ala Val Lys Glu Ser Ser Gln
        135                 140                 145 tat tat gat gtg atg tat tcc aag aaa gga gct gcc tgg gtg agt gag        597
Tyr Tyr Asp Val Met Tyr Ser Lys Lys Gly Ala Ala Trp Val Ser Glu
    150                 155                 160 acg ggc aag aaa gaa gtg agc aaa cag aca gtg gca tat tca ccc cgg        645
Thr Gly Lys Lys Glu Val Ser Lys Gln Thr Val Ala Tyr Ser Pro Arg
165                 170                 175                 180 tcc aaa ctc gga aca ctg ctg cca gaa ttt ccc aat gtc aaa gat cta        693
Ser Lys Leu Gly Thr Leu Leu Pro Glu Phe Pro Asn Val Lys Asp Leu
                185                 190                 195 aat ctg cca gcc agc ctg cct gag gag aag gtt tct acc ttt att atg        741
Asn Leu Pro Ala Ser Leu Pro Glu Glu Lys Val Ser Thr Phe Ile Met
            200                 205                 210 atg tac aga aca cac tgt cag aga ata ctg gac act gta ata aga gcc        789
Met Tyr Arg Thr His Cys Gln Arg Ile Leu Asp Thr Val Ile Arg Ala
        215                 220                 225 aac ttt gat gag gtt caa agt ttc ctt ctg cac ttt tgg caa gga atg        837
Asn Phe Asp Glu Val Gln Ser Phe Leu Leu His Phe Trp Gln Gly Met
    230                 235                 240
```

|  |  |
|---|---|
| ccg ccc cac atg ctg cct gtg ctg ggc tcc tcc acg gtg gtg aac att<br>Pro Pro His Met Leu Pro Val Leu Gly Ser Ser Thr Val Val Asn Ile<br>245                          250                        255                     260 | 885 |
| gtc ggc gtg tgt gac tcc atc ctc tac aaa gct atc tcc ggg gtg ctg<br>Val Gly Val Cys Asp Ser Ile Leu Tyr Lys Ala Ile Ser Gly Val Leu<br>               265                       270                       275 | 933 |
| atg ccc act gtg ctg cag gca tta cct gac agc tta act cag gtg att<br>Met Pro Thr Val Leu Gln Ala Leu Pro Asp Ser Leu Thr Gln Val Ile<br>        280                       285                       290 | 981 |
| cga aag ttt gcc aag caa ctg gat gag tgg cta aaa gtg gct ctc cac<br>Arg Lys Phe Ala Lys Gln Leu Asp Glu Trp Leu Lys Val Ala Leu His<br>            295                       300                     305 | 1029 |
| gac ctc cca gaa aac ttg cga aac atc aag ttc gaa ttg tcg aga agg<br>Asp Leu Pro Glu Asn Leu Arg Asn Ile Lys Phe Glu Leu Ser Arg Arg<br>310                          315                        320 | 1077 |
| ttc tcc caa att ctg aga cgg caa aca tca cta aat cat ctc tgc cag<br>Phe Ser Gln Ile Leu Arg Arg Gln Thr Ser Leu Asn His Leu Cys Gln<br>325                          330                        335                     340 | 1125 |
| gca tct cga aca gtg atc cac agt gca gac atc acg ttc caa atg ctg<br>Ala Ser Arg Thr Val Ile His Ser Ala Asp Ile Thr Phe Gln Met Leu<br>               345                       350                       355 | 1173 |
| gaa gac tgg agg aac gtg gac ctg aac agc atc acc aag caa acc ctt<br>Glu Asp Trp Arg Asn Val Asp Leu Asn Ser Ile Thr Lys Gln Thr Leu<br>        360                       365                       370 | 1221 |
| tac acc atg gaa gac tct cgc gat gag cac cgg aaa ctc atc acc caa<br>Tyr Thr Met Glu Asp Ser Arg Asp Glu His Arg Lys Leu Ile Thr Gln<br>            375                       380                     385 | 1269 |
| tta tat cag gag ttt gac cat ctc ttg gag gag cag tct ccc atc gag<br>Leu Tyr Gln Glu Phe Asp His Leu Leu Glu Glu Gln Ser Pro Ile Glu<br>390                          395                        400 | 1317 |
| tcc tac att gag tgg ctg gat acc atg gtt gac cgc tgt gtt gtg aag<br>Ser Tyr Ile Glu Trp Leu Asp Thr Met Val Asp Arg Cys Val Val Lys<br>405                          410                       415                     420 | 1365 |
| gtg gct gcc aag aga caa ggg tcc ttg aag aaa gtg gcc cag cag ttc<br>Val Ala Ala Lys Arg Gln Gly Ser Leu Lys Lys Val Ala Gln Gln Phe<br>               425                       430                       435 | 1413 |
| ctc ttg atg tgg tcc tgt ttc ggc aca agg gtg atc cgg gac atg acc<br>Leu Leu Met Trp Ser Cys Phe Gly Thr Arg Val Ile Arg Asp Met Thr<br>        440                       445                       450 | 1461 |
| ttg cac agc gcc ccc agc ttc ggg tct ttt cac cta att cac tta atg<br>Leu His Ser Ala Pro Ser Phe Gly Ser Phe His Leu Ile His Leu Met<br>            455                       460                     465 | 1509 |
| ttt gat gac tac gtg ctc tac ctg tta gaa tct ctg cac tgt cag gag<br>Phe Asp Asp Tyr Val Leu Tyr Leu Leu Glu Ser Leu His Cys Gln Glu<br>470                          475                        480 | 1557 |
| cgg gcc aat gag ctc atg cga gcc atg aag gga gaa gga agc act gca<br>Arg Ala Asn Glu Leu Met Arg Ala Met Lys Gly Glu Gly Ser Thr Ala<br>485                          490                        495                     500 | 1605 |
| gaa gtc cga gaa gag atc atc ttg aca gag gct gcc gca cca acc cct<br>Glu Val Arg Glu Glu Ile Ile Leu Thr Glu Ala Ala Ala Pro Thr Pro<br>               505                       510                       515 | 1653 |
| tca cca gtg cca tcg ttt tct cca gca aaa tct gcc aca tct gtg gaa<br>Ser Pro Val Pro Ser Phe Ser Pro Ala Lys Ser Ala Thr Ser Val Glu<br>        520                       525                       530 | 1701 |
| gtg cca cct ccc tct tcc cct gtt agc aat cct tcc cct gag tac act<br>Val Pro Pro Pro Ser Ser Pro Val Ser Asn Pro Ser Pro Glu Tyr Thr<br>            535                       540                     545 | 1749 |
| ggc ctc agc act aca ggt aat gga aag tcc ttc aaa aac ttt ggg tag<br>Gly Leu Ser Thr Thr Gly Asn Gly Lys Ser Phe Lys Asn Phe Gly<br>550                          555                        560 | 1797 |

```
ttaatgtttg aagaaagggc tttctgccag cctgggcaac atagtgagac ttcatttcca    1857
cacacacaaa aagccagaca tcttggctca cacctgtagt cccagctact tgggaggctg    1917
aggtgggaga attgcttgag cccaggagct acgatcgcac cactgcattc tagccttagt    1977
gatacagtga gaccttgtct caaaaaaaga aaaacagggc tttctggaaa acattcttc     2037 tcccacaatc tccaaaagat aatgccaaaa cctgggtatc ttcctggatt tgtgaatgac    2097
gtacaggtat tcatttattc attggtacac attctgtatg ctgctgtttt caagttggca    2157
aattaagcat atgataaaat cccaaaacta a                                   2188
```

<210> SEQ ID NO 2
<211> LENGTH: 563
<212> TYPE: PRT
<213> ORGANISM: Homo sapiens

<400> SEQUENCE: 2

```
Met Ile Lys Arg Arg Ala His Pro Gly Ala Gly Gly Asp Arg Thr Arg
  1               5                  10                  15

Pro Arg Arg Arg Ser Thr Glu Ser Trp Ile Glu Arg Cys Leu Asn
             20                  25                  30

Glu Ser Glu Asn Lys Arg Tyr Ser Ser His Thr Ser Leu Gly Asn Val
         35                  40                  45

Ser Asn Asp Glu Asn Glu Lys Glu Asn Asn Arg Ala Ser Lys Pro
     50                  55                  60

His Ser Thr Pro Ala Thr Leu Gln Trp Leu Glu Glu Asn Tyr Glu Ile
 65                  70                  75                  80

Ala Glu Gly Val Cys Ile Pro Arg Ser Ala Leu Tyr Met His Tyr Leu
                 85                  90                  95

Asp Phe Cys Glu Lys Asn Asp Thr Gln Pro Val Asn Ala Ala Ser Phe
            100                 105                 110

Gly Lys Ile Ile Arg Gln Gln Phe Pro Gln Leu Thr Thr Arg Arg Leu
        115                 120                 125

Gly Thr Arg Gly Gln Ser Lys Tyr His Tyr Tyr Gly Ile Ala Val Lys
    130                 135                 140

Glu Ser Ser Gln Tyr Tyr Asp Val Met Tyr Ser Lys Lys Gly Ala Ala
145                 150                 155                 160

Trp Val Ser Glu Thr Gly Lys Lys Glu Val Ser Lys Gln Thr Val Ala
                165                 170                 175

Tyr Ser Pro Arg Ser Lys Leu Gly Thr Leu Leu Pro Glu Phe Pro Asn
            180                 185                 190

Val Lys Asp Leu Asn Leu Pro Ala Ser Leu Pro Glu Glu Lys Val Ser
        195                 200                 205

Thr Phe Ile Met Met Tyr Arg Thr His Cys Gln Arg Ile Leu Asp Thr
    210                 215                 220

Val Ile Arg Ala Asn Phe Asp Glu Val Gln Ser Phe Leu Leu His Phe
225                 230                 235                 240

Trp Gln Gly Met Pro Pro His Met Leu Pro Val Leu Gly Ser Ser Thr
                245                 250                 255

Val Val Asn Ile Val Gly Val Cys Asp Ser Ile Leu Tyr Lys Ala Ile
            260                 265                 270

Ser Gly Val Leu Met Pro Thr Val Leu Gln Ala Leu Pro Asp Ser Leu
        275                 280                 285

Thr Gln Val Ile Arg Lys Phe Ala Lys Gln Leu Asp Glu Trp Leu Lys
    290                 295                 300
```

```
Val Ala Leu His Asp Leu Pro Glu Asn Leu Arg Asn Ile Lys Phe Glu
305                 310                 315                 320

Leu Ser Arg Arg Phe Ser Gln Ile Leu Arg Gln Thr Ser Leu Asn
            325                 330                 335

His Leu Cys Gln Ala Ser Arg Thr Val Ile His Ser Ala Asp Ile Thr
                340                 345                 350

Phe Gln Met Leu Glu Asp Trp Arg Asn Val Asp Leu Asn Ser Ile Thr
            355                 360                 365

Lys Gln Thr Leu Tyr Thr Met Glu Asp Ser Arg Asp Glu His Arg Lys
370                 375                 380

Leu Ile Thr Gln Leu Tyr Gln Glu Phe Asp His Leu Leu Glu Glu Gln
385                 390                 395                 400

Ser Pro Ile Glu Ser Tyr Ile Glu Trp Leu Asp Thr Met Val Asp Arg
                405                 410                 415

Cys Val Val Lys Val Ala Ala Lys Arg Gln Gly Ser Leu Lys Lys Val
            420                 425                 430

Ala Gln Gln Phe Leu Leu Met Trp Ser Cys Phe Gly Thr Arg Val Ile
        435                 440                 445

Arg Asp Met Thr Leu His Ser Ala Pro Ser Phe Gly Ser Phe His Leu
    450                 455                 460

Ile His Leu Met Phe Asp Asp Tyr Val Leu Tyr Leu Leu Glu Ser Leu
465                 470                 475                 480

His Cys Gln Glu Arg Ala Asn Glu Leu Met Arg Ala Met Lys Gly Glu
                485                 490                 495

Gly Ser Thr Ala Glu Val Arg Glu Glu Ile Ile Leu Thr Glu Ala Ala
            500                 505                 510

Ala Pro Thr Pro Ser Pro Val Pro Ser Phe Ser Pro Ala Lys Ser Ala
        515                 520                 525

Thr Ser Val Glu Val Pro Pro Pro Ser Ser Pro Val Ser Asn Pro Ser
    530                 535                 540

Pro Glu Tyr Thr Gly Leu Ser Thr Thr Gly Asn Gly Lys Ser Phe Lys
545                 550                 555                 560

Asn Phe Gly

<210> SEQ ID NO 3
<211> LENGTH: 3382
<212> TYPE: DNA
<213> ORGANISM: Homo sapiens
<220> FEATURE:
<221> NAME/KEY: CDS
<222> LOCATION: (110)..(2035)

<400> SEQUENCE: 3
aggtgggaag gcagttatga cagttgagaa gtagtagaag acacggaagg cacagaaggc      60
agacttcgct cagcacaaag aagaattttc tgataaccat actggcaaa atg aac tgg     118
                                                    Met Asn Trp
                                                      1 gct gcc ttc gga ggg tct gaa ttc ttc atc cca gaa ggc att cag ata       166
Ala Ala Phe Gly Gly Ser Glu Phe Phe Ile Pro Glu Gly Ile Gln Ile
  5                  10                  15 gat tcg aga tgc cca cta agc aga aat atc acg gaa tgg tac cat tac       214
Asp Ser Arg Cys Pro Leu Ser Arg Asn Ile Thr Glu Trp Tyr His Tyr
 20                  25                  30                  35 tat ggc att gca gtg aaa gaa agc tcc caa tat tat gat gtg atg tat       262
Tyr Gly Ile Ala Val Lys Glu Ser Ser Gln Tyr Tyr Asp Val Met Tyr
                 40                  45                  50 tcc aag aaa gga gct gcc tgg gtg agt gag acg ggc aag aaa gaa gtg       310
```

|                           |      |
|---------------------------|------|
| Ser Lys Lys Gly Ala Ala Trp Val Ser Glu Thr Gly Lys Lys Glu Val<br>55              60              65 | |
| agc aaa cag aca gtg gca tat tca ccc cgg tcc aaa ctc gga aca ctg<br>Ser Lys Gln Thr Val Ala Tyr Ser Pro Arg Ser Lys Leu Gly Thr Leu<br>70              75              80 | 358 |
| ctg cca gaa ttt ccc aat gtc aaa gat cta aat ctg cca gcc agc ctg<br>Leu Pro Glu Phe Pro Asn Val Lys Asp Leu Asn Leu Pro Ala Ser Leu<br>85              90              95 | 406 |
| cct gag gag aag gtt tct acc ttt att atg atg tac aga aca cac tgt<br>Pro Glu Glu Lys Val Ser Thr Phe Ile Met Met Tyr Arg Thr His Cys<br>100             105             110             115 | 454 |
| cag aga ata ctg gac act gta ata aga gcc aac ttt gat gag gtt caa<br>Gln Arg Ile Leu Asp Thr Val Ile Arg Ala Asn Phe Asp Glu Val Gln<br>120             125             130 | 502 |
| agt ttc ctt ctg cac ttt tgg caa gga atg ccg ccc cac atg ctg cct<br>Ser Phe Leu Leu His Phe Trp Gln Gly Met Pro Pro His Met Leu Pro<br>135             140             145 | 550 |
| gtg ctg ggc tcc tcc acg gtg gtg aac att gtc ggc gtg tgt gac tcc<br>Val Leu Gly Ser Ser Thr Val Val Asn Ile Val Gly Val Cys Asp Ser<br>150             155             160 | 598 |
| atc ctc tac aaa gct atc tcc ggg gtg ctg atg ccc act gtg ctg cag<br>Ile Leu Tyr Lys Ala Ile Ser Gly Val Leu Met Pro Thr Val Leu Gln<br>165             170             175 | 646 |
| gca tta cct gac agc tta act cag gtg att cga aag ttt gcc aag caa<br>Ala Leu Pro Asp Ser Leu Thr Gln Val Ile Arg Lys Phe Ala Lys Gln<br>180             185             190             195 | 694 |
| ctg gat gag tgg cta aaa gtg gct ctc cac gac ctc cca gaa aac ttg<br>Leu Asp Glu Trp Leu Lys Val Ala Leu His Asp Leu Pro Glu Asn Leu<br>200             205             210 | 742 |
| cga aac atc aag ttc gaa ttg tcg aga agg ttc tcc caa att ctg aga<br>Arg Asn Ile Lys Phe Glu Leu Ser Arg Arg Phe Ser Gln Ile Leu Arg<br>215             220             225 | 790 |
| cgg caa aca tca cta aat cat ctc tgc cag gca tct cga aca gtg atc<br>Arg Gln Thr Ser Leu Asn His Leu Cys Gln Ala Ser Arg Thr Val Ile<br>230             235             240 | 838 |
| cac agt gca gac atc acg ttc caa atg ctg gaa gac tgg agg aac gtg<br>His Ser Ala Asp Ile Thr Phe Gln Met Leu Glu Asp Trp Arg Asn Val<br>245             250             255 | 886 |
| gac ctg aac agc atc acc aag caa acc ctt tac acc atg gaa gac tct<br>Asp Leu Asn Ser Ile Thr Lys Gln Thr Leu Tyr Thr Met Glu Asp Ser<br>260             265             270             275 | 934 |
| cgc gat gag cac cgg aaa ctc atc acc caa tta tat cag gag ttt gac<br>Arg Asp Glu His Arg Lys Leu Ile Thr Gln Leu Tyr Gln Glu Phe Asp<br>280             285             290 | 982 |
| cat ctc ttg gag gag cag tct ccc atc gag tcc tac att gag tgg ctg<br>His Leu Leu Glu Glu Gln Ser Pro Ile Glu Ser Tyr Ile Glu Trp Leu<br>295             300             305 | 1030 |
| gat acc atg gtt gac cgc tgt gtt gtg aag gtg gct gcc aag aga cga<br>Asp Thr Met Val Asp Arg Cys Val Val Lys Val Ala Ala Lys Arg Arg<br>310             315             320 | 1078 |
| ggg tcc ttg aag aaa gtg gcc cag cag ttc ctc ttg atg tgg tcc tgt<br>Gly Ser Leu Lys Lys Val Ala Gln Gln Phe Leu Leu Met Trp Ser Cys<br>325             330             335 | 1126 |
| ttc ggc aca agg gtg atc cgg gac atg acc ttg cac agc gcc ccc agc<br>Phe Gly Thr Arg Val Ile Arg Asp Met Thr Leu His Ser Ala Pro Ser<br>340             345             350             355 | 1174 |
| ttc ggg tct ttt cac cta att cac tta atg ttt gat gac tac gtg ctc<br>Phe Gly Ser Phe His Leu Ile His Leu Met Phe Asp Asp Tyr Val Leu<br>360             365             370 | 1222 |
| tac ctg tta gaa tct ctg cac tgt cag gag cgg gcc aat gag ctc atg | 1270 |

-continued

```
Tyr Leu Leu Glu Ser Leu His Cys Gln Glu Arg Ala Asn Glu Leu Met
            375                 380                 385 cga gcc atg aag gga gaa gga agc act gca gaa gtc cga gaa gag atc      1318
Arg Ala Met Lys Gly Glu Gly Ser Thr Ala Glu Val Arg Glu Glu Ile
            390                 395                 400 atc ttg aca gag gct gcc gca cca acc cct tca cca gtg cca tcg ttt      1366
Ile Leu Thr Glu Ala Ala Ala Pro Thr Pro Ser Pro Val Pro Ser Phe
            405                 410                 415 tct cca gca aaa tct gcc aca tct gtg gaa gtg cca cct ccc tct tcc      1414
Ser Pro Ala Lys Ser Ala Thr Ser Val Glu Val Pro Pro Pro Ser Ser
420                 425                 430                 435 cct gtt agc aat cct tcc cct gag tac act ggc ctc agc act aca gga      1462
Pro Val Ser Asn Pro Ser Pro Glu Tyr Thr Gly Leu Ser Thr Thr Gly
                440                 445                 450 gca atg cag gct tac acg tgg tct cta aca tac aca gtg acg acg gct      1510
Ala Met Gln Ala Tyr Thr Trp Ser Leu Thr Tyr Thr Val Thr Thr Ala
                455                 460                 465 gct ggg tcc cca gct gag aac tcc caa cag ctg ccc tgt atg agg aac      1558
Ala Gly Ser Pro Ala Glu Asn Ser Gln Gln Leu Pro Cys Met Arg Asn
            470                 475                 480 act cac gtg cct tct tcc tcc gtc aca cac agg ata cca gtt tat ccc      1606
Thr His Val Pro Ser Ser Ser Val Thr His Arg Ile Pro Val Tyr Pro
        485                 490                 495 cac aga gag gaa cat gga tac acg gga agc tat aac tat ggg agc tat      1654
His Arg Glu Glu His Gly Tyr Thr Gly Ser Tyr Asn Tyr Gly Ser Tyr
500                 505                 510                 515 ggc aac cag cat cct cac ccc atg cag agc cag tat ccg gcc ctc cct      1702
Gly Asn Gln His Pro His Pro Met Gln Ser Gln Tyr Pro Ala Leu Pro
                520                 525                 530 cat gac aca gct atc tct ggg cca ctc cac tat gcc cct tac cac agg      1750
His Asp Thr Ala Ile Ser Gly Pro Leu His Tyr Ala Pro Tyr His Arg
                535                 540                 545 agc tct gca cag tac cct ttt aat agc ccc act tcc cgg atg gaa cct      1798
Ser Ser Ala Gln Tyr Pro Phe Asn Ser Pro Thr Ser Arg Met Glu Pro
            550                 555                 560 tgt ttg atg agc agt act ccc aga ctg cat cct acc cca gtc act ccc      1846
Cys Leu Met Ser Ser Thr Pro Arg Leu His Pro Thr Pro Val Thr Pro
565                 570                 575 cgc tgg cca gag gtg ccc tca gcc aac acg tgc tac aca aac ccg tct      1894
Arg Trp Pro Glu Val Pro Ser Ala Asn Thr Cys Tyr Thr Asn Pro Ser
580                 585                 590                 595 gtg cat tct gcg agg tac gga aac tct agt gac atg tat aca cct ctg      1942
Val His Ser Ala Arg Tyr Gly Asn Ser Ser Asp Met Tyr Thr Pro Leu
                600                 605                 610 aca acg cgc agg aat tct gaa tat gag cac atg caa cac ttt cct ggc      1990
Thr Thr Arg Arg Asn Ser Glu Tyr Glu His Met Gln His Phe Pro Gly
            615                 620                 625 ttt gct tac atc aac gga gag gcc tct aca gga tgg gct aaa tga           2035
Phe Ala Tyr Ile Asn Gly Glu Ala Ser Thr Gly Trp Ala Lys
            630                 635                 640 ctgctatcat aggcatccat atttaatatt aataataata attaataata ataataaacc    2095
caacacccat cccccagaag actttatctc tatacattgt aactcatggg ctattcctaa    2155
gtgcccattt tcctaatgaa catgaggatg ggatcaatgt gggatgaata aactttagtt    2215
cagaaacagg acttactaaa agtcagtggg actgggtttc tgtagccaag ccagacttga    2275
ctgtttctgt agagcactat ctcgggcagg ccattctgtg ccttttccct ctgttccatg    2335
actttgcttt tgtgttggcaa ccacttctag taagctactt attttcctgt tgacaaaatc   2395
tctttagtct tgaaggatgg atactggaga cagaatctgg tttgtgttct tggatgggca    2455
```

```
cataatttac caagagcatt caccttgcca tctgtcttgt cattgtactg tacaaggaac    2515
agccctcaga cgtgttctgc acatcccttc ttcctggtgg taccatccct atttcctgga    2575
gcaccagggc taaatgggga gctatctgga aactctagat tttctgtcat acccacatct    2635
gtcacagtac ctgcattgtc ttggaatgta agcactgtct tgagggaagg aagaggtctg    2695
ttctgtattg ccttaagttg attgaggttt gtaggagact ggttcttcta catacaagga    2755
tttgtcttaa gtttgcacaa tggctagtgt cagcaaaagg caggagaggg tttttgtttt    2815 tttttttaagt tctatgagaa tgtggattta tggcattgag tatcacactc agctctgctg    2875
tgttaacttt gtgaaactgg atggaacaaa ctttaactta ccaagcacca agtgtgaaag    2935
tgactttcac ggttccttca taaaactata ataatatccg acactttgat agaaaaaaat    2995
tcaaagctgt gcctttgagc ctatactata ctgtgtatgt gtggaaataa aaatgtattg    3055
tacttttgga gattttttg taggcatttt tctgtcagat ttgtagtaat ttgtgaggtt    3115
tgttagagat taatataggt tttctttctg tattataaaa tgcaccaagc aattatggtg    3175
gacctattac cctatgggta agaaataaat ggaaatatga catcggatgt ttcagcaact    3235
gttctgtaaa taaaatcttt gatcacacca ctcagtgtga taattgtgtc tacagctaaa    3295
atggaaatag ttttatctgt acagttgtgc aagatatgaa tggtttcaca ctcaaataaa    3355
aaatattgaa ccccccaaaaa aaaaaaa                                      3382
```

<210> SEQ ID NO 4
<211> LENGTH: 641
<212> TYPE: PRT
<213> ORGANISM: Homo sapiens

<400> SEQUENCE: 4

```
Met Asn Trp Ala Ala Phe Gly Gly Ser Glu Phe Ile Pro Glu Gly
1               5                   10                  15

Ile Gln Ile Asp Ser Arg Cys Pro Leu Ser Arg Asn Ile Thr Glu Trp
            20                  25                  30

Tyr His Tyr Tyr Gly Ile Ala Val Lys Glu Ser Ser Gln Tyr Tyr Asp
        35                  40                  45

Val Met Tyr Ser Lys Lys Gly Ala Ala Trp Val Ser Glu Thr Gly Lys
    50                  55                  60

Lys Glu Val Ser Lys Gln Thr Val Ala Tyr Ser Pro Arg Ser Lys Leu
65                  70                  75                  80

Gly Thr Leu Leu Pro Glu Phe Pro Asn Val Lys Asp Leu Asn Leu Pro
                85                  90                  95

Ala Ser Leu Pro Glu Glu Lys Val Ser Thr Phe Ile Met Met Tyr Arg
            100                 105                 110

Thr His Cys Gln Arg Ile Leu Asp Thr Val Ile Arg Ala Asn Phe Asp
        115                 120                 125

Glu Val Gln Ser Phe Leu Leu His Phe Trp Gln Gly Met Pro Pro His
    130                 135                 140

Met Leu Pro Val Leu Gly Ser Ser Thr Val Asn Ile Val Gly Val
145                 150                 155                 160

Cys Asp Ser Ile Leu Tyr Lys Ala Ile Ser Gly Val Leu Met Pro Thr
                165                 170                 175

Val Leu Gln Ala Leu Pro Asp Ser Leu Thr Gln Val Ile Arg Lys Phe
            180                 185                 190

Ala Lys Gln Leu Asp Glu Trp Leu Lys Val Ala Leu His Asp Leu Pro
        195                 200                 205
```

-continued

Glu Asn Leu Arg Asn Ile Lys Phe Glu Leu Ser Arg Arg Phe Ser Gln
210                 215                 220

Ile Leu Arg Arg Gln Thr Ser Leu Asn His Leu Cys Gln Ala Ser Arg
225                 230                 235                 240

Thr Val Ile His Ser Ala Asp Ile Thr Phe Gln Met Leu Glu Asp Trp
            245                 250                 255

Arg Asn Val Asp Leu Asn Ser Ile Thr Lys Gln Thr Leu Tyr Thr Met
            260                 265                 270

Glu Asp Ser Arg Asp Glu His Arg Lys Leu Ile Thr Gln Leu Tyr Gln
        275                 280                 285

Glu Phe Asp His Leu Leu Glu Glu Gln Ser Pro Ile Glu Ser Tyr Ile
    290                 295                 300

Glu Trp Leu Asp Thr Met Val Asp Arg Cys Val Val Lys Val Ala Ala
305                 310                 315                 320

Lys Arg Arg Gly Ser Leu Lys Lys Val Ala Gln Gln Phe Leu Leu Met
                325                 330                 335

Trp Ser Cys Phe Gly Thr Arg Val Ile Arg Asp Met Thr Leu His Ser
            340                 345                 350

Ala Pro Ser Phe Gly Ser Phe His Leu Ile His Leu Met Phe Asp Asp
        355                 360                 365

Tyr Val Leu Tyr Leu Leu Glu Ser Leu His Cys Gln Glu Arg Ala Asn
    370                 375                 380

Glu Leu Met Arg Ala Met Lys Gly Glu Gly Ser Thr Ala Glu Val Arg
385                 390                 395                 400

Glu Glu Ile Ile Leu Thr Glu Ala Ala Pro Thr Pro Ser Pro Val
                405                 410                 415

Pro Ser Phe Ser Pro Ala Lys Ser Ala Thr Ser Val Glu Val Pro Pro
            420                 425                 430

Pro Ser Ser Pro Val Ser Asn Pro Ser Pro Glu Tyr Thr Gly Leu Ser
        435                 440                 445

Thr Thr Gly Ala Met Gln Ala Tyr Thr Trp Ser Leu Thr Tyr Thr Val
    450                 455                 460

Thr Thr Ala Ala Gly Ser Pro Ala Glu Asn Ser Gln Gln Leu Pro Cys
465                 470                 475                 480

Met Arg Asn Thr His Val Pro Ser Ser Val Thr His Arg Ile Pro
                485                 490                 495

Val Tyr Pro His Arg Glu Glu His Gly Tyr Thr Gly Ser Tyr Asn Tyr
            500                 505                 510

Gly Ser Tyr Gly Asn Gln His Pro His Pro Met Gln Ser Gln Tyr Pro
        515                 520                 525

Ala Leu Pro His Asp Thr Ala Ile Ser Gly Pro Leu His Tyr Ala Pro
    530                 535                 540

Tyr His Arg Ser Ser Ala Gln Tyr Pro Phe Asn Ser Pro Thr Ser Arg
545                 550                 555                 560

Met Glu Pro Cys Leu Met Ser Ser Thr Pro Arg Leu His Pro Thr Pro
                565                 570                 575

Val Thr Pro Arg Trp Pro Glu Val Pro Ser Ala Asn Thr Cys Tyr Thr
            580                 585                 590

Asn Pro Ser Val His Ser Ala Arg Tyr Gly Asn Ser Ser Asp Met Tyr
        595                 600                 605

Thr Pro Leu Thr Thr Arg Arg Asn Ser Glu Tyr Glu His Met Gln His
    610                 615                 620

Phe Pro Gly Phe Ala Tyr Ile Asn Gly Glu Ala Ser Thr Gly Trp Ala
625                 630                 635                 640

Lys

<210> SEQ ID NO 5
<211> LENGTH: 2842
<212> TYPE: DNA
<213> ORGANISM: Mus musculus
<220> FEATURE:
<221> NAME/KEY: CDS
<222> LOCATION: (307)..(2520)

<400> SEQUENCE: 5

```
ttttgacggg tttggctttg cccgactgga ttactgagtg tcccctcgct cgttcgctcg      60
ccctctcgct ctctccttca gctctagctt ccttccttcc ctcgcttctt cgcctctttt     120
ctttccacta gttctttctt ttcccctttt atccttttgc cctctcaccc accgtctccc     180
cctctctctc tcgctatccc ttccttcctt atttcttccc tccttcctc cctgggcatc      240 tctagcacag gggatcccca aatatcagga cttttggggg gcgtctgtgc tgtccatggg     300
```

| | | | | | | | | | | | | | | | |
|---|---|---|---|---|---|---|---|---|---|---|---|---|---|---|---|
| aagagc | atg | cat | tgt | ggg | tta | ctg | gag | gaa | ccc | gac | atg | gat | tcc | aca | 348 |
| | Met | His | Cys | Gly | Leu | Leu | Glu | Glu | Pro | Asp | Met | Asp | Ser | Thr | |
| | 1 | | | 5 | | | | | 10 | | | | | | |

```
gag agc tgg att gaa aga tgt ctc aat gaa agc gag aat aaa cgc tat       396
Glu Ser Trp Ile Glu Arg Cys Leu Asn Glu Ser Glu Asn Lys Arg Tyr
15              20                  25                  30 tcc agt cac aca tct ctg ggg aat gtg tct aat gat gaa aat gag gaa       444
Ser Ser His Thr Ser Leu Gly Asn Val Ser Asn Asp Glu Asn Glu Glu
            35                  40                  45 aaa gaa aat aac aga gca tcc aag ccc cac tcc acg ccg gcc acc ctg       492
Lys Glu Asn Asn Arg Ala Ser Lys Pro His Ser Thr Pro Ala Thr Leu
    50                  55                  60 caa tgg ctg gag gaa aac tat gag att gct gag ggc gtc tgc atc ccc       540
Gln Trp Leu Glu Glu Asn Tyr Glu Ile Ala Glu Gly Val Cys Ile Pro
65                  70                  75 cgc agc gcc ctc tac atg cac tac ctg gat ttc tgt gag aag aac gac       588
Arg Ser Ala Leu Tyr Met His Tyr Leu Asp Phe Cys Glu Lys Asn Asp
    80                  85                  90 act cag cct gtc aat gct gcc agc ttt ggg aag atc ata agg cag cag       636
Thr Gln Pro Val Asn Ala Ala Ser Phe Gly Lys Ile Ile Arg Gln Gln
95                  100                 105                 110 ttt cct cag cta acc acc aga aga ctc ggg acc ggg acc cga gga cag       684
Phe Pro Gln Leu Thr Thr Arg Arg Leu Gly Thr Gly Thr Arg Gly Gln
                115                 120                 125 tca aag tac cat tac tat ggc ata gcg gtg aag gag agc tcc cag tat       732
Ser Lys Tyr His Tyr Tyr Gly Ile Ala Val Lys Glu Ser Ser Gln Tyr
            130                 135                 140 tat gat gtg atg tac tca aag aaa gga gct gcc tgg gtg agc gag acg       780
Tyr Asp Val Met Tyr Ser Lys Lys Gly Ala Ala Trp Val Ser Glu Thr
        145                 150                 155 ggc aag aga gaa gtc acc aag cag acg gtg gca tat tct ccc cgg tcc       828
Gly Lys Arg Glu Val Thr Lys Gln Thr Val Ala Tyr Ser Pro Arg Ser
    160                 165                 170 aag ctt ggg aca ttg ctg cca gac ttt cca aac gtc aaa gac cta aat       876
Lys Leu Gly Thr Leu Leu Pro Asp Phe Pro Asn Val Lys Asp Leu Asn
175                 180                 185                 190 ctg cca gcc agt ctt cct gag gag aag gtg tct acc ttt att atg atg       924
Leu Pro Ala Ser Leu Pro Glu Glu Lys Val Ser Thr Phe Ile Met Met
                195                 200                 205 tac aga aca cac tgt cag aga ata ctg gac act gta ata aga gcc aac       972
Tyr Arg Thr His Cys Gln Arg Ile Leu Asp Thr Val Ile Arg Ala Asn
            210                 215                 220
```

```
ttt gat gag gtt caa agt ttc ctt ctg cac ttt tgg caa ggg atg ccg    1020
Phe Asp Glu Val Gln Ser Phe Leu Leu His Phe Trp Gln Gly Met Pro
        225                 230                 235 ccc cac atg ctg ccc gtg cta ggc tcc tcg acg gtg gtg aac atc gtg    1068
Pro His Met Leu Pro Val Leu Gly Ser Ser Thr Val Val Asn Ile Val
    240                 245                 250 ggt gtg tgt gac tcc atc ctc tac aaa gcc atc tcc ggt gtg ttg atg    1116
Gly Val Cys Asp Ser Ile Leu Tyr Lys Ala Ile Ser Gly Val Leu Met
255                 260                 265                 270 ccc acg gtg ctg cag gcg ttg ccg gac agc tta act cag gtg atc cga    1164
Pro Thr Val Leu Gln Ala Leu Pro Asp Ser Leu Thr Gln Val Ile Arg
                275                 280                 285 aag ttt gcc aag cag ctg gac gag tgg ctg aaa gtg gct ctc cac gat    1212
Lys Phe Ala Lys Gln Leu Asp Glu Trp Leu Lys Val Ala Leu His Asp
            290                 295                 300 ctc ccg gaa aac ctg aga aac atc aaa ttt gaa tta tca agg agg ttt    1260
Leu Pro Glu Asn Leu Arg Asn Ile Lys Phe Glu Leu Ser Arg Arg Phe
        305                 310                 315 tcc caa atc cta agg agg caa aca tcg ctg aac cat ctg tgc cag gca    1308
Ser Gln Ile Leu Arg Arg Gln Thr Ser Leu Asn His Leu Cys Gln Ala
    320                 325                 330 tct cga acg gtg atc cac agt gca gac atc acg ttc cag atg ctg gag    1356
Ser Arg Thr Val Ile His Ser Ala Asp Ile Thr Phe Gln Met Leu Glu
335                 340                 345                 350 gac tgg agg aat gtg gac ctg agt agc atc acc aag cag act ctg tat    1404
Asp Trp Arg Asn Val Asp Leu Ser Ser Ile Thr Lys Gln Thr Leu Tyr
                355                 360                 365 acc atg gag gac tct cgg gat gag cac cgc aga ctc atc atc cag ttg    1452
Thr Met Glu Asp Ser Arg Asp Glu His Arg Arg Leu Ile Ile Gln Leu
            370                 375                 380 tac cag gag ttt gac cac ctg ctg gag gaa cag tcc ccc atc gag tct    1500
Tyr Gln Glu Phe Asp His Leu Leu Glu Glu Gln Ser Pro Ile Glu Ser
        385                 390                 395 tac ata gaa tgg ctg gat acc atg gta gac cga tgc gtt gta aag gtg    1548
Tyr Ile Glu Trp Leu Asp Thr Met Val Asp Arg Cys Val Val Lys Val
    400                 405                 410 gct gcc aag aga caa ggg tct ctg aag aaa gta gcc caa cag ttc ctg    1596
Ala Ala Lys Arg Gln Gly Ser Leu Lys Lys Val Ala Gln Gln Phe Leu
415                 420                 425                 430 ctg atg tgg tct tgc ttt ggt acg agg gtg atc cgg gac atg acc ttg    1644
Leu Met Trp Ser Cys Phe Gly Thr Arg Val Ile Arg Asp Met Thr Leu
                435                 440                 445 cac agt gcc ccc agc ttc ggg tct ttt cac ctg att cac ctg atg ttc    1692
His Ser Ala Pro Ser Phe Gly Ser Phe His Leu Ile His Leu Met Phe
            450                 455                 460 gac gac tac gtc ctc tac ttg cta gaa tct ctg cat tgt cag gag cgg    1740
Asp Asp Tyr Val Leu Tyr Leu Leu Glu Ser Leu His Cys Gln Glu Arg
        465                 470                 475 gcc aac gag ctc atg cga gcc atg aaa gga gaa gga agc act gca gaa    1788
Ala Asn Glu Leu Met Arg Ala Met Lys Gly Glu Gly Ser Thr Ala Glu
    480                 485                 490 gcc cag gaa gag att atc ttg aca gag gct acc cca acc cct tca        1836
Ala Gln Glu Glu Ile Ile Leu Thr Glu Ala Thr Pro Thr Pro Ser
495                 500                 505                 510 cct ggt cca tca ttt tct cca gca aag tct gcc aca tct gtg gag gtg    1884
Pro Gly Pro Ser Phe Ser Pro Ala Lys Ser Ala Thr Ser Val Glu Val
                515                 520                 525 cca cct ccc tcc tcc cct gtc agc aac cca tcc ccc gaa tac act ggc    1932
Pro Pro Pro Ser Ser Pro Val Ser Asn Pro Ser Pro Glu Tyr Thr Gly
            530                 535                 540
```

| | | | | | | | | | | | | | | | |
|---|---|---|---|---|---|---|---|---|---|---|---|---|---|---|---|
| ctt | agc | aca | gca | gga | gcg | atg | cag | tca | tat | acg | tgg | tcg | cta | aca | tat | 1980 |
| Leu | Ser | Thr | Ala | Gly | Ala | Met | Gln | Ser | Tyr | Thr | Trp | Ser | Leu | Thr | Tyr | |
| | | 545 | | | | | 550 | | | | | 555 | | | | |

```
ctt agc aca gca gga gcg atg cag tca tat acg tgg tcg cta aca tat        1980
Leu Ser Thr Ala Gly Ala Met Gln Ser Tyr Thr Trp Ser Leu Thr Tyr
        545                 550                 555 aca gta aca acg gct gca ggg tca ccg gct gag aac tcc caa caa cta        2028
Thr Val Thr Thr Ala Ala Gly Ser Pro Ala Glu Asn Ser Gln Gln Leu
        560                 565                 570 ccc tgt atg agg agc acc cat atg cct tct tcc tcc gtc aca cac agg        2076
Pro Cys Met Arg Ser Thr His Met Pro Ser Ser Ser Val Thr His Arg
575                 580                 585                 590 ata cca gtc tac tcc cac aga gag gag cat ggg tac acg gga agc tat        2124
Ile Pro Val Tyr Ser His Arg Glu Glu His Gly Tyr Thr Gly Ser Tyr
                595                 600                 605 aac tac ggg agc tat ggc aac cag cat cct cac cca ctg cag aac cag        2172
Asn Tyr Gly Ser Tyr Gly Asn Gln His Pro His Pro Leu Gln Asn Gln
        610                 615                 620 tat cca gcc ttg cct cat gac aca gcc atc tct ggg cct ctc cac tat        2220
Tyr Pro Ala Leu Pro His Asp Thr Ala Ile Ser Gly Pro Leu His Tyr
        625                 630                 635 tcc cct tac cac agg agc tct gcc cag tac cct ttc aat agc ccc act        2268
Ser Pro Tyr His Arg Ser Ser Ala Gln Tyr Pro Phe Asn Ser Pro Thr
        640                 645                 650 tcc agg atg gaa cct tgt ttg atg agc agt act ccc agg ctg cat cct        2316
Ser Arg Met Glu Pro Cys Leu Met Ser Ser Thr Pro Arg Leu His Pro
655                 660                 665                 670 acc cca gtg act ccc cga tgg cca gag gtg ccg act gcc aac gca tgc        2364
Thr Pro Val Thr Pro Arg Trp Pro Glu Val Pro Thr Ala Asn Ala Cys
                675                 680                 685 tac aca agc cca tct gtg cat tcc acg agg tat gga aac tct agt gac        2412
Tyr Thr Ser Pro Ser Val His Ser Thr Arg Tyr Gly Asn Ser Ser Asp
        690                 695                 700 atg tac acc ccg ctg acc acg cgc agg aat tct gag tat gag cac atg        2460
Met Tyr Thr Pro Leu Thr Thr Arg Arg Asn Ser Glu Tyr Glu His Met
        705                 710                 715 caa cac ttt cct ggc ttt gct tac atc aac gga gag gcc tcc act gga        2508
Gln His Phe Pro Gly Phe Ala Tyr Ile Asn Gly Glu Ala Ser Thr Gly
        720                 725                 730 tgg gct aag tga ctgctttcat agaaatccat atttaatatt aataattaat           2560
Trp Ala Lys
735 aataataata aacccagtac ccaccctcca gaagacttta tttcaataca tcataacttg     2620 cgggctgacc taagcatcca ttctcctaat gaacaagagg atgttcaatg tggagtgaat     2680 agactttagt tcagaaacag gagtcactaa aagtcagtgg gattgggttt ctgtagccaa     2740 gccagacttg actgtttcta tagagcacta tcttgggcag gccaatctgt gcctttcccc     2800 tctgttccat gaccttgcat ggcaactact ccttgtatag gg                       2842

<210> SEQ ID NO 6
<211> LENGTH: 737
<212> TYPE: PRT
<213> ORGANISM: Mus musculus

<400> SEQUENCE: 6

Met His Cys Gly Leu Leu Glu Glu Pro Asp Met Asp Ser Thr Glu Ser
1               5                   10                  15

Trp Ile Glu Arg Cys Leu Asn Glu Ser Glu Asn Lys Arg Tyr Ser Ser
            20                  25                  30

His Thr Ser Leu Gly Asn Val Ser Asn Asp Glu Asn Glu Glu Lys Glu
        35                  40                  45

Asn Asn Arg Ala Ser Lys Pro His Ser Thr Pro Ala Thr Leu Gln Trp
```

-continued

```
            50                  55                  60
Leu Glu Glu Asn Tyr Glu Ile Ala Glu Gly Val Cys Ile Pro Arg Ser
 65                  70                  75                  80

Ala Leu Tyr Met His Tyr Leu Asp Phe Cys Glu Lys Asn Asp Thr Gln
                 85                  90                  95

Pro Val Asn Ala Ala Ser Phe Gly Lys Ile Ile Arg Gln Gln Phe Pro
                100                 105                 110

Gln Leu Thr Thr Arg Arg Leu Gly Thr Gly Thr Arg Gly Gln Ser Lys
                115                 120                 125

Tyr His Tyr Tyr Gly Ile Ala Val Lys Glu Ser Ser Gln Tyr Tyr Asp
                130                 135                 140

Val Met Tyr Ser Lys Lys Gly Ala Ala Trp Val Ser Glu Thr Gly Lys
145                 150                 155                 160

Arg Glu Val Thr Lys Gln Thr Val Ala Tyr Ser Pro Arg Ser Lys Leu
                165                 170                 175

Gly Thr Leu Leu Pro Asp Phe Pro Asn Val Lys Asp Leu Asn Leu Pro
                180                 185                 190

Ala Ser Leu Pro Glu Glu Lys Val Ser Thr Phe Ile Met Met Tyr Arg
                195                 200                 205

Thr His Cys Gln Arg Ile Leu Asp Thr Val Ile Arg Ala Asn Phe Asp
                210                 215                 220

Glu Val Gln Ser Phe Leu Leu His Phe Trp Gln Gly Met Pro Pro His
225                 230                 235                 240

Met Leu Pro Val Leu Gly Ser Ser Thr Val Asn Ile Val Gly Val
                245                 250                 255

Cys Asp Ser Ile Leu Tyr Lys Ala Ile Ser Gly Val Leu Met Pro Thr
                260                 265                 270

Val Leu Gln Ala Leu Pro Asp Ser Leu Thr Gln Val Ile Arg Lys Phe
                275                 280                 285

Ala Lys Gln Leu Asp Glu Trp Leu Lys Val Ala Leu His Asp Leu Pro
                290                 295                 300

Glu Asn Leu Arg Asn Ile Lys Phe Glu Leu Ser Arg Arg Phe Ser Gln
305                 310                 315                 320

Ile Leu Arg Arg Gln Thr Ser Leu Asn His Leu Cys Gln Ala Ser Arg
                325                 330                 335

Thr Val Ile His Ser Ala Asp Ile Thr Phe Gln Met Leu Glu Asp Trp
                340                 345                 350

Arg Asn Val Asp Leu Ser Ser Ile Thr Lys Gln Thr Leu Tyr Thr Met
                355                 360                 365

Glu Asp Ser Arg Asp Glu His Arg Arg Leu Ile Ile Gln Leu Tyr Gln
                370                 375                 380

Glu Phe Asp His Leu Leu Glu Glu Gln Ser Pro Ile Glu Ser Tyr Ile
385                 390                 395                 400

Glu Trp Leu Asp Thr Met Val Asp Arg Cys Val Val Lys Val Ala Ala
                405                 410                 415

Lys Arg Gln Gly Ser Leu Lys Lys Val Ala Gln Gln Phe Leu Leu Met
                420                 425                 430

Trp Ser Cys Phe Gly Thr Arg Val Ile Arg Asp Met Thr Leu His Ser
                435                 440                 445

Ala Pro Ser Phe Gly Ser Phe His Leu Ile His Leu Met Phe Asp Asp
                450                 455                 460

Tyr Val Leu Tyr Leu Leu Glu Ser Leu His Cys Gln Glu Arg Ala Asn
465                 470                 475                 480
```

```
Glu Leu Met Arg Ala Met Lys Gly Glu Gly Ser Thr Ala Glu Ala Gln
            485                 490                 495

Glu Glu Ile Ile Leu Thr Glu Ala Thr Pro Thr Pro Ser Pro Gly
        500                 505                 510

Pro Ser Phe Ser Pro Ala Lys Ser Ala Thr Ser Val Glu Val Pro Pro
        515                 520                 525

Pro Ser Ser Pro Val Ser Asn Pro Ser Pro Glu Tyr Thr Gly Leu Ser
        530                 535                 540

Thr Ala Gly Ala Met Gln Ser Tyr Thr Trp Ser Leu Thr Tyr Thr Val
545                 550                 555                 560

Thr Thr Ala Ala Gly Ser Pro Ala Glu Asn Ser Gln Gln Leu Pro Cys
                565                 570                 575

Met Arg Ser Thr His Met Pro Ser Ser Ser Val Thr His Arg Ile Pro
            580                 585                 590

Val Tyr Ser His Arg Glu Glu His Gly Tyr Thr Gly Ser Tyr Asn Tyr
        595                 600                 605

Gly Ser Tyr Gly Asn Gln His Pro His Pro Leu Gln Asn Gln Tyr Pro
        610                 615                 620

Ala Leu Pro His Asp Thr Ala Ile Ser Gly Pro Leu His Tyr Ser Pro
625                 630                 635                 640

Tyr His Arg Ser Ser Ala Gln Tyr Pro Phe Asn Ser Pro Thr Ser Arg
                645                 650                 655

Met Glu Pro Cys Leu Met Ser Ser Thr Pro Arg Leu His Pro Thr Pro
            660                 665                 670

Val Thr Pro Arg Trp Pro Glu Val Pro Thr Ala Asn Ala Cys Tyr Thr
        675                 680                 685

Ser Pro Ser Val His Ser Thr Arg Tyr Gly Asn Ser Ser Asp Met Tyr
        690                 695                 700

Thr Pro Leu Thr Thr Arg Arg Asn Ser Glu Tyr Glu His Met Gln His
705                 710                 715                 720

Phe Pro Gly Phe Ala Tyr Ile Asn Gly Glu Ala Ser Thr Gly Trp Ala
                725                 730                 735

Lys

<210> SEQ ID NO 7
<211> LENGTH: 3603
<212> TYPE: DNA
<213> ORGANISM: Homo sapiens
<220> FEATURE:
<221> NAME/KEY: CDS
<222> LOCATION: (68)..(2275)

<400> SEQUENCE: 7
ctctagcaca ggggatcccc aaacatcagg actttggggg ggcgcctgtg ctgtccatgg      60 gaagagc atg cat tgt ggg tta ctg gag gaa ccc gac atg gat tcc aca       109
        Met His Cys Gly Leu Leu Glu Glu Pro Asp Met Asp Ser Thr
        1               5                   10 gag agc tgg att gaa aga tgt ctc aac gaa agt gaa aac aaa cgt tat       157
Glu Ser Trp Ile Glu Arg Cys Leu Asn Glu Ser Glu Asn Lys Arg Tyr
15              20                  25                  30 tcc agc cac aca tct ctg ggg aat gtt tct aat gat gaa aat gag gaa       205
Ser Ser His Thr Ser Leu Gly Asn Val Ser Asn Asp Glu Asn Glu Glu
                35                  40                  45 aaa gaa aat aat aga gca tcc aag ccc cac tcc act cct gct act ctg       253
Lys Glu Asn Asn Arg Ala Ser Lys Pro His Ser Thr Pro Ala Thr Leu
            50                  55                  60 caa tgg ctg gag gag aac tat gag att gca gag ggg gtc tgc atc cct       301
```

-continued

| | | | | | | | | | | | | |
|---|---|---|---|---|---|---|---|---|---|---|---|---|
| Gln | Trp | Leu | Glu | Glu | Asn | Tyr | Glu | Ile | Ala | Glu | Gly | Val | Cys | Ile | Pro |
| | | 65 | | | | 70 | | | | 75 | | |

```
cgc agt gcc ctc tat atg cat tac ctg gat ttc tgc gag aag aat gat    349
Arg Ser Ala Leu Tyr Met His Tyr Leu Asp Phe Cys Glu Lys Asn Asp
        80                  85                  90 acc caa cct gtc aat gct gcc agc ttt gga aag atc ata agg cag cag    397
Thr Gln Pro Val Asn Ala Ala Ser Phe Gly Lys Ile Ile Arg Gln Gln
 95                 100                 105                 110 ttt cct cag tta acc acc aga aga ctc ggg acc cga gga cag tca aag    445
Phe Pro Gln Leu Thr Thr Arg Arg Leu Gly Thr Arg Gly Gln Ser Lys
                115                 120                 125 tac cat tac tat ggc att gca gtg aaa gaa agc tcc caa tat tat gat    493
Tyr His Tyr Tyr Gly Ile Ala Val Lys Glu Ser Ser Gln Tyr Tyr Asp
                130                 135                 140 gtg atg tat tcc aag aaa gga gct gcc tgg gtg agt gag acg ggc aag    541
Val Met Tyr Ser Lys Lys Gly Ala Ala Trp Val Ser Glu Thr Gly Lys
            145                 150                 155 aaa gaa gtg agc aaa cag aca gtg gca tat tca ccc cgg tcc aaa ctc    589
Lys Glu Val Ser Lys Gln Thr Val Ala Tyr Ser Pro Arg Ser Lys Leu
160                 165                 170 gga aca ctg ctg cca gaa ttt ccc aat gtc aaa gat cta aat ctg cca    637
Gly Thr Leu Leu Pro Glu Phe Pro Asn Val Lys Asp Leu Asn Leu Pro
175                 180                 185                 190 gcc agc ctg cct gag gag aag gtt tct acc ttt att atg atg tac aga    685
Ala Ser Leu Pro Glu Glu Lys Val Ser Thr Phe Ile Met Met Tyr Arg
                195                 200                 205 aca cac tgt cag aga ata ctg gac act gta ata aga gcc aac ttt gat    733
Thr His Cys Gln Arg Ile Leu Asp Thr Val Ile Arg Ala Asn Phe Asp
                210                 215                 220 gag gtt caa agt ttc ctt ctg cac ttt tgg caa gga atg ccg ccc cac    781
Glu Val Gln Ser Phe Leu Leu His Phe Trp Gln Gly Met Pro Pro His
                225                 230                 235 atg ctg cct gtg ctg ggc tcc tcc acg gtg gtg aac att gtc ggc gtg    829
Met Leu Pro Val Leu Gly Ser Ser Thr Val Val Asn Ile Val Gly Val
        240                 245                 250 tgt gac tcc atc ctc tac aaa gct atc tcc ggg gtg ctg atg ccc act    877
Cys Asp Ser Ile Leu Tyr Lys Ala Ile Ser Gly Val Leu Met Pro Thr
255                 260                 265                 270 gtg ctg cag gca tta cct gac agc tta act cag gtg att cga aag ttt    925
Val Leu Gln Ala Leu Pro Asp Ser Leu Thr Gln Val Ile Arg Lys Phe
                275                 280                 285 gcc aag caa ctg gat gag tgg cta aaa gtg gct ctc cac gac ctc cca    973
Ala Lys Gln Leu Asp Glu Trp Leu Lys Val Ala Leu His Asp Leu Pro
                290                 295                 300 gaa aac ttg cga aac atc aag ttc gaa ttg tcg aga agg ttc tcc caa   1021
Glu Asn Leu Arg Asn Ile Lys Phe Glu Leu Ser Arg Arg Phe Ser Gln
                305                 310                 315 att ctg aga cgg caa aca tca cta aat cat ctc tgc cag gca tct cga   1069
Ile Leu Arg Arg Gln Thr Ser Leu Asn His Leu Cys Gln Ala Ser Arg
320                 325                 330 aca gtg atc cac agt gca gac atc acg ttc caa atg ctg gaa gac tgg   1117
Thr Val Ile His Ser Ala Asp Ile Thr Phe Gln Met Leu Glu Asp Trp
335                 340                 345                 350 agg aac gtg gac ctg aac agc atc acc aag caa acc ctt tac acc atg   1165
Arg Asn Val Asp Leu Asn Ser Ile Thr Lys Gln Thr Leu Tyr Thr Met
                355                 360                 365 gaa gac tct cgc gat gag cac cgg aaa ctc atc acc caa tta tat cag   1213
Glu Asp Ser Arg Asp Glu His Arg Lys Leu Ile Thr Gln Leu Tyr Gln
                370                 375                 380 gag ttt gac cat ctc ttg gag gag cag tct ccc atc gag tcc tac att   1261
```

```
Glu Phe Asp His Leu Leu Glu Glu Gln Ser Pro Ile Glu Ser Tyr Ile
        385                 390                 395 gag tgg ctg gat acc atg gtt gac cgc tgt gtt gtg aag gtg gct gcc    1309
Glu Trp Leu Asp Thr Met Val Asp Arg Cys Val Val Lys Val Ala Ala
400                 405                 410 aag aga caa ggg tcc ttg aag aaa gtg gcc cag cag ttc ctc ttg atg    1357
Lys Arg Gln Gly Ser Leu Lys Lys Val Ala Gln Gln Phe Leu Leu Met
415                 420                 425                 430 tgg tcc tgt ttc ggc aca agg gtg atc cgg gac atg acc ttg cac agc    1405
Trp Ser Cys Phe Gly Thr Arg Val Ile Arg Asp Met Thr Leu His Ser
                435                 440                 445 gcc ccc agc ttc ggg tct ttt cac cta att cac tta atg ttt gat gac    1453
Ala Pro Ser Phe Gly Ser Phe His Leu Ile His Leu Met Phe Asp Asp
                450                 455                 460 tac gtg ctc tac ctg tta gaa tct ctg cac tgt cag gag cgg gcc aat    1501
Tyr Val Leu Tyr Leu Leu Glu Ser Leu His Cys Gln Glu Arg Ala Asn
                465                 470                 475 gag ctc atg cga gcc atg aag gga gaa gga agc act gca gaa gtc cga    1549
Glu Leu Met Arg Ala Met Lys Gly Glu Gly Ser Thr Ala Glu Val Arg
        480                 485                 490 gaa gag atc atc ttg aca gag gct gcc gca cca acc cct tca cca gtg    1597
Glu Glu Ile Ile Leu Thr Glu Ala Ala Ala Pro Thr Pro Ser Pro Val
495                 500                 505                 510 cca tcg ttt tct cca gca aaa tct gcc aca tct atg gaa gtg cca cct    1645
Pro Ser Phe Ser Pro Ala Lys Ser Ala Thr Ser Met Glu Val Pro Pro
                515                 520                 525 ccc tct tcc cct gtt agc aat cct tcc cct gag tac act ggc ctc agc    1693
Pro Ser Ser Pro Val Ser Asn Pro Ser Pro Glu Tyr Thr Gly Leu Ser
                530                 535                 540 act aca gga gca atg cag tct tac acg tgg tct cta aca tac aca gtg    1741
Thr Thr Gly Ala Met Gln Ser Tyr Thr Trp Ser Leu Thr Tyr Thr Val
                545                 550                 555 acg acg gct gct ggg tcc cca gct gag aac tcc caa cag ctg ccc tgt    1789
Thr Thr Ala Ala Gly Ser Pro Ala Glu Asn Ser Gln Gln Leu Pro Cys
        560                 565                 570 atg agg aac act cat gtg cct tct tcc tcc gtc aca cac agg ata cca    1837
Met Arg Asn Thr His Val Pro Ser Ser Ser Val Thr His Arg Ile Pro
575                 580                 585                 590 gtt tat ccc cac aga gag gaa cat gga tac acg gga agc tat aac tat    1885
Val Tyr Pro His Arg Glu Glu His Gly Tyr Thr Gly Ser Tyr Asn Tyr
                595                 600                 605 ggg agc tat ggc aac cag cat cct cac ccc atg cag agc cag tat ccg    1933
Gly Ser Tyr Gly Asn Gln His Pro His Pro Met Gln Ser Gln Tyr Pro
                610                 615                 620 gcc ctc cct cat gac aca gct atc tct ggg cca ctc cac tat gcc cct    1981
Ala Leu Pro His Asp Thr Ala Ile Ser Gly Pro Leu His Tyr Ala Pro
                625                 630                 635 tac cac agg agc tct gca cag tac cct ttt aat agc ccc act tcc cgg    2029
Tyr His Arg Ser Ser Ala Gln Tyr Pro Phe Asn Ser Pro Thr Ser Arg
        640                 645                 650 atg gaa cct tgt ttg atg agc agt act ccc aga ctg cat cct acc cca    2077
Met Glu Pro Cys Leu Met Ser Ser Thr Pro Arg Leu His Pro Thr Pro
655                 660                 665                 670 gtc act ccc cgc tgg cca gag gtg ccc tca gcc aac acg tgc tac aca    2125
Val Thr Pro Arg Trp Pro Glu Val Pro Ser Ala Asn Thr Cys Tyr Thr
                675                 680                 685 agc ccg tct gtg cat tct gcg agg tac gga aac tct agt gac atg tat    2173
Ser Pro Ser Val His Ser Ala Arg Tyr Gly Asn Ser Ser Asp Met Tyr
                690                 695                 700 aca cct ctg aca acg cgc agg aat tct gaa tat gag cac atg caa cac    2221
```

```
Thr Pro Leu Thr Thr Arg Arg Asn Ser Glu Tyr Glu His Met Gln His
        705                 710                 715 ttt cct ggc ttt gct tac atc aac gga gag gcc tct aca gga tgg gct    2269
Phe Pro Gly Phe Ala Tyr Ile Asn Gly Glu Ala Ser Thr Gly Trp Ala
    720                 725                 730 aaa tga ctgctatcat aggcatccat atttaatatt aataataata attaataata    2325
Lys
735 ataataaacc caacacccat cccccagaag actttatctc tatacattgt aactcatggg  2385 ctattcctaa gtgcccattt tcctaatgaa catgaggatg ggatcaatgt gggatgaata  2445 aactttagtt cagaaacagg acttactaaa agtcagtggg actgggtttc tgtagccaag  2505 ccagacttga ctgtttctgt agagcactat ctcgggcagg ccattctgtg ccttttccct  2565 ctgttccatg actttgcttt gtgttggcaa ccacttctag taagctactg attttcctgt  2625 tgacaaaatc tctttagtct tgaaggatgg atactggaga cagaatctgg tttgtgttct  2685 tggatgggca cataatttac caagagcatt caccttgcca tctgtcttgt cattgtactg  2745 tacaaggaac agccctcaga cgtgttctgc acatcccttc ttcctggtgg taccatccct  2805 atttcctgga gcaccagggc taaatgggga gctatctgga aactctagat tttctgtcat  2865 acccacatct gtcacagtac ctgcattgtc ttggaatgta agcactgtct tgagggaagg  2925 aagaggtctg ttctgtattg ccttaagttg attgaggttt gtaggagact ggttcttcta  2985 catacaagga tttgtcttaa gtttgcacaa tggctagtgt cagcaaaagg caggagaggg  3045 ttttttgtttt ttttttaagt tctatgaaa tgtggattta tggcattgag tatcacactc  3105 agctctgctg tgttaacttt gtgaaactgg atggaacaaa ctttaactta ccaagcacca  3165 agtgtgaaag tgactttcac ggttccttca taaaactata ataatatccg acactttgat  3225 agaaaaaaat tcaaagctgt gcctttgagc ctatactata ctgtgtatgt gtggaaataa  3285 aaatgtattg tacttttgga gaatttttg taggcattt tctgtcagat ttgtagtaat  3345 ttgtgaggtt tgttagagat taatataggt tttctttctg tattataaaa tgcaccaagc  3405 aattatggtg gacctattac cctatgggta agaaatataa ggaaatatga catcggatgt  3465 ttcagcaact gttctgtaaa taaaatcttt gatcacacca ctcagtgtga taattgtgtc  3525 tacagctaaa atggaaatag ttttatctgt acagttgtgc aagatatgaa tggtttcaca  3585 ctcaaataaa aaatattg                                               3603
```

<210> SEQ ID NO 8
<211> LENGTH: 735
<212> TYPE: PRT
<213> ORGANISM: Homo sapiens

<400> SEQUENCE: 8

```
Met His Cys Gly Leu Leu Glu Glu Pro Asp Met Asp Ser Thr Glu Ser
1               5                   10                  15

Trp Ile Glu Arg Cys Leu Asn Glu Ser Glu Asn Lys Arg Tyr Ser Ser
            20                  25                  30

His Thr Ser Leu Gly Asn Val Ser Asn Asp Glu Asn Glu Glu Lys Glu
        35                  40                  45

Asn Asn Arg Ala Ser Lys Pro His Ser Thr Pro Ala Thr Leu Gln Trp
    50                  55                  60

Leu Glu Glu Asn Tyr Glu Ile Ala Glu Gly Val Cys Ile Pro Arg Ser
65                  70                  75                  80

Ala Leu Tyr Met His Tyr Leu Asp Phe Cys Glu Lys Asn Asp Thr Gln
                85                  90                  95
```

```
Pro Val Asn Ala Ala Ser Phe Gly Lys Ile Ile Arg Gln Gln Phe Pro
            100                 105                 110

Gln Leu Thr Thr Arg Arg Leu Gly Thr Arg Gly Gln Ser Lys Tyr His
            115                 120                 125

Tyr Tyr Gly Ile Ala Val Lys Glu Ser Ser Gln Tyr Tyr Asp Val Met
            130                 135                 140

Tyr Ser Lys Lys Gly Ala Ala Trp Val Ser Glu Thr Gly Lys Lys Glu
145                 150                 155                 160

Val Ser Lys Gln Thr Val Ala Tyr Ser Pro Arg Ser Lys Leu Gly Thr
                    165                 170                 175

Leu Leu Pro Glu Phe Pro Asn Val Lys Asp Leu Asn Leu Pro Ala Ser
                180                 185                 190

Leu Pro Glu Glu Lys Val Ser Thr Phe Ile Met Met Tyr Arg Thr His
            195                 200                 205

Cys Gln Arg Ile Leu Asp Thr Val Ile Arg Ala Asn Phe Asp Glu Val
            210                 215                 220

Gln Ser Phe Leu Leu His Phe Trp Gln Gly Met Pro Pro His Met Leu
225                 230                 235                 240

Pro Val Leu Gly Ser Ser Thr Val Val Asn Ile Val Gly Val Cys Asp
                    245                 250                 255

Ser Ile Leu Tyr Lys Ala Ile Ser Gly Val Leu Met Pro Thr Val Leu
                260                 265                 270

Gln Ala Leu Pro Asp Ser Leu Thr Gln Val Ile Arg Lys Phe Ala Lys
            275                 280                 285

Gln Leu Asp Glu Trp Leu Lys Val Ala Leu His Asp Leu Pro Glu Asn
            290                 295                 300

Leu Arg Asn Ile Lys Phe Glu Leu Ser Arg Arg Phe Ser Gln Ile Leu
305                 310                 315                 320

Arg Arg Gln Thr Ser Leu Asn His Leu Cys Gln Ala Ser Arg Thr Val
                    325                 330                 335

Ile His Ser Ala Asp Ile Thr Phe Gln Met Leu Glu Asp Trp Arg Asn
                340                 345                 350

Val Asp Leu Asn Ser Ile Thr Lys Gln Thr Leu Tyr Thr Met Glu Asp
            355                 360                 365

Ser Arg Asp Glu His Arg Lys Leu Ile Thr Gln Leu Tyr Gln Glu Phe
            370                 375                 380

Asp His Leu Leu Glu Glu Gln Ser Pro Ile Glu Ser Tyr Ile Glu Trp
385                 390                 395                 400

Leu Asp Thr Met Val Asp Arg Cys Val Val Lys Val Ala Ala Lys Arg
                    405                 410                 415

Gln Gly Ser Leu Lys Lys Val Ala Gln Gln Phe Leu Leu Met Trp Ser
                420                 425                 430

Cys Phe Gly Thr Arg Val Ile Arg Asp Met Thr Leu His Ser Ala Pro
            435                 440                 445

Ser Phe Gly Ser Phe His Leu Ile His Leu Met Phe Asp Asp Tyr Val
            450                 455                 460

Leu Tyr Leu Leu Glu Ser Leu His Cys Gln Glu Arg Ala Asn Glu Leu
465                 470                 475                 480

Met Arg Ala Met Lys Gly Glu Gly Ser Thr Ala Glu Val Arg Glu Glu
                    485                 490                 495

Ile Ile Leu Thr Glu Ala Ala Ala Pro Thr Pro Ser Pro Val Pro Ser
                500                 505                 510

Phe Ser Pro Ala Lys Ser Ala Thr Ser Met Glu Val Pro Pro Pro Ser
```

```
                515                 520                 525
Ser Pro Val Ser Asn Pro Ser Pro Glu Tyr Thr Gly Leu Ser Thr Thr
    530                 535                 540

Gly Ala Met Gln Ser Tyr Thr Trp Ser Leu Thr Tyr Thr Val Thr Thr
545                 550                 555                 560

Ala Ala Gly Ser Pro Ala Glu Asn Ser Gln Gln Leu Pro Cys Met Arg
                565                 570                 575

Asn Thr His Val Pro Ser Ser Val Thr His Arg Ile Pro Val Tyr
            580                 585                 590

Pro His Arg Glu Glu His Gly Tyr Thr Gly Ser Tyr Asn Tyr Gly Ser
            595                 600                 605

Tyr Gly Asn Gln His Pro His Pro Met Gln Ser Gln Tyr Pro Ala Leu
    610                 615                 620

Pro His Asp Thr Ala Ile Ser Gly Pro Leu His Tyr Ala Pro Tyr His
625                 630                 635                 640

Arg Ser Ser Ala Gln Tyr Pro Phe Asn Ser Pro Thr Ser Arg Met Glu
                645                 650                 655

Pro Cys Leu Met Ser Ser Thr Pro Arg Leu His Pro Thr Pro Val Thr
            660                 665                 670

Pro Arg Trp Pro Glu Val Pro Ser Ala Asn Thr Cys Tyr Thr Ser Pro
    675                 680                 685

Ser Val His Ser Ala Arg Tyr Gly Asn Ser Ser Asp Met Tyr Thr Pro
690                 695                 700

Leu Thr Thr Arg Arg Asn Ser Glu Tyr Glu His Met Gln His Phe Pro
705                 710                 715                 720

Gly Phe Ala Tyr Ile Asn Gly Glu Ala Ser Thr Gly Trp Ala Lys
                725                 730                 735

<210> SEQ ID NO 9
<211> LENGTH: 3003
<212> TYPE: DNA
<213> ORGANISM: Danio rerio
<220> FEATURE:
<221> NAME/KEY: CDS
<222> LOCATION: (89)..(2296)

<400> SEQUENCE: 9
ccacgcgtcc gcggagggaa ctgaggaggg ggagtcctgc acggagccat tttctcagag      60
gagcccctgg aacgtgcatg ggaagagg atg ctt tgt ggg ctg ctg gaa gag       112
                                Met Leu Cys Gly Leu Leu Glu Glu
                                  1               5 cct gac atg gat tcc aca gag agc tgg att gaa aga tgt ctg aac gaa      160
Pro Asp Met Asp Ser Thr Glu Ser Trp Ile Glu Arg Cys Leu Asn Glu
    10                  15                  20 agc gag agc aag cgc ttc tcc agc cac tct tct att gga aat att tcc      208
Ser Glu Ser Lys Arg Phe Ser Ser His Ser Ser Ile Gly Asn Ile Ser
25                  30                  35                  40 aac gac gaa aac gaa gag aag gaa aat aac cga gca tct aag cca cat      256
Asn Asp Glu Asn Glu Glu Lys Glu Asn Asn Arg Ala Ser Lys Pro His
                45                  50                  55 tca aca cct gct aca tta caa tgg ttg gag gag aac tac gag atc gca      304
Ser Thr Pro Ala Thr Leu Gln Trp Leu Glu Glu Asn Tyr Glu Ile Ala
            60                  65                  70 gag ggt gtg tgt att cct cgc atc gcc ctg tac atg cac tac ctg gac      352
Glu Gly Val Cys Ile Pro Arg Ile Ala Leu Tyr Met His Tyr Leu Asp
    75                  80                  85 ttc tgc gaa aaa ctg gac tca cag cca gtc aat gct gca agc ttc gga      400
Phe Cys Glu Lys Leu Asp Ser Gln Pro Val Asn Ala Ala Ser Phe Gly
```

```
                 90                  95                 100
aag ata ata agg cag cag ttt cct cag ttg acc acg cgg aga tta gga       448
Lys Ile Ile Arg Gln Gln Phe Pro Gln Leu Thr Thr Arg Arg Leu Gly
105                 110                 115                 120 act aga ggt caa tca aag tat cat tac tat ggc atc gca gtg aag gag       496
Thr Arg Gly Gln Ser Lys Tyr His Tyr Tyr Gly Ile Ala Val Lys Glu
                125                 130                 135 agc tcc cag tac tac gat gtg atg tac tct aaa aag ggc gct gcg tgg       544
Ser Ser Gln Tyr Tyr Asp Val Met Tyr Ser Lys Lys Gly Ala Ala Trp
            140                 145                 150 gtg aac gag acg ggc aag aaa gag gtc acc aaa cag aca gta gcg tat       592
Val Asn Glu Thr Gly Lys Lys Glu Val Thr Lys Gln Thr Val Ala Tyr
        155                 160                 165 tca ccg cgc tcc aag ctg ggc act ctc ctg cca gac ttt cca aat gtc       640
Ser Pro Arg Ser Lys Leu Gly Thr Leu Leu Pro Asp Phe Pro Asn Val
    170                 175                 180 aaa gac cta aat ctg ccc gcc agt ctg cca gag gag aag gtc tcg acc       688
Lys Asp Leu Asn Leu Pro Ala Ser Leu Pro Glu Glu Lys Val Ser Thr
185                 190                 195                 200 ttt att atg atg tac aga act cac tgc cag agg ata ctg gat act gtc       736
Phe Ile Met Met Tyr Arg Thr His Cys Gln Arg Ile Leu Asp Thr Val
                205                 210                 215 ata cgc gcc aac ttc gat gag gtt cag agc ttc ctg ttg cac ttt tgg       784
Ile Arg Ala Asn Phe Asp Glu Val Gln Ser Phe Leu Leu His Phe Trp
            220                 225                 230 cag ggc atg ccg ccc cac atg ctc cct gtc ctg ggc tct tct aca gtg       832
Gln Gly Met Pro Pro His Met Leu Pro Val Leu Gly Ser Ser Thr Val
        235                 240                 245 gtc aac ata gtg ggt gtg tgt gac tcc ata ttg tac aag gcc atc tca       880
Val Asn Ile Val Gly Val Cys Asp Ser Ile Leu Tyr Lys Ala Ile Ser
    250                 255                 260 ggc gtc ctc atg ccc acc gtc cta caa gct ctg cct gac agc ctc act       928
Gly Val Leu Met Pro Thr Val Leu Gln Ala Leu Pro Asp Ser Leu Thr
265                 270                 275                 280 cag gtg atc agg aag ttt gcc aag cag ctg gac gag tgg ctg aag gtg       976
Gln Val Ile Arg Lys Phe Ala Lys Gln Leu Asp Glu Trp Leu Lys Val
                285                 290                 295 gct tta cat gac ctg ccc gaa aac ctg cgc aac att aag ttt gaa ttg      1024
Ala Leu His Asp Leu Pro Glu Asn Leu Arg Asn Ile Lys Phe Glu Leu
            300                 305                 310 tca aga aga ttt tct cag att ctc aaa cga caa aca tca tta aac cac      1072
Ser Arg Arg Phe Ser Gln Ile Leu Lys Arg Gln Thr Ser Leu Asn His
        315                 320                 325 ctc tgt cag gcc tct cga aca gtg atc cac agt gca gac atc acc ttt      1120
Leu Cys Gln Ala Ser Arg Thr Val Ile His Ser Ala Asp Ile Thr Phe
    330                 335                 340 cag atg ctc gag gac tgg agg aac gta gac ctc aac agc atc act aaa      1168
Gln Met Leu Glu Asp Trp Arg Asn Val Asp Leu Asn Ser Ile Thr Lys
345                 350                 355                 360 caa act ctt tat act atg gaa gac tcc aga gaa gac cag agg aga ctc      1216
Gln Thr Leu Tyr Thr Met Glu Asp Ser Arg Glu Asp Gln Arg Arg Leu
                365                 370                 375 atc atc caa ttg tat caa gaa ttt gac aga ctg cta gag gac cag tct      1264
Ile Ile Gln Leu Tyr Gln Glu Phe Asp Arg Leu Leu Glu Asp Gln Ser
            380                 385                 390 cca att gaa gcc tac atc gag tgg ctg gac tct atg gtg gag aga tgt      1312
Pro Ile Glu Ala Tyr Ile Glu Trp Leu Asp Ser Met Val Glu Arg Cys
        395                 400                 405 gtt gtg agg gtg gcg ggg aag aga ccc gga tct ctg aag agg gta gct      1360
Val Val Arg Val Ala Gly Lys Arg Pro Gly Ser Leu Lys Arg Val Ala
```

-continued

|  |  |
|---|---|
| cag cag ttc ctg ctc atg tgg tcg tgt ttt ggg aca aga gtt atc cgg<br>Gln Gln Phe Leu Leu Met Trp Ser Cys Phe Gly Thr Arg Val Ile Arg<br>425                             430                          435                          440 | 1408 |
| gat atg acg ctg cat agt gca cca agc ttt ggc tcg ttc cat ctg att<br>Asp Met Thr Leu His Ser Ala Pro Ser Phe Gly Ser Phe His Leu Ile<br>                           445                          450                          455 | 1456 |
| cac ctc atg ttt gat gac tat gta ctt tac ctg ctt gaa tct ctg cac<br>His Leu Met Phe Asp Asp Tyr Val Leu Tyr Leu Leu Glu Ser Leu His<br>              460                          465                          470 | 1504 |
| tgc caa gag aga gcc aat gaa ctg atg agg gcg atg aaa gga gag ggc<br>Cys Gln Glu Arg Ala Asn Glu Leu Met Arg Ala Met Lys Gly Glu Gly<br>                     475                          480                          485 | 1552 |
| gca cca gca gat act gga gaa gag ctg atg ctg atg agc tcc act cca<br>Ala Pro Ala Asp Thr Gly Glu Glu Leu Met Leu Met Ser Ser Thr Pro<br>490                             495                          500 | 1600 |
| aca tct acg tca cct gga ccc tac tct cct gcc aaa tct gtt cac tcg<br>Thr Ser Thr Ser Pro Gly Pro Tyr Ser Pro Ala Lys Ser Val His Ser<br>505                             510                          515                          520 | 1648 |
| gtg ggc gta ccc gca gta ggg tcc ccc aat tca gcc cag tct ccg gag<br>Val Gly Val Pro Ala Val Gly Ser Pro Asn Ser Ala Gln Ser Pro Glu<br>                         525                          530                          535 | 1696 |
| tac acc agc ata tcg gcc aca aca gga gct gtt cag tca tat acc tgg<br>Tyr Thr Ser Ile Ser Ala Thr Thr Gly Ala Val Gln Ser Tyr Thr Trp<br>              540                          545                          550 | 1744 |
| tcc ctt aca tac aca gtg aca act tca ggc ggc agc cca acc gag ccc<br>Ser Leu Thr Tyr Thr Val Thr Thr Ser Gly Gly Ser Pro Thr Glu Pro<br>                   555                          560                          565 | 1792 |
| gga tcc cag ctg tcc tgc atg aga ggc gga cct gcg tta cac gga tca<br>Gly Ser Gln Leu Ser Cys Met Arg Gly Gly Pro Ala Leu His Gly Ser<br>570                             575                          580 | 1840 |
| tcc tcc gca cac cgg atg cca gtt tac cca cat cgg gat gag cac ggg<br>Ser Ser Ala His Arg Met Pro Val Tyr Pro His Arg Asp Glu His Gly<br>585                             590                          595                          600 | 1888 |
| tac act ggc agc tat aat tac agc agc tac gca aac cag cac cat cat<br>Tyr Thr Gly Ser Tyr Asn Tyr Ser Ser Tyr Ala Asn Gln His His His<br>                         605                          610                          615 | 1936 |
| gcc att cag agt caa tac tcc agt tta acc cat gaa gca ggg ctg ccc<br>Ala Ile Gln Ser Gln Tyr Ser Ser Leu Thr His Glu Ala Gly Leu Pro<br>              620                          625                          630 | 1984 |
| act cct ttg cat tat tcc tca tac cac cgc acc tcc gca cag tat ccg<br>Thr Pro Leu His Tyr Ser Ser Tyr His Arg Thr Ser Ala Gln Tyr Pro<br>                   635                          640                          645 | 2032 |
| ctc aac agt caa atg tcc aga atg gag tcg tgt cta atg agc ggc tct<br>Leu Asn Ser Gln Met Ser Arg Met Glu Ser Cys Leu Met Ser Gly Ser<br>650                             655                          660 | 2080 |
| cct ctc cta cac tcc agt cca gtg acc cct cga tgg ccc gat gtg ccc<br>Pro Leu Leu His Ser Ser Pro Val Thr Pro Arg Trp Pro Asp Val Pro<br>665                             670                          675                          680 | 2128 |
| tct gcc aac agc tgt tac tcc agt ccc acc gtc cac gca tcc cgc tac<br>Ser Ala Asn Ser Cys Tyr Ser Ser Pro Thr Val His Ala Ser Arg Tyr<br>                         685                          690                          695 | 2176 |
| tcc acc gga gac atg tac tcg ccc ctt gcc cca cgc agg aac tct gaa<br>Ser Thr Gly Asp Met Tyr Ser Pro Leu Ala Pro Arg Arg Asn Ser Glu<br>              700                          705                          710 | 2224 |
| tac gag cac gca caa cac ttt cca gga ttc gcc tat att aac ggg gag<br>Tyr Glu His Ala Gln His Phe Pro Gly Phe Ala Tyr Ile Asn Gly Glu<br>                   715                          720                          725 | 2272 |
| gcc acg acc gga tgg gca aaa tga taaaccagcg gtggtccata tttaacacta<br>Ala Thr Thr Gly Trp Ala Lys | 2326 |

-continued

```
          730         735
ttacagagaa tgtatctgag aatggcaacg gtgtttttat tggtgtggtc agtgtttaca    2386
gtgcaaagct gccaatgaaa gttgattcgc aatcattgtg agagaaaacg ggacatccta    2446
aaaaaacgac tgaatgattt aagttattta taaagtctaa atttggtata cttttaatta    2506
aatatacatt ctatgcacaa attaacacag aacgaacaga acatgttaaa ttgcccgtta    2566 aatactttc  tcccatatta gaaagaaaat gcttaatttg gcttaatgct ttaaagaagt    2626
gatgtgtata tacagttgaa gtcagaatta ttagtcgccc tgtttatttt ttcctccaac    2686
ttctgtttaa cggagagaag aattttttaa cacatttcta aatataatag ttttaataac    2746
tcatttaaaa taactgattt attttatctt tgccatgaac acagtgcata atatttgact    2806
agatattttt aaagacactt ctatacagct taaagtgaca tttaaaggct taactaggtt    2866
aattaggtta actaggcagg atagggcaat taggccagtt attttataac gatggtttgt    2926
tctgtagact atcggaaaaa ataatttga  ccttaaaatg gtgtttaaaa aattaaaaac    2986 ttctttttatt ctagccg                                                  3003
```

<210> SEQ ID NO 10
<211> LENGTH: 735
<212> TYPE: PRT
<213> ORGANISM: Danio rerio

<400> SEQUENCE: 10

```
Met Leu Cys Gly Leu Leu Glu Glu Pro Asp Met Asp Ser Thr Glu Ser
1               5                   10                  15

Trp Ile Glu Arg Cys Leu Asn Glu Ser Glu Ser Lys Arg Phe Ser Ser
            20                  25                  30

His Ser Ser Ile Gly Asn Ile Ser Asn Asp Glu Asn Glu Glu Lys Glu
        35                  40                  45

Asn Asn Arg Ala Ser Lys Pro His Ser Thr Pro Ala Thr Leu Gln Trp
    50                  55                  60

Leu Glu Glu Asn Tyr Glu Ile Ala Glu Gly Val Cys Ile Pro Arg Ile
65                  70                  75                  80

Ala Leu Tyr Met His Tyr Leu Asp Phe Cys Glu Lys Leu Asp Ser Gln
                85                  90                  95

Pro Val Asn Ala Ala Ser Phe Gly Lys Ile Ile Arg Gln Gln Phe Pro
            100                 105                 110

Gln Leu Thr Thr Arg Arg Leu Gly Thr Arg Gly Gln Ser Lys Tyr His
        115                 120                 125

Tyr Tyr Gly Ile Ala Val Lys Glu Ser Ser Gln Tyr Tyr Asp Val Met
    130                 135                 140

Tyr Ser Lys Lys Gly Ala Ala Trp Val Asn Glu Thr Gly Lys Lys Glu
145                 150                 155                 160

Val Thr Lys Gln Thr Val Ala Tyr Ser Pro Arg Ser Lys Leu Gly Thr
                165                 170                 175

Leu Leu Pro Asp Phe Pro Asn Val Lys Asp Leu Asn Leu Pro Ala Ser
            180                 185                 190

Leu Pro Glu Glu Lys Val Ser Thr Phe Ile Met Met Tyr Arg Thr His
        195                 200                 205

Cys Gln Arg Ile Leu Asp Thr Val Ile Arg Ala Asn Phe Asp Glu Val
    210                 215                 220

Gln Ser Phe Leu Leu His Phe Trp Gln Gly Met Pro Pro His Met Leu
225                 230                 235                 240

Pro Val Leu Gly Ser Ser Thr Val Val Asn Ile Val Gly Val Cys Asp
```

-continued

```
                    245                 250                 255
Ser Ile Leu Tyr Lys Ala Ile Ser Gly Val Leu Met Pro Thr Val Leu
                260                 265                 270
Gln Ala Leu Pro Asp Ser Leu Thr Gln Val Ile Arg Lys Phe Ala Lys
            275                 280                 285
Gln Leu Asp Glu Trp Leu Lys Val Ala Leu His Asp Leu Pro Glu Asn
        290                 295                 300
Leu Arg Asn Ile Lys Phe Glu Leu Ser Arg Arg Phe Ser Gln Ile Leu
305                 310                 315                 320
Lys Arg Gln Thr Ser Leu Asn His Leu Cys Gln Ala Ser Arg Thr Val
                325                 330                 335
Ile His Ser Ala Asp Ile Thr Phe Gln Met Leu Glu Asp Trp Arg Asn
                340                 345                 350
Val Asp Leu Asn Ser Ile Thr Lys Gln Thr Leu Tyr Thr Met Glu Asp
            355                 360                 365
Ser Arg Glu Asp Gln Arg Arg Leu Ile Ile Gln Leu Tyr Gln Glu Phe
        370                 375                 380
Asp Arg Leu Leu Glu Asp Gln Ser Pro Ile Glu Ala Tyr Ile Glu Trp
385                 390                 395                 400
Leu Asp Ser Met Val Glu Arg Cys Val Val Arg Val Ala Gly Lys Arg
                405                 410                 415
Pro Gly Ser Leu Lys Arg Val Ala Gln Phe Leu Leu Met Trp Ser
                420                 425                 430
Cys Phe Gly Thr Arg Val Ile Arg Asp Met Thr Leu His Ser Ala Pro
            435                 440                 445
Ser Phe Gly Ser Phe His Leu Ile His Leu Met Phe Asp Asp Tyr Val
        450                 455                 460
Leu Tyr Leu Leu Glu Ser Leu His Cys Gln Glu Arg Ala Asn Glu Leu
465                 470                 475                 480
Met Arg Ala Met Lys Gly Glu Gly Ala Pro Ala Asp Thr Gly Glu Glu
                485                 490                 495
Leu Met Leu Met Ser Ser Thr Pro Thr Ser Thr Ser Pro Gly Pro Tyr
                500                 505                 510
Ser Pro Ala Lys Ser Val His Ser Val Gly Val Pro Ala Val Gly Ser
            515                 520                 525
Pro Asn Ser Ala Gln Ser Pro Glu Tyr Thr Ser Ile Ser Ala Thr Thr
        530                 535                 540
Gly Ala Val Gln Ser Tyr Thr Trp Ser Leu Thr Tyr Thr Val Thr Thr
545                 550                 555                 560
Ser Gly Gly Ser Pro Thr Glu Pro Gly Ser Gln Leu Ser Cys Met Arg
                565                 570                 575
Gly Gly Pro Ala Leu His Gly Ser Ser Ala His Arg Met Pro Val
                580                 585                 590
Tyr Pro His Arg Asp Glu His Gly Tyr Thr Gly Ser Tyr Asn Tyr Ser
            595                 600                 605
Ser Tyr Ala Asn Gln His His His Ala Ile Gln Ser Gln Tyr Ser Ser
        610                 615                 620
Leu Thr His Glu Ala Gly Leu Pro Thr Pro Leu His Tyr Ser Ser Tyr
625                 630                 635                 640
His Arg Thr Ser Ala Gln Tyr Pro Leu Asn Ser Gln Met Ser Arg Met
                645                 650                 655
Glu Ser Cys Leu Met Ser Gly Ser Pro Leu Leu His Ser Ser Pro Val
                660                 665                 670
```

```
Thr Pro Arg Trp Pro Asp Val Pro Ser Ala Asn Ser Cys Tyr Ser Ser
        675                 680                 685

Pro Thr Val His Ala Ser Arg Tyr Ser Thr Gly Asp Met Tyr Ser Pro
        690                 695                 700

Leu Ala Pro Arg Arg Asn Ser Glu Tyr Glu His Ala Gln His Phe Pro
705                 710                 715                 720

Gly Phe Ala Tyr Ile Asn Gly Glu Ala Thr Thr Gly Trp Ala Lys
                725                 730                 735

<210> SEQ ID NO 11
<211> LENGTH: 4001
<212> TYPE: DNA
<213> ORGANISM: Homo sapiens

<400> SEQUENCE: 11
```

| | | | | | |
|---|---|---|---|---|---|
| gtgagtgctg | ggtttggaaa | gtacagggac | tgttgagatt | acagcagtgg | aggcagagca | 60 |
| caccccgtga | tctaaaaggg | atccgccctg | caccttcctc | tttcatgctg | ctcgttcatc | 120 |
| cattccaggg | gattcagcag | ccacccaggt | ctgcacaagc | agtgccaact | ccacaccttt | 180 |
| gtgggtctgc | ctggctgtca | ttgccactgg | gctactggga | agttttaagg | gcccttcaaa | 240 |
| cccttctctc | ttgctgccaa | gtcttccctc | ctcatgtcac | atcctggtac | caatagctac | 300 |
| tcattgctca | agtcagaaac | ctgggaatcc | cttctccctc | cccatccctg | ccacaacta | 360 |
| atcaacatca | aggctgggaa | tacagcttcc | ttggtatctc | ctgaaccctg | ccccaactgc | 420 |
| catgtacctg | tgtcaggtca | tcctgatccc | tccctcccac | cccctcctgc | aaccaacccc | 480 |
| catctggcca | ccacacagtt | tgagatctct | tcacattttg | tgatctcttc | aaaatgtaga | 540 |
| tttagtccta | tatgcaccaa | acccttccag | ggtacatttc | ttggcatggc | cctagcttac | 600 |
| ctccccatga | aatggcctgt | taatcctctc | ttcctctctt | gggttccgtg | tgcagccagg | 660 |
| ccaggctcca | gtcccaaaca | cactccacag | gttctcctct | tcgcctgtgc | ctctgtctgt | 720 |
| aacaccctca | accccttgt | ctggctaatt | cagctcctgg | gtcaccactt | cctccaggag | 780 |
| gcctgccttg | acaccagcct | cccaggatca | gtcacattgc | cctctctttg | ctctcacagc | 840 |
| acccacaatt | tccccatcac | cccctccctg | ccctgtgct | atgttctatt | gagatttcaa | 900 |
| gcctctgcag | gataggaatt | ggataattca | ttactgtgtc | cacagtgtct | gtcaagggca | 960 |
| agagagccac | acagaacccc | agtagttctc | ctaaaagtgg | agacgacaat | aatatgtatt | 1020 |
| agttgtgttg | tgaggatgaa | atgaactaat | gcatggaaga | cgcctgaacc | cgtggaaaca | 1080 |
| cataatgaat | acattaatag | taaatggtag | ctattactat | ttatgatgtt | gacagcatta | 1140 |
| aatctaagca | acattttat | tgaagtatga | atacattcc | aaaaaatgcg | caaaatcaca | 1200 |
| agtgtcacag | tcagtgaatt | gtcacaaatg | acacccttgt | gactagcccc | tggataccat | 1260 |
| tacttttaag | ctcaaatgtc | agcttctcag | agaggccctc | ccttgacttc | gtctcccacc | 1320 |
| tcttaattct | atgttgtata | tattatctgt | ttcccctcac | tcccatgtaa | gcttcaggag | 1380 |
| agcaagattt | tttttttttt | tttttggtc | tattttgttc | actgatgtag | cctccgcttc | 1440 |
| ctagaatagt | tctggacaca | tagtagatgc | acaataaaaa | tttgccaagg | aacgaatgag | 1500 |
| cgattattat | tttcatttct | ttaagctccc | aggcgctgca | gcatggtcat | gcccgagaac | 1560 |
| tcgtgccatc | ccaggtgaag | cagcgctggg | ccgggaccag | ccgcacctgg | cccggctctg | 1620 |
| agctgtgctg | ggctggctcc | gggttcttcc | gcctcactcc | tggcctgtga | gcccggctca | 1680 |
| cctcacccta | cccacctcca | ctctgcgtgc | aaaaattata | ataataatag | caacaataat | 1740 |
| agtctcatcc | gccctggaga | ccacccgtgc | ccccgtggca | tccctcaagg | actctccggg | 1800 |

```
cggtggcagc cgcccaccct ggggacgcgc tccttgctgc caccggaacg cccctggcca   1860
ggctccatct acgcgctgtc agaccctccc gccgtctgaa gaaggctttt actcttcagc   1920
ctattccagt ggcagagaag ctaaggctac aaaggcgaac gcgaacagtc agatctgact   1980
tcgaattccg ctgtcattgc tgccaggcgc accacgagga cgcgcggtga ccgccaccat   2040
ggcattcggc tgccaaaggt ttccatcgac ctctttccca tcaccagcat cgcagcggga   2100
aagaatgtgc ctggcgccct tctgggcact gggcatgggg tggtgaacaa agtcctccag   2160
aaataaaccg ggtaatgagc ccggcagcgg ccggggcagg aagggacctt cgcagagagt   2220
ggtcaggcac agcccctccg aggaggcgac gctcagctga gaccagggtg acgcaaaggt   2280
gtcggccggt taggcacctg tgaggaagga ggagccggca gagtgccaag tagagggaac   2340
agcaaatgcc cggctccttt tataaccact gcttcagtta tcttccccca aagcttgaga   2400
gggggcaact ttgctacatt tcacagacga ggaagctgag gcccagaacg atgaaggaat   2460
ttacagagct gggattcgaa ccccgcgcta ccgtcagtcc atcccgggct ctgtccagcc   2520
ggtaccgcgc gccgccttct tcctcccgca ccgtgacctt aactcggcac gtgctggccc   2580
ctcgggctcc ccagtctccg tacattgtcc cactcagctc tgattgtggg aggggggcgg   2640
accgaggggg cgggggcgt  ctttccgaag gatcgcggaa agccgcgcgc tgccaggggc   2700
ccggggttag agaccccac  tcccgcacgg cgttagggac tccgcgcttc ccgcccccg    2760
ccgcggcccg ccggctctgc ctctgtccat ggtcaaagca cccggggtaa tccgcctttc   2820
tcttccgccc gccgggcccc attcatattc taatcacagc gcggccgacc cgcgaacggc   2880
cactttatcg gggcccgcag gagacgcagc ttgctccccc tcacttccac ttccagcacc   2940
ccccggccct cgcccccctc tttctgcact ttcaactccg ccgaggaggg ggtccctggg   3000
aaaaccgcgt ccccacttgg atgccggggc ttctcacaaa cttcgaggcc gactggggga   3060
cggcggtggg gtggggaggg caggggaggg gcggaggaac agagacagac agactgacag   3120
agttacggga agaggcgggg gagggggac  agtacagaga gaccgagggg gatagagaca   3180
gagaggggca gagtcctagg gggagacaaa gagaagtgga ggcagggtct ggacagagac   3240
actagcagcc aaggaaggag aaatggacag agacagagac acagaggacg agaggacag   3300
agagctagaa acagacaccg ggagacaggc ggagagagac agcgagatgg aaggagagaa   3360
acaggatgaa ggacccaggc ccagaggaag acagaaagtt ctggaggagg cgaaccagcc   3420
actcacctcc tccccgccta gcggccttgt tacgctcata ttggggcatg ggtcttagg    3480
gattcagttc cccttcccca ccctttcccc ttcaagctcg cttcactccc cacgcgtgtc   3540
tgcggatccg cgtgcaaggg gtcaagacat accccctccc gcattctcag ggccaccacc   3600
cgaaatctaa cccaggacca aaatggggggg tgggtggggg cgcaagagaa ggaagggagt   3660
ggggccccac tcgtggtagc gcaggcgact cccccaggctc caggagttcc ccgcggctcc   3720
cccccgccc gcgcccccct cccggcctgc cagcacggcg cggggcccga tggtgggaa    3780
gggccgggag gggaggggg  ccacatctaa gccaattttg atttcgccta taatgagtgc   3840
cgggcgaagg ctgagaagg  cctctggaac tttaaataag aaaacgttg  ctaatgctat   3900
aatagaaggg ggaagtcgga gggctgggat tgcgtcgctc tgagcccccc ttttcggagg   3960
cggcttttct tattcaaaac aggcccacaa tgggcttcac a                      4001
```

<210> SEQ ID NO 12
<211> LENGTH: 207
<212> TYPE: DNA
<213> ORGANISM: Mus musculus -continued

```
<400> SEQUENCE: 12 gagggggca  gatctaagcc  aattttgatt  tcgtctataa  tgagtgccgg  gctaaggctg    60
gagaaggcct  ctggaactt   aaataagaaa  aacgttgcta  atgctataat  agaaggggga   120
agtcggaggg  ctgggattgc  gtcgctctga  gccccctttt  tcggaggcgg  cttttcttat   180
tcaaaacagg  cccacaatgg  gcttcac                                         207

<210> SEQ ID NO 13
<211> LENGTH: 158
<212> TYPE: PRT
<213> ORGANISM: Danio rerio

<400> SEQUENCE: 13

Met Leu Cys Gly Leu Leu Glu Glu Pro Asp Met Asp Ser Thr Glu Ser
1               5                   10                  15

Trp Ile Glu Arg Cys Leu Asn Glu Ser Glu Ser Lys Arg Phe Ser Ser
            20                  25                  30

His Ser Ser Ile Gly Asn Ile Ser Asn Asp Glu Asn Glu Glu Lys Glu
        35                  40                  45

Asn Asn Arg Ala Ser Lys Pro His Ser Thr Pro Ala Thr Leu Gln Trp
    50                  55                  60

Leu Glu Glu Asn Tyr Glu Ile Ala Glu Gly Val Cys Ile Pro Arg Ile
65                  70                  75                  80

Ala Leu Tyr Met His Tyr Leu Asp Phe Cys Glu Lys Leu Asp Ser Gln
                85                  90                  95

Pro Val Asn Ala Ala Ser Phe Gly Lys Ile Ile Arg Gln Gln Phe Pro
            100                 105                 110

Gln Leu Thr Thr Arg Arg Leu Gly Thr Arg Gly Gln Ser Lys Tyr His
        115                 120                 125

Tyr Tyr Gly Ile Ala Val Lys Glu Ser Ser Gln Tyr Tyr Asp Val Met
    130                 135                 140

Tyr Ser Lys Lys Gly Ala Ala Trp Val Asn Glu Thr Gly Lys
145                 150                 155

<210> SEQ ID NO 14
<211> LENGTH: 3369
<212> TYPE: DNA
<213> ORGANISM: Homo sapiens
<220> FEATURE:
<221> NAME/KEY: CDS
<222> LOCATION: (110)..(2035)

<400> SEQUENCE: 14
aggtgggaag  gcagttatga  cagttgagaa  gtagtagaag  acacggaagg  cacagaaggc    60
agacttcgct  cagcacaaag  aagaattttc  tgataaccat  actggcaaa atg aac tgg   118
                                                        Met Asn Trp
                                                          1 gct gcc ttc gga ggg tct gaa ttc ttc atc cca gaa ggc att cag ata         166
Ala Ala Phe Gly Gly Ser Glu Phe Phe Ile Pro Glu Gly Ile Gln Ile
        5                   10                  15 gat tcg aga tgc cca cta agc aga aat atc acg gaa tgg tac cat tac         214
Asp Ser Arg Cys Pro Leu Ser Arg Asn Ile Thr Glu Trp Tyr His Tyr
20                  25                  30                  35 tat ggc att gca gtg aaa gaa agc tcc caa tat tat gat gtg atg tat         262
Tyr Gly Ile Ala Val Lys Glu Ser Ser Gln Tyr Tyr Asp Val Met Tyr
                40                  45                  50 tcc aag aaa gga gct gcc tgg gtg agt gag acg ggc aag aaa gaa gtg         310
Ser Lys Lys Gly Ala Ala Trp Val Ser Glu Thr Gly Lys Lys Glu Val
            55                  60                  65
```

```
agc aaa cag aca gtg gca tat tca ccc cgg tcc aaa ctc gga aca ctg      358
Ser Lys Gln Thr Val Ala Tyr Ser Pro Arg Ser Lys Leu Gly Thr Leu
         70                  75                  80 ctg cca gaa ttt ccc aat gtc aaa gat cta aat ctg cca gcc agc ctg      406
Leu Pro Glu Phe Pro Asn Val Lys Asp Leu Asn Leu Pro Ala Ser Leu
 85                  90                  95 cct gag gag aag gtt tct acc ttt att atg atg tac aga aca cac tgt      454
Pro Glu Glu Lys Val Ser Thr Phe Ile Met Met Tyr Arg Thr His Cys
100                 105                 110                 115 cag aga ata ctg gac act gta ata aga gcc aac ttt gat gag gtt caa      502
Gln Arg Ile Leu Asp Thr Val Ile Arg Ala Asn Phe Asp Glu Val Gln
             120                 125                 130 agt ttc ctt ctg cac ttt tgg caa gga atg ccg ccc cac atg ctg cct      550
Ser Phe Leu Leu His Phe Trp Gln Gly Met Pro Pro His Met Leu Pro
         135                 140                 145 gtg ctg ggc tcc tcc acg gtg gtg aac att gtc ggc gtg tgt gac tcc      598
Val Leu Gly Ser Ser Thr Val Val Asn Ile Val Gly Val Cys Asp Ser
     150                 155                 160 atc ctc tac aaa gct atc tcc ggg gtg ctg atg ccc act gtg ctg cag      646
Ile Leu Tyr Lys Ala Ile Ser Gly Val Leu Met Pro Thr Val Leu Gln
165                 170                 175 gca tta cct gac agc tta act cag gtg att cga aag ttt gcc aag caa      694
Ala Leu Pro Asp Ser Leu Thr Gln Val Ile Arg Lys Phe Ala Lys Gln
180                 185                 190                 195 ctg gat gag tgg cta aaa gtg gct ctc cac gac ctc cca gaa aac ttg      742
Leu Asp Glu Trp Leu Lys Val Ala Leu His Asp Leu Pro Glu Asn Leu
             200                 205                 210 cga aac atc aag ttc gaa ttg tcg aga agg ttc tcc caa att ctg aga      790
Arg Asn Ile Lys Phe Glu Leu Ser Arg Arg Phe Ser Gln Ile Leu Arg
         215                 220                 225 cgg caa aca tca cta aat cat ctc tgc cag gca tct cga aca gtg atc      838
Arg Gln Thr Ser Leu Asn His Leu Cys Gln Ala Ser Arg Thr Val Ile
     230                 235                 240 cac agt gca gac atc acg ttc caa atg ctg gaa gac tgg agg aac gtg      886
His Ser Ala Asp Ile Thr Phe Gln Met Leu Glu Asp Trp Arg Asn Val
245                 250                 255 gac ctg aac agc atc acc aag caa acc ctt tac acc atg gaa gac tct      934
Asp Leu Asn Ser Ile Thr Lys Gln Thr Leu Tyr Thr Met Glu Asp Ser
260                 265                 270                 275 cgc gat gag cac cgg aaa ctc atc acc caa tta tat cag gag ttt gac      982
Arg Asp Glu His Arg Lys Leu Ile Thr Gln Leu Tyr Gln Glu Phe Asp
             280                 285                 290 cat ctc ttg gag gag cag tct ccc atc gag tcc tac att gag tgg ctg     1030
His Leu Leu Glu Glu Gln Ser Pro Ile Glu Ser Tyr Ile Glu Trp Leu
         295                 300                 305 gat acc atg gtt gac cgc tgt gtt gtg aag gtg gct gcc aag aga caa     1078
Asp Thr Met Val Asp Arg Cys Val Val Lys Val Ala Ala Lys Arg Gln
     310                 315                 320 ggg tcc ttg aag aaa gtg gcc cag cag ttc ctc ttg atg tgg tcc tgt     1126
Gly Ser Leu Lys Lys Val Ala Gln Gln Phe Leu Leu Met Trp Ser Cys
325                 330                 335 ttc ggc aca agg gtg atc cgg gac atg acc ttg cac agc gcc ccc agc     1174
Phe Gly Thr Arg Val Ile Arg Asp Met Thr Leu His Ser Ala Pro Ser
340                 345                 350                 355 ttc ggg tct ttt cac cta att cac tta atg ttt gat gac tac gtg ctc     1222
Phe Gly Ser Phe His Leu Ile His Leu Met Phe Asp Asp Tyr Val Leu
             360                 365                 370 tac ctg tta gaa tct ctg cac tgt cag gag cgg gcc aat gag ctc atg     1270
Tyr Leu Leu Glu Ser Leu His Cys Gln Glu Arg Ala Asn Glu Leu Met
         375                 380                 385
```

```
cga gcc atg aag gga gaa gga agc act gca gaa gtc cga gaa gag atc    1318
Arg Ala Met Lys Gly Glu Gly Ser Thr Ala Glu Val Arg Glu Glu Ile
            390                 395                 400 atc ttg aca gag gct gcc gca cca acc cct tca cca gtg cca tcg ttt    1366
Ile Leu Thr Glu Ala Ala Ala Pro Thr Pro Ser Pro Val Pro Ser Phe
    405                 410                 415 tct cca gca aaa tct gcc aca tct gtg gaa gtg cca cct ccc tct tcc    1414
Ser Pro Ala Lys Ser Ala Thr Ser Val Glu Val Pro Pro Pro Ser Ser
420                 425                 430                 435 cct gtt agc aat cct tcc cct gag tac act ggc ctc agc act aca gga    1462
Pro Val Ser Asn Pro Ser Pro Glu Tyr Thr Gly Leu Ser Thr Thr Gly
                440                 445                 450 gca atg cag tct tac acg tgg tct cta aca tac aca gtg acg acg gct    1510
Ala Met Gln Ser Tyr Thr Trp Ser Leu Thr Tyr Thr Val Thr Thr Ala
            455                 460                 465 gct ggg tcc cca gct gag aac tcc caa cag ctg ccc tgt atg agg aac    1558
Ala Gly Ser Pro Ala Glu Asn Ser Gln Gln Leu Pro Cys Met Arg Asn
        470                 475                 480 act cat gtg cct tct tcc tcc gtc aca cac agg ata cca gtt tat ccc    1606
Thr His Val Pro Ser Ser Ser Val Thr His Arg Ile Pro Val Tyr Pro
    485                 490                 495 cac aga gag gaa cat gga tac acg gga agc tat aac tat ggg agc tat    1654
His Arg Glu Glu His Gly Tyr Thr Gly Ser Tyr Asn Tyr Gly Ser Tyr
500                 505                 510                 515 ggc aac cag cat cct cac ccc atg cag agc cag tat ccg gcc ctc cct    1702
Gly Asn Gln His Pro His Pro Met Gln Ser Gln Tyr Pro Ala Leu Pro
                520                 525                 530 cat gac aca gct atc tct ggg cca ctc cac tat gcc cct tac cac agg    1750
His Asp Thr Ala Ile Ser Gly Pro Leu His Tyr Ala Pro Tyr His Arg
            535                 540                 545 agc tct gca cag tac cct ttt aat agc ccc act tcc cgg atg gaa cct    1798
Ser Ser Ala Gln Tyr Pro Phe Asn Ser Pro Thr Ser Arg Met Glu Pro
        550                 555                 560 tgt ttg atg agc agt act ccc aga ctg cat cct acc cca gtc act ccc    1846
Cys Leu Met Ser Ser Thr Pro Arg Leu His Pro Thr Pro Val Thr Pro
    565                 570                 575 cgc tgg cca gag gtg ccc tca gcc aac acg tgc tac aca agc ccg tct    1894
Arg Trp Pro Glu Val Pro Ser Ala Asn Thr Cys Tyr Thr Ser Pro Ser
580                 585                 590                 595 gtg cat tct gcg agg tac gga aac tct agt gac atg tat aca cct ctg    1942
Val His Ser Ala Arg Tyr Gly Asn Ser Ser Asp Met Tyr Thr Pro Leu
                600                 605                 610 aca acg cgc agg aat tct gaa tat gag cac atg caa cac ttt cct ggc    1990
Thr Thr Arg Arg Asn Ser Glu Tyr Glu His Met Gln His Phe Pro Gly
            615                 620                 625 ttt gct tac atc aac gga gag gcc tct aca gga tgg gct aaa tga       2035
Phe Ala Tyr Ile Asn Gly Glu Ala Ser Thr Gly Trp Ala Lys
        630                 635                 640 ctgctatcat aggcatccat atttaatatt aataataata attaataata ataataaacc  2095
caacacccat cccccagaag actttatctc tatacattgt aactcatggg ctattcctaa  2155
gtgcccattt tcctaatgaa catgaggatg ggatcaatgt gggatgaata aactttagtt  2215
cagaaacagg acttactaaa agtcagtggg actgggtttc tgtagccaag ccagacttga  2275
ctgtttctgt agagcactat ctcgggcagg ccattctgtg ccttttccct ctgttccatg  2335
actttgcttt gtgttggcaa ccacttctag taagctactg attttcctgt tgacaaaatc  2395
tctttagtct tgaaggatgg atactggaga cagaatctgg tttgtgttct tggatgggca  2455
cataatttac caagagcatt caccttgcca tctgtcttgt cattgtactg tacaaggaac  2515
```

```
agccctcaga cgtgttctgc acatcccttc ttcctggtgg taccatccct atttcctgga    2575
gcaccagggc taaatgggga gctatctgga aactctagat tttctgtcat acccacatct    2635
gtcacagtac ctgcattgtc ttggaatgta agcactgtct tgagggaagg aagaggtctg    2695
ttctgtattg ccttaagttg attgaggttt gtaggagact ggttcttcta catacaagga    2755
tttgtcttaa gtttgcacaa tggctagtgt cagcaaaagg caggagaggg ttttttgtttt   2815 ttttttaagt tctatgagaa tgtggattta tggcattgag tatcacactc agctctgctg    2875
tgttaacttt gtgaaactgg atggaacaaa ctttaactta ccaagcacca agtgtgaaag    2935
tgactttcac ggttccttca taaaactata ataatatccg acactttgat agaaaaaaat    2995
tcaaagctgt gcctttgagc ctatactata ctgtgtatgt gtggaaataa aaatgtattg    3055
tacttttgga gaattttttg taggcatttt tctgtcagat ttgtagtaat ttgtgaggtt    3115
tgttagagat taatataggt tttctttctg tattataaaa tgcaccaagc aattatggtg    3175
gacctattac cctatgggta agaaataaat ggaaatatga catcggatgt ttcagcaact    3235
gttctgtaaa taaaatcttt gatcacacca ctcagtgtga taattgtgtc tacagctaaa    3295
atggaaatag ttttatctgt acagttgtgc aagatatgaa tggtttcaca ctcaaataaa    3355
aaatattgaa acga                                                     3369
```

<210> SEQ ID NO 15
<211> LENGTH: 641
<212> TYPE: PRT
<213> ORGANISM: Homo sapiens

<400> SEQUENCE: 15

```
Met Asn Trp Ala Ala Phe Gly Gly Ser Glu Phe Phe Ile Pro Glu Gly
1               5                   10                  15

Ile Gln Ile Asp Ser Arg Cys Pro Leu Ser Arg Asn Ile Thr Glu Trp
            20                  25                  30

Tyr His Tyr Tyr Gly Ile Ala Val Lys Glu Ser Ser Gln Tyr Tyr Asp
        35                  40                  45

Val Met Tyr Ser Lys Lys Gly Ala Ala Trp Val Ser Glu Thr Gly Lys
    50                  55                  60

Lys Glu Val Ser Lys Gln Thr Val Ala Tyr Ser Pro Arg Ser Lys Leu
65                  70                  75                  80

Gly Thr Leu Leu Pro Glu Phe Pro Asn Val Lys Asp Leu Asn Leu Pro
                85                  90                  95

Ala Ser Leu Pro Glu Glu Lys Val Ser Thr Phe Ile Met Met Tyr Arg
            100                 105                 110

Thr His Cys Gln Arg Ile Leu Asp Thr Val Ile Arg Ala Asn Phe Asp
        115                 120                 125

Glu Val Gln Ser Phe Leu Leu His Phe Trp Gln Gly Met Pro Pro His
    130                 135                 140

Met Leu Pro Val Leu Gly Ser Ser Thr Val Val Asn Ile Val Gly Val
145                 150                 155                 160

Cys Asp Ser Ile Leu Tyr Lys Ala Ile Ser Gly Val Leu Met Pro Thr
                165                 170                 175

Val Leu Gln Ala Leu Pro Asp Ser Leu Thr Gln Val Ile Arg Lys Phe
            180                 185                 190

Ala Lys Gln Leu Asp Glu Trp Leu Lys Val Ala Leu His Asp Leu Pro
        195                 200                 205

Glu Asn Leu Arg Asn Ile Lys Phe Glu Leu Ser Arg Arg Phe Ser Gln
    210                 215                 220
```

```
Ile Leu Arg Arg Gln Thr Ser Leu Asn His Leu Cys Gln Ala Ser Arg
225                 230                 235                 240

Thr Val Ile His Ser Ala Asp Ile Thr Phe Gln Met Leu Glu Asp Trp
            245                 250                 255

Arg Asn Val Asp Leu Asn Ser Ile Thr Lys Gln Thr Leu Tyr Thr Met
        260                 265                 270

Glu Asp Ser Arg Asp Glu His Arg Lys Leu Ile Thr Gln Leu Tyr Gln
    275                 280                 285

Glu Phe Asp His Leu Leu Glu Glu Gln Ser Pro Ile Glu Ser Tyr Ile
290                 295                 300

Glu Trp Leu Asp Thr Met Val Asp Arg Cys Val Lys Val Ala Ala
305                 310                 315                 320

Lys Arg Gln Gly Ser Leu Lys Lys Val Ala Gln Phe Leu Leu Met
                325                 330                 335

Trp Ser Cys Phe Gly Thr Arg Val Ile Arg Asp Met Thr Leu His Ser
            340                 345                 350

Ala Pro Ser Phe Gly Ser Phe His Leu Ile His Leu Met Phe Asp Asp
        355                 360                 365

Tyr Val Leu Tyr Leu Leu Glu Ser Leu His Cys Gln Glu Arg Ala Asn
    370                 375                 380

Glu Leu Met Arg Ala Met Lys Gly Glu Gly Ser Thr Ala Glu Val Arg
385                 390                 395                 400

Glu Glu Ile Ile Leu Thr Glu Ala Ala Ala Pro Thr Pro Ser Pro Val
                405                 410                 415

Pro Ser Phe Ser Pro Ala Lys Ser Ala Thr Ser Val Glu Val Pro Pro
            420                 425                 430

Pro Ser Ser Pro Val Ser Asn Pro Ser Pro Glu Tyr Thr Gly Leu Ser
        435                 440                 445

Thr Thr Gly Ala Met Gln Ser Tyr Thr Trp Ser Leu Thr Tyr Thr Val
    450                 455                 460

Thr Thr Ala Ala Gly Ser Pro Ala Glu Asn Ser Gln Gln Leu Pro Cys
465                 470                 475                 480

Met Arg Asn Thr His Val Pro Ser Ser Val Thr His Arg Ile Pro
                485                 490                 495

Val Tyr Pro His Arg Glu Glu His Gly Tyr Thr Gly Ser Tyr Asn Tyr
            500                 505                 510

Gly Ser Tyr Gly Asn Gln His Pro His Pro Met Gln Ser Gln Tyr Pro
        515                 520                 525

Ala Leu Pro His Asp Thr Ala Ile Ser Gly Pro Leu His Tyr Ala Pro
    530                 535                 540

Tyr His Arg Ser Ser Ala Gln Tyr Pro Phe Asn Ser Pro Thr Ser Arg
545                 550                 555                 560

Met Glu Pro Cys Leu Met Ser Ser Thr Pro Arg Leu His Pro Thr Pro
                565                 570                 575

Val Thr Pro Arg Trp Pro Glu Val Pro Ser Ala Asn Thr Cys Tyr Thr
            580                 585                 590

Ser Pro Ser Val His Ser Ala Arg Tyr Gly Asn Ser Ser Asp Met Tyr
        595                 600                 605

Thr Pro Leu Thr Thr Arg Arg Asn Ser Glu Tyr Glu His Met Gln His
    610                 615                 620

Phe Pro Gly Phe Ala Tyr Ile Asn Gly Glu Ala Ser Thr Gly Trp Ala
625                 630                 635                 640

Lys
```

<210> SEQ ID NO 16
<211> LENGTH: 23
<212> TYPE: DNA
<213> ORGANISM: artificial sequence
<220> FEATURE:
<223> OTHER INFORMATION: synthetic oligonucleotide primer

<400> SEQUENCE: 16
aggtgggaag gcagttatga cag                                    23

<210> SEQ ID NO 17
<211> LENGTH: 25
<212> TYPE: DNA
<213> ORGANISM: artificial sequence
<220> FEATURE:
<223> OTHER INFORMATION: synthetic oligonucleotide primer

<400> SEQUENCE: 17
tccgtgatat ttctgcttag tgggc                                  25

<210> SEQ ID NO 18
<211> LENGTH: 28
<212> TYPE: DNA
<213> ORGANISM: artificial sequence
<220> FEATURE:
<223> OTHER INFORMATION: synthetic oligonucleotide primer

<400> SEQUENCE: 18
ggcagttatg acagttgaga agtagtag                               28

<210> SEQ ID NO 19
<211> LENGTH: 27
<212> TYPE: DNA
<213> ORGANISM: artificial sequence
<220> FEATURE:
<223> OTHER INFORMATION: synthetic oligonucleotide primer

<400> SEQUENCE: 19
ctgcttagtg ggcatctcga atctatc                                27

<210> SEQ ID NO 20
<211> LENGTH: 20
<212> TYPE: DNA
<213> ORGANISM: artificial sequence
<220> FEATURE:
<223> OTHER INFORMATION: synthetic oligonucleotide primer

<400> SEQUENCE: 20
ttttgacggg tttggctttg                                        20

<210> SEQ ID NO 21
<211> LENGTH: 22
<212> TYPE: DNA
<213> ORGANISM: artificial sequence
<220> FEATURE:
<223> OTHER INFORMATION: synthetic oligonucleotide primer

<400> SEQUENCE: 21
ttcctccagt aacccacaat gc                                     22

<210> SEQ ID NO 22
<211> LENGTH: 21
<212> TYPE: DNA
<213> ORGANISM: artificial sequence
<220> FEATURE:
<223> OTHER INFORMATION: synthetic oligonucleotide primer

```
<400> SEQUENCE: 22
tggagaggcc acagctgctg g                                              21

<210> SEQ ID NO 23
<211> LENGTH: 20
<212> TYPE: DNA
<213> ORGANISM: artificial sequence
<220> FEATURE:
<223> OTHER INFORMATION: synthetic oligonucleotide primer

<400> SEQUENCE: 23
tcgaggcctg gtcctgtcgc                                                20

<210> SEQ ID NO 24
<211> LENGTH: 20
<212> TYPE: DNA
<213> ORGANISM: artificial sequence
<220> FEATURE:
<223> OTHER INFORMATION: synthetic oligonucleotide primer

<400> SEQUENCE: 24
cacagctgct ggcttcctgg                                                20

<210> SEQ ID NO 25
<211> LENGTH: 25
<212> TYPE: DNA
<213> ORGANISM: artificial sequence
<220> FEATURE:
<223> OTHER INFORMATION: synthetic oligonucleotide primer

<400> SEQUENCE: 25
acaactctgc gatgggctct gcttt                                          25

<210> SEQ ID NO 26
<211> LENGTH: 25
<212> TYPE: DNA
<213> ORGANISM: artificial sequence
<220> FEATURE:
<223> OTHER INFORMATION: synthetic oligonucleotide primer

<400> SEQUENCE: 26
ctgaccaatt tgacggcgct gcaca                                          25

<210> SEQ ID NO 27
<211> LENGTH: 21
<212> TYPE: DNA
<213> ORGANISM: artificial sequence
<220> FEATURE:
<223> OTHER INFORMATION: synthetic oligonucleotide primer

<400> SEQUENCE: 27
ggccattgtc accactcgta a                                              21

<210> SEQ ID NO 28
<211> LENGTH: 21
<212> TYPE: DNA
<213> ORGANISM: artificial sequence
<220> FEATURE:
<223> OTHER INFORMATION: synthetic oligonucleotide primer

<400> SEQUENCE: 28
cacaagtaaa ggctaacgcg c                                              21

<210> SEQ ID NO 29
<211> LENGTH: 22
```

```
<212> TYPE: DNA
<213> ORGANISM: artificial sequence
<220> FEATURE:
<223> OTHER INFORMATION: synthetic oligonucleotide primer

<400> SEQUENCE: 29
agccagtaat aagaactgca ga                                                  22

<210> SEQ ID NO 30
<211> LENGTH: 22
<212> TYPE: DNA
<213> ORGANISM: artificial sequence
<220> FEATURE:
<223> OTHER INFORMATION: synthetic oligonucleotide primer

<400> SEQUENCE: 30
ggcactctta gcaaacctca gg                                                  22

<210> SEQ ID NO 31
<211> LENGTH: 21
<212> TYPE: DNA
<213> ORGANISM: artificial sequence
<220> FEATURE:
<223> OTHER INFORMATION: synthetic oligonucleotide primer

<400> SEQUENCE: 31
catggaaagg gcagagtgag c                                                   21

<210> SEQ ID NO 32
<211> LENGTH: 21
<212> TYPE: DNA
<213> ORGANISM: artificial sequence
<220> FEATURE:
<223> OTHER INFORMATION: synthetic oligonucleotide primer

<400> SEQUENCE: 32
ggccattgtc accactcgta a                                                   21

<210> SEQ ID NO 33
<211> LENGTH: 14
<212> TYPE: PRT
<213> ORGANISM: Homo sapiens

<400> SEQUENCE: 33

Met His Cys Gly Leu Leu Glu Glu Pro Asp Met Asp Ser Thr
1               5                   10

<210> SEQ ID NO 34
<211> LENGTH: 14
<212> TYPE: PRT
<213> ORGANISM: Mus musculus

<400> SEQUENCE: 34

Met His Cys Gly Leu Leu Glu Glu Pro Asp Met Asp Ser Thr
1               5                   10

<210> SEQ ID NO 35
<211> LENGTH: 14
<212> TYPE: PRT
<213> ORGANISM: Danio rerio

<400> SEQUENCE: 35

Met Leu Cys Gly Leu Leu Glu Glu Pro Asp Met Asp Ser Thr
1               5                   10

<210> SEQ ID NO 36
```

```
<211> LENGTH: 223
<212> TYPE: DNA
<213> ORGANISM: Homo sapiens

<400> SEQUENCE: 36
ctttggtgca gtgagagccg cctttcatag gaaaacagtt tgtgctcctg actgggccac      60
ctttcacccc ttgttcaagt agcagctcat ttggtaaggg gtcaggaata aagggctctt     120
tcttccctct ccatgtgtag gaaagtcagc ccttggtgtg gagagtcatt tctcaaaata     180
gatcttccta atatggttcc aaagagagca agagtcagtc aca                       223

<210> SEQ ID NO 37
<211> LENGTH: 2208
<212> TYPE: DNA
<213> ORGANISM: Homo sapiens

<400> SEQUENCE: 37
atgcattgtg ggttactgga ggaacccgac atggattcca cagagagctg gattgaaaga      60
tgtctcaacg aaagtgaaaa caaacgttat ccagccaca catctctggg gaatgtttct      120
aatgatgaaa atgaggaaaa agaaaataat agagcatcca agccccactc cactcctgct     180
actctgcaat ggctggagga gaactatgag attgcagagg gggtctgcat ccctcgcagt     240
gccctctata tgcattacct ggatttctgc gagaagaatg atacccaacc tgtcaatgct     300
gccagctttg gaaagatcat aaggcagcag tttcctcagt taaccaccag aagactcggg     360
acccgaggac agtcaaagta ccattactat ggcattgcag tgaaagaaag ctcccaatat     420
tatgatgtga tgtattccaa gaaggagct gcctgggtga gtgagacggg caagaaagaa      480
gtgagcaaac agacagtggc atattcaccc cggtccaaac tcggaacact gctgccagaa     540
tttcccaatg tcaaagatct aaatctgcca gccagcctgc ctgaggagaa ggtttctacc     600
tttattatga tgtacagaac acactgtcag agaatactgg acactgtaat aagagccaac     660
tttgatgagg ttcaaagttt ccttctgcac ttttggcaag gaatgccgcc ccacatgctg     720
cctgtgctgg gctcctccac ggtggtgaac attgtcggcg tgtgtgactc catcctctac     780
aaagctatct ccggggtgct gatgcccact gtgctgcagg cattacctga cagcttaact     840
caggtgattc gaaagtttgc caagcaactg gatgagtggc taaaagtggc tctccacgac     900
ctcccagaaa acttgcgaaa catcaagttc gaattgtcga aaggttctc ccaaattctg     960 agacggcaaa catcactaaa tcatctctgc caggcatctc gaacagtgat ccacagtgca    1020
gacatcacgt tccaaatgct ggaagactgg aggaacgtgg acctgaacag catcaccaag    1080
caaacccttt acaccatgga agactctcgc gatgagcacc ggaaactcat cacccaatta    1140
tatcaggagt ttgaccatct cttggaggag cagtctccca tcgagtccta cattgagtgg    1200
ctggatacca tggttgaccg ctgtgttgtg aaggtggctg ccaagagaca agggtccttg    1260
aagaaagtgg cccagcagtt cctcttgatg tggtcctgtt tcggcacaag ggtgatccgg    1320
gacatgacct tgcacagcgc ccccagcttc gggtctttc acctaattca cttaatgttt    1380
gatgactacg tgctctacct gttagaatct ctgcactgtc aggagcgggc caatgagctc    1440
atgcgagcca tgaagggaga aggaagcact gcagaagtcc gagaagagat catcttgaca    1500
gaggctgccg caccaacccc ttccaccagt ccatcgtttt ctccagcaaa atctgccaca    1560
tctatggaag tgccacctcc ctcttcccct gttagcaatc cttccctga gtacactggc    1620 ctcagcacta caggagcaat gcagtcttac acgtggtctc taacatacac agtgacgacg    1680
gctgctgggt ccccagctga gaactcccaa cagctgccct gtatgaggaa cactcatgtg    1740
```

-continued

| | |
|---|---|
| ccttcttcct ccgtcacaca caggatacca gtttatcccc acagagagga acatggatac | 1800 |
| acgggaagct ataactatgg gagctatggc aaccagcatc ctcaccccat gcagagccag | 1860 |
| tatccggccc tccctcatga cacagctatc tctgggccac tccactatgc cccttaccac | 1920 |
| aggagctctg cacagtaccc ttttaatagc cccacttccc ggatggaacc ttgtttgatg | 1980 |
| agcagtactc ccagactgca tcctacccca gtcactcccc gctggccaga ggtgccctca | 2040 |
| gccaacacgt gctacacaag cccgtctgtg cattctgcga ggtacggaaa ctctagtgac | 2100 |
| atgtatacac ctctgacaac gcgcaggaat tctgaatatg agcacatgca acactttcct | 2160 |
| ggctttgctt acatcaacgg agaggcctct acaggatggg ctaaatga | 2208 |

<210> SEQ ID NO 38
<211> LENGTH: 2214
<212> TYPE: DNA
<213> ORGANISM: Mus musculus

<400> SEQUENCE: 38

| | |
|---|---|
| atgcattgtg ggttactgga ggaacccgac atggattcca cagagagctg gattgaaaga | 60 |
| tgtctcaatg aaagcgagaa taaacgctat tccagtcaca catctctggg gaatgtgtct | 120 |
| aatgatgaaa atgaggaaaa agaaaataac agagcatcca gccccactc cacgccggcc | 180 |
| accctgcaat ggctggagga aaactatgag attgctgagg cgtctgcat cccccgcagc | 240 |
| gccctctaca tgcactacct ggatttctgt gagaagaacg acactcagcc tgtcaatgct | 300 |
| gccagctttg gaagatcat aaggcagcag tttcctcagc taaccaccag aagactcggg | 360 |
| accgggaccc gaggacagtc aaagtaccat tactatggca tagcggtgaa ggagagctcc | 420 |
| cagtattatg atgtgatgta ctcaaagaaa ggagctgcct gggtgagcga cgggcaag | 480 |
| agagaagtca ccaagcagac ggtggcatat tctccccggt ccaagcttgg acattgctg | 540 |
| ccagactttc aaacgtcaa agacctaaat ctgccagcca gtcttcctga ggagaaggtg | 600 |
| tctaccttta ttatgatgta cagaacacac tgtcagagaa tactgacac tgtaataaga | 660 |
| gccaactttg atgaggttca aagttttcctt ctgcactttt ggcaagggat gccgccccac | 720 |
| atgctgcccg tgctaggctc ctccacggtg gtgaacatcg tgggtgtgtg tgactccatc | 780 |
| ctctacaaag ccatctccgg tgtgttgatg cccacggtgc tgcaggcgtt gccggacagc | 840 |
| ttaactcagg tgatccgaaa gtttgccaag cagctggacg agtggctgaa agtggctctc | 900 |
| cacgatctcc cggaaaacct gagaaacatc aaatttgaat tatcaaggag gttttcccaa | 960 |
| atcctaagga ggcaaacatc gctgaaccat ctgtgccagg catctcgaac ggtgatccac | 1020 |
| agtgcagaca tcacgttcca gatgctggag gactggagga atgtggacct gagtagcatc | 1080 |
| accaagcaga ctctgtatac catggaggac tctcggatg agcaccgcag actcatcatc | 1140 |
| cagttgtacc aggagtttga ccacctgctg gaggaacagt cccccatcga gtcttacata | 1200 |
| gaatggctgg ataccatggt agaccgatgc gttgtaaagg tggctgccaa gagacaaggg | 1260 |
| tctctgaaga aagtagccca acagttcctg ctgatgtggt cttgctttgg tacgagggtg | 1320 |
| atccgggaca tgaccttgca cagtgccccc agcttcgggt cttttcacct gattcacctg | 1380 |
| atgttcgacg actacgtgct ctacttgcta gaatctctgc attgtcagga gcgggccaac | 1440 |
| gagctcatgc gagccatgaa aggagaagga agcactgcag aagcccagga agagattatc | 1500 |
| ttgacagagg ctaccccacc aacccccttca cctggtccat cattttctcc agcaaagtct | 1560 |
| gccacatctg tggaggtgcc acctccctcc tcccctgtca gcaacccatc ccccgaatac | 1620 |
| actggcctta gcacagcagg agcgatgcag tcatatacgt ggtcgctaac atatacagta | 1680 |

-continued

```
acaacggctg cagggtcacc ggctgagaac tcccaacaac taccctgtat gaggagcacc    1740
catatgcctt cttcctccgt cacacacagg ataccagtct actcccacag agaggagcat    1800
gggtacacgg gaagctataa ctacgggagc tatggcaacc agcatcctca cccactgcag    1860
aaccagtatc cagccttgcc tcatgacaca gccatctctg gcctctcca ctattccct      1920 taccacagga gctctgccca gtacccttc aatagccca cttccaggat ggaaccttgt      1980
ttgatgagca gtactcccag gctgcatcct accccagtga ctccccgatg ccagaggtg     2040 ccgactgcca acgcatgcta cacaagccca tctgtgcatt ccacgaggta tggaaactct    2100
agtgacatgt acaccccgct gaccacgcgc aggaattctg agtatgagca catgcaacac    2160
tttcctggct ttgcttacat caacggagag gcctccactg gatgggctaa gtga          2214
```

<210> SEQ ID NO 39
<211> LENGTH: 2208
<212> TYPE: DNA
<213> ORGANISM: Danio rerio

<400> SEQUENCE: 39

```
atgctttgtg ggctgctgga gagcctgac atggattcca cagagagctg gattgaaaga     60
tgtctgaacg aaagcgagag caagcgcttc tccagccact cttctattgg aaatatttcc    120
aacgacgaaa acgaagagaa ggaaaataac cgagcatcta agccacattc aacacctgct    180
acattacaat ggttggagga gaactacgag atcgcagagg gtgtgtgtat tcctcgcatc    240
gccctgtaca tgcactacct ggacttctgc gaaaaactgg actcacagcc agtcaatgct    300
gcaagcttcg gaaagataat aaggcagcag tttcctcagt tgaccacgcg gagattagga    360
actagaggtc aatcaaagta tcattactat ggcatcgcag tgaaggagag ctcccagtac    420
tacgatgtga tgtactctaa aaagggcgct gcgtgggtga acgagacggg caagaaagag    480
gtcaccaaac agacagtagc gtattccacg cgctccaagc tgggcactct cctgccagac    540
tttccaaatg tcaaagacct aaatctgccc gccagtctgc cagaggagaa ggtctcgacc    600
tttattatga tgtacagaac tcactgccag aggatactgg atactgtcat acgcgccaac    660
ttcgatgagg ttcagagctt cctgttgcac ttttggcagg gcatgccgcc ccacatgctc    720
cctgtcctgg gctcttctac agtggtcaac atagtgggtg tgtgtgactc catattgtac    780
aaggccatct caggcgtcct catgcccacc gtcctacaag ctctgcctga cagcctcact    840
caggtgatca ggaagtttgc caagcagctg gacgagtggc tgaaggtggc tttacatgac    900
ctgcccgaaa acctgcgcaa cattaagttt gaattgtcaa gagattttc tcagattctc     960 aaacgacaaa catcattaaa ccacctctgt caggcctctc gaacagtgat ccacagtgca    1020
gacatcacct ttcagatgct cgaggactgg aggaacgtag acctcaacag catcactaaa    1080
caaactcttt atactatgga agactccaga gaagaccaga ggagactcat catccaattg    1140
tatcaagaat ttgacagact gctagaggac cagtctccaa ttgaagccta catcgagtgg    1200
ctggactcta tggtggagag atgtgttgtg agggtggcgg ggaagagacc cggatctctg    1260
aagagggtag ctcagcagtt cctgctcatg tggtcgtgtt tgggacaag agttatccgg     1320 gatatgacgc tgcatagtgc accaagcttt ggctcgttcc atctgattca cctcatgttt    1380
gatgactatg tactttacct gcttgaatct ctgcactgcc aagagagagc caatgaactg    1440
atgagggcga tgaaaggaga gggcgcacca gcagatactg gagaagagct gatgctgatg    1500
agctccactc caacatctac gtcacctgga ccctactctc ctgccaaatc tgttcactcg    1560
gtgggcgtac ccgcagtagg gtcccccaat tcagcccagt ctccggagta caccagcata    1620
```

```
                                           -continued tcggccacaa caggagctgt tcagtcatat acctggtccc ttacatacac agtgacaact    1680
tcaggcggca gcccaaccga gcccggatcc cagctgtcct gcatgagagg cggacctgcg    1740
ttacacggat catcctccgc acaccggatg ccagtttacc cacatcggga tgagcacggg    1800
tacactggca gctataatta cagcagctac gcaaaccagc accatcatgc cattcagagt    1860
caatactcca gtttaaccca tgaagcaggg ctgcccactc ctttgcatta ttcctcatac    1920
caccgcacct ccgcacagta tccgctcaac agtcaaatgt ccagaatgga gtcgtgtcta    1980
atgagcggct ctcctctcct acactccagt ccagtgaccc ctcgatggcc cgatgtgccc    2040
tctgccaaca gctgttactc cagtcccacc gtccacgcat cccgctactc caccggagac    2100
atgtactcgc cccttgcccc acgcaggaac tctgaatacg agcacgcaca acactttcca    2160
ggattcgcct atattaacgg ggaggccacg accggatggg caaaatga                2208

<210> SEQ ID NO 40
<211> LENGTH: 221
<212> TYPE: DNA
<213> ORGANISM: Mus musculus

<400> SEQUENCE: 40
ctttgggaca gtgagagctg cctttcatag aaaaatggcc ttgtgctcct gcttcagcca      60
cctttcaccc cctgctcgat tgcggagcat gtggtgagag gcagggataa agggctcact     120 ctgcccttc catgtgcagg aaagttggcc ccaggagtgg ggagttgtgt cccaaaatag     180
acttcctaat acagttccaa agaggccaag agtcagtcac a                        221
```